US009624173B2

(12) United States Patent
Oslob et al.

(10) Patent No.: US 9,624,173 B2
(45) Date of Patent: Apr. 18, 2017

(54) HETEROCYCLIC MODULATORS OF LIPID SYNTHESIS

(71) Applicant: 3-V Biosciences, Inc., Menlo Park, CA (US)

(72) Inventors: Johan D. Oslob, Sunnyvale, CA (US); Robert S. McDowell, San Francisco, CA (US); Russell Johnson, San Mateo, CA (US); Hanbiao Yang, Sunnyvale, CA (US); Marc Evanchik, San Jose, CA (US); Cristiana A. Zaharia, Redwood City, CA (US); Haiying Cai, Cupertino, CA (US); Lily W. Hu, Palo Alto, CA (US)

(73) Assignee: 3-V Biosciences, Inc., Menlo Park, CA (US)

( * ) Notice: Subject to any disclaimer, the term of this patent is extended or adjusted under 35 U.S.C. 154(b) by 0 days.

(21) Appl. No.: 14/663,347

(22) Filed: Mar. 19, 2015

(65) Prior Publication Data
US 2015/0259292 A1    Sep. 17, 2015

Related U.S. Application Data

(63) Continuation-in-part of application No. 14/315,133, filed on Jun. 25, 2014, now abandoned, which is a continuation of application No. 13/415,660, filed on Mar. 8, 2012, now Pat. No. 8,871,790.

(60) Provisional application No. 61/585,642, filed on Jan. 11, 2012, provisional application No. 61/508,611, filed on Jul. 16, 2011, provisional application No. 61/450,561, filed on Mar. 8, 2011.

(51) Int. Cl.
| | |
|---|---|
| *A61K 31/445* | (2006.01) |
| *C07D 211/62* | (2006.01) |
| *C07D 401/14* | (2006.01) |
| *C07D 405/14* | (2006.01) |
| *C07D 413/14* | (2006.01) |
| *C07D 401/04* | (2006.01) |
| *C07D 401/06* | (2006.01) |
| *C07D 401/10* | (2006.01) |
| *C07D 401/12* | (2006.01) |
| *C07D 405/04* | (2006.01) |
| *C07D 405/10* | (2006.01) |
| *C07D 405/12* | (2006.01) |
| *C07D 413/10* | (2006.01) |
| *C07D 471/04* | (2006.01) |
| *C07D 487/04* | (2006.01) |
| *C07D 491/048* | (2006.01) |
| *C07D 491/052* | (2006.01) |
| *C07D 491/10* | (2006.01) |

(52) U.S. Cl.
CPC .......... *C07D 211/62* (2013.01); *C07D 401/04* (2013.01); *C07D 401/06* (2013.01); *C07D 401/10* (2013.01); *C07D 401/12* (2013.01); *C07D 401/14* (2013.01); *C07D 405/04* (2013.01); *C07D 405/10* (2013.01); *C07D 405/12* (2013.01); *C07D 405/14* (2013.01); *C07D 413/10* (2013.01); *C07D 413/14* (2013.01); *C07D 471/04* (2013.01); *C07D 487/04* (2013.01); *C07D 491/048* (2013.01); *C07D 491/052* (2013.01); *C07D 491/10* (2013.01)

(58) Field of Classification Search
CPC .................................................... C07D 487/04
USPC .......................................... 514/215; 540/578
See application file for complete search history.

(56) References Cited

U.S. PATENT DOCUMENTS

| | | | |
|---|---|---|---|
| 8,871,790 | B2 | 10/2014 | Oslob et al. |
| 2008/0103208 | A1 | 5/2008 | Ossovskaya et al. |
| 2009/0105305 | A1 | 4/2009 | Butlin et al. |
| 2009/0118332 | A1 | 5/2009 | Butlin et al. |
| 2014/0322355 | A1 | 10/2014 | Oslob et al. |

FOREIGN PATENT DOCUMENTS

| | | | |
|---|---|---|---|
| WO | WO 2007/063012 A1 | | 6/2007 |
| WO | WO 2008/059214 A1 | | 5/2008 |
| WO | WO 2008/075064 A1 | | 6/2008 |
| WO | WO 2008/075077 A1 | | 6/2008 |
| WO | WO 2012/122391 A1 | | 9/2012 |
| WO | WO2014008197 | * | 1/2014 |

OTHER PUBLICATIONS

Acton, Q. Ashton, "Multiple Myeloma: New Insights for the Healthcare Professional", 2013 Edition, p. 71.
Appel and Llinas, "Combination Therapy", http://www.healthcommunities.com/high-blood-pressure/combination-therapy_lhmwp.shtml, 2013, 1 page.
Bentzien et al., "Pyrrolidinyl and piperidinyl compounds useful as NHE-1 inhibitors and their preparation and pharmaceutical compositions," CAPLUS 152:144485, 2010.
Colombo et al., "Novel Platforms for Oral Drug Delivery", Pharmaceutical Research (2009), 26(3):601-611.
Cui, "Preparation of aminoheteroaryl compounds as protein kinase inhibitors," CAPLUS 141:260769, 2004.
International Preliminary Report on Patentability dated Jan. 6, 2015, for PCT International Application No. PCT/US2013/048950 (11 pages).
International Preliminary Report on Patentability for PCT/US2012/028309, mailed Sep. 19, 2013 (7 pages).
International Search Report and Written Opinion for PCT International Application No. PCT/US2013/048950, mailed Oct. 29, 2013 (17 pages).

(Continued)

Primary Examiner — Heidi Reese
(74) Attorney, Agent, or Firm — Cooley LLP

(57) ABSTRACT

Compounds that are fatty acid synthesis modulators are provided. The compounds may be used to treat disorders characterized by disregulation of the fatty acid synthase function by modulating the function and/or the fatty acid synthase pathway. Methods are provided for treating such disorders including viral infections, such as hepatitis C infection, cancer and metabolic disorders.

19 Claims, 1 Drawing Sheet

(56) References Cited

OTHER PUBLICATIONS

International Search Report and Written Opinion for PCT/US2012/028309, mailed Jul. 13, 2012 (10 pages).
Invitation to Pay Additional Fees and, Where Applicable, Protest Fee for PCT/US2013/048950, mailed Sep. 18, 2013 (4 pages).
Knust et al., "Preparation of piperidine derivatives as NK-3 receptor antagonists," CAPLUS 153:456481, 2010.
Menet et al., "Novel triazolopyridine compounds as JAK kinase inhibitors useful for the treatement of degenerative and inflammatory diseases and their preparation," CAPLUS 152:192130, 2010.
Notice of Allowance and Fee(s) Due for U.S. Appl. No. 13/415,660, dated Apr. 9, 2014 (8 pages).
Office Action for U.S. Appl. No. 13/415,660, dated Dec. 24, 2013 (7 pages).
Restriction Requirement for U.S. Appl. No. 13/415,660, dated Jul. 30, 2013 (7 pages).
Rodon et al., "Combining Targeted Therapies: Practical Issues to Consider at the Bench and Bedside", The Oncologist (2010), 15:37-50.
Schneider et al., "Preparation of 5-alkynyl-pyrimidines as kinase inhibitors," CAPLUS 155:271283, 2011.

\* cited by examiner

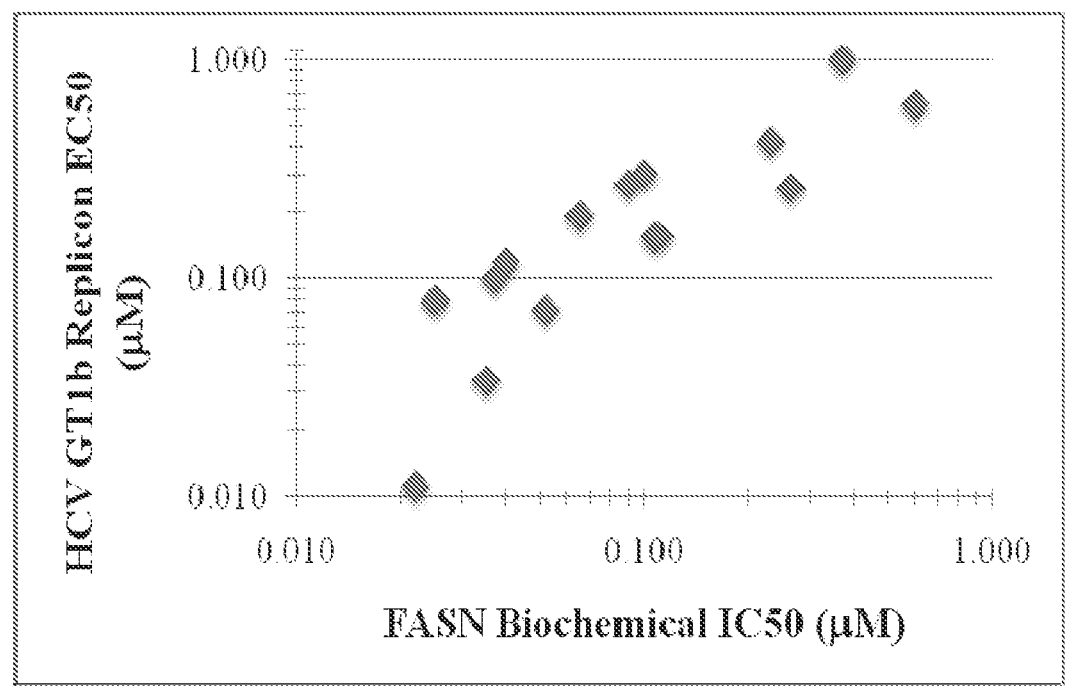

HETEROCYCLIC MODULATORS OF LIPID SYNTHESIS

RELATED APPLICATIONS

This application is a continuation-in-part of U.S. patent application Ser. No. 14/315,133, filed Jun. 25, 2014, now pending, which application is a continuation of U.S. patent application Ser. No. 13/415,660, filed Mar. 8, 2012, now issued U.S. Pat. No. 8,871,790, which application claims the benefit of the earlier filed U.S. Application No. 61/450,561 filed Mar. 8, 2011; U.S. Application No. 61/508,611 filed Jul. 16, 2011 and U.S. Application 61/585,642 filed on Jan. 11, 2012. Each application is hereby incorporated by reference in its entirety for all purposes.

FIELD

The present disclosure relates generally to heterocyclic modulators of lipid synthesis and methods of use thereof. The present heterocyclic modulators of lipid synthesis can be used for the treatment of disorders characterized by disregulation in the fatty acid synthase function in a subject by modulating the fatty acid synthase pathway and/or the fatty acid synthase function.

BACKGROUND

Viral disease is a significant health concern that threatens large segments of human populations. Some of the features related to viral infection which are of concern to health care professionals include its highly contagious nature (e.g., HIV, SARS, etc.) and high mutability. Some viruses are also oncogenic (such as HPV, EBV and HBV). While viruses are structurally amongst the simplest of organisms, they are regarded to be among the most difficult to control and present a formidable challenge for antiviral drug R&D.

Thus far, there have been a few antiviral drugs widely used in patients, such as Amantadine and Oseltamivir for influenza, Acyclovir for HSV-related infections, Ganciclovir for CMV infection, and multiple agents including co-formulated drugs (Efavirenz, emtricitabine, and tonfovir disoproxil fumarate) for AIDS treatments. These drugs possess a variety of undesirable neurological, metabolic and immunological side-effects. Therefore, development of new antiviral therapy has become a major focus of medical and pharmaceutical research and development.

Infection by hepatitis C virus (HCV) is a serious health issue. It is estimated that 170 million people worldwide are chronically infected with HCV. HCV infection can lead to chronic hepatitis, cirrhosis, liver failure and hepatocellular carcinoma. Chronic HCV infection is thus a major worldwide cause of liver-related premature mortality.

The present standard of care treatment regimen for HCV infection involves combination therapy with interferon-alpha and ribavirin, often with the addition of a direct-acting protease inhibitor (Telaprevir or Boceprevir). The treatment is cumbersome and sometimes has debilitating and severe side effects. For this reason, many patients are not treated in early stages of the disease. Additionally, some patient populations do not durably respond to treatment. New and effective methods of treating HCV infection are urgently needed.

The dominant therapeutic approaches that are currently employed to treat cancer include surgical removal of primary tumors, tumor irradiation, and parenteral application of anti-mitotic cytotoxic agents. Unfortunately, only a relatively small cross-section of cancer patients have tumors that are "addicted" to a specific pathway, and can therefore be treated with newer targeted agents. The continued dominance of these long established therapies is mirrored by the lack of improvement in survival rates for most cancers. In addition to limited clinical success, devastating side effects accompany classic therapies. Both radiation- and cytotoxic-based therapies result in the destruction of rapidly dividing hematopoietic and intestinal epithelial cells leading to compromised immune function, anemia, and impaired nutrient absorption. Surgical intervention often results in a release of tumor cells into the circulation or lymph systems from which metastatic tumors can subsequently be established. Improved methods for the treatment of cancer are needed.

SUMMARY

The present disclosure addresses the deficiencies for antiviral and anticancer treatments by providing novel heterocyclic modulators of lipid synthesis having improved antiviral and anticancer activities.

In various aspects, the present disclosure provides for compounds of Structure (I):

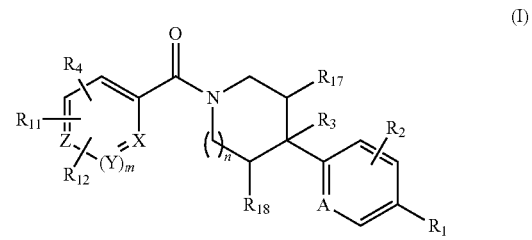

or a pharmaceutically acceptable salt thereof, wherein:

X, Y, and Z are each independently CR or NR', wherein R is hydrogen or $C_{1-6}$ alkyl and R' is hydrogen, $C_{1-6}$ alkyl, or absent;

A is CH or N;

$R_1$ is hydrogen, cyano, halo, $C_{1-6}$ alkyl, $C_{1-6}$ alkoxy, —C(=O)N($R_{13}$)($R_{14}$), —(CH$_2$)$_q$C(=O)N($R_{13}$)($R_{14}$), CF$_3$, —OCF$_3$, or —S(=O)$_2$R$_{20}$;

q is 0, 1, 2, 3, or 4;

$R_{20}$ is hydrogen or $C_{1-6}$ alkyl, $C_{1-6}$ alkoxy, or —N($R_{13}$)($R_{14}$);

$R_2$ is hydrogen, halo, $C_{1-6}$ alkoxy, $C_{1-6}$ alkyl, or $R_2$ and $R_3$ taken together with the atoms to which they are attached form a 5-membered heterocyclyl;

$R_3$ is hydrogen, hydroxyl, halo, $C_{1-6}$ alkyl, $C_{1-6}$ alkoxy, or $R_2$ and $R_3$ taken together with the atoms to which they are attached form a 5-membered heterocyclyl;

$R_4$ is hydrogen, heteroaryl, heterocyclyl, —C(=O)N($R_5R_6$), —N($R_7$)C(=O)$R_8$, —N($R_9R_{10}$), $C_{1-6}$ alkyl, $C_{1-6}$ alkoxy, —S(=O)$_2$R$_{20}$, or $R_4$ and $R_{11}$ taken together with the atoms to which they are attached join together to form a heteroaryl;

$R_{11}$ is hydrogen, halo, cyano, $C_{1-6}$ alkyl, $C_{1-6}$ alkoxy, —N($R_{13}R_{14}$), CF$_3$, —OCF$_3$, —S(=O)$_2$R$_{20}$, $R_4$ and $R_{11}$ taken together with the atoms to which they are attached join together to form a heteroaryl, or $R_{11}$ and $R_{12}$ taken together with the atoms to which they are attached join together to form a heteroaryl;

$R_{12}$ is hydrogen, halo, cyano, $C_{1-6}$ alkyl, $C_{1-6}$ alkoxy, —N($R_{13}R_{14}$), CF$_3$, —OCF$_3$, —S(=O)$_2$R$_{20}$, or $R_{11}$ and R$_{12}$ taken together with the atoms to which they are attached join together to form a heteroaryl;

R$_5$, R$_6$, R$_7$, R$_8$, R$_9$ R$_{10}$, R$_{13}$, and R$_{14}$ are each independently hydrogen, C$_{1-6}$ alkyl, cycloalkyl, aryl, heterocyclyl, heteroaryl, hydroxyalkyl, alkylamino, —N(R$_{15}$R$_{16}$), or —S(=O)$_2$R$_{20}$;

R$_{15}$ and R$_{16}$ are each independently hydrogen, C$_{1-6}$ alkyl, cycloalkyl, aryl, heterocyclyl, heteroaryl, or alkylamino;

R$_{17}$ and R$_{18}$ are each independently hydrogen or alkyl or can optionally join together to form a bond;

n is 1 or 2; and m is 0 or 1.

In various aspects, the present disclosure provides for compounds of Structure (II):

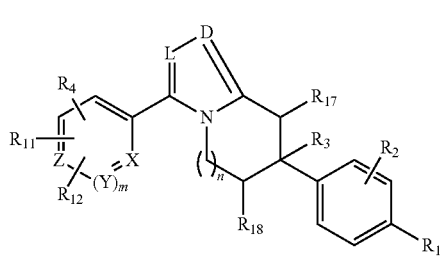

(II)

or a pharmaceutically acceptable salt thereof, wherein:

X, Y, and Z are each independently CR or NR', wherein R is hydrogen or C$_{1-6}$ alkyl and R' is hydrogen, C$_{1-6}$ alkyl, or absent;

L and D are each independently C or N;

R$_1$ is hydrogen, cyano, halo, C$_{1-6}$ alkyl, C$_{1-6}$ alkoxy, —C(=O)N(R$_{13}$)(R$_{14}$), —(CH$_2$)$_q$C(=O)N(R$_{13}$)(R$_{14}$), CF$_3$, —OCF$_3$, or —S(=O)$_2$R$_{20}$;

q is 0, 1, 2, 3, or 4;

R$_{20}$ is hydrogen or C$_{1-6}$ alkyl, C$_{1-6}$ alkoxy, or —N(R$_{13}$)(R$_{14}$);

R$_2$ is hydrogen, halo, C$_{1-6}$ alkoxy, C$_{1-6}$ alkyl, or R$_2$ and R$_3$ taken together with the atoms to which they are attached form a 5-membered heterocyclyl;

R$_3$ is hydrogen, hydroxyl, halo, C$_{1-6}$ alkyl, C$_{1-6}$ alkoxy, or R$_2$ and R$_3$ taken together with the atoms to which they are attached form a 5-membered heterocyclyl;

R$_4$ is hydrogen, heteroaryl, heterocyclyl, —C(=O)N(R$_5$R$_6$), —N(R$_7$)C(=O)R$_8$, —N(R$_9$R$_{10}$), C$_{1-6}$ alkyl, C$_{1-6}$ alkoxy, —S(=O)$_2$R$_{20}$, or R$_4$ and R$_{11}$ taken together with the atoms to which they are attached join together to form a heteroaryl;

R$_{11}$ is hydrogen, halo, cyano, C$_{1-6}$ alkyl, C$_{1-6}$ alkoxy, —N(R$_{13}$R$_{14}$), CF$_3$, —OCF$_3$, —S(=O)$_2$R$_{20}$, R$_4$ and R$_{11}$ taken together with the atoms to which they are attached join together to form a heteroaryl, or R$_{11}$ and R$_{12}$ taken together with the atoms to which they are attached join together to form a heteroaryl;

R$_{12}$ is hydrogen, halo, cyano, C$_{1-6}$ alkyl, C$_{1-6}$ alkoxy, —N(R$_{13}$R$_{14}$), CF$_3$, —OCF$_3$, —S(=O)$_2$R$_{20}$, or R$_{11}$ and R$_{12}$ taken together with the atoms to which they are attached join together to form a heteroaryl;

R$_5$, R$_6$, R$_7$, R$_8$, R$_9$ R$_{10}$, R$_{13}$, and R$_{14}$ are each independently hydrogen, C$_{1-6}$ alkyl, cycloalkyl, aryl, heterocyclyl, heteroaryl, hydroxyalkyl, alkylamino, —N(R$_{15}$R$_{16}$), or —S(=O)$_2$R$_{20}$;

R$_{15}$ and R$_{16}$ are each independently hydrogen, C$_{1-6}$ alkyl, cycloalkyl, aryl, heterocyclyl, heteroaryl, or alkylamino;

R$_{17}$ and R$_{18}$ are each independently hydrogen or alkyl or can optionally join together to form a bond;

n is 1 or 2; and m is 0 or 1.

In various aspects, the present disclosure provides for compounds of Structure (III):

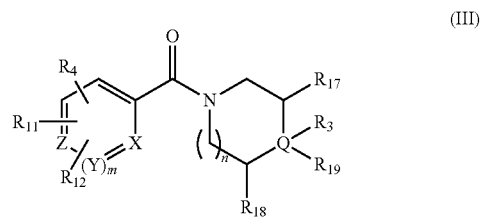

(III)

or a pharmaceutically acceptable salt thereof, wherein:

X, Y, and Z are each independently CR or NR', wherein R is hydrogen or C$_{1-6}$ alkyl and R' is hydrogen, C$_{1-6}$ alkyl, or absent;

Q is C or N;

R$_3$ is hydrogen, hydroxyl, halo, C$_{1-6}$ alkyl, C$_{1-6}$ alkoxy, or if Q is N then R$_3$ is absent;

R$_4$ is hydrogen, heteroaryl, heterocyclyl, —C(=O)N(R$_5$R$_6$), —N(R$_7$)C(=O)R$_8$, —N(R$_9$R$_{10}$), C$_{1-6}$ alkyl, C$_{1-6}$ alkoxy, —S(=O)$_2$R$_{20}$, or R$_4$ and R$_{11}$ taken together with the atoms to which they are attached join together to form a heteroaryl;

R$_{11}$ is hydrogen, halo, cyano, C$_{1-6}$ alkyl, C$_{1-6}$ alkoxy, —N(R$_{13}$R$_{14}$), CF$_3$, —OCF$_3$, —S(=O)$_2$R$_{20}$, R$_4$ and R$_{11}$ taken together with the atoms to which they are attached join together to form a heteroaryl, or R$_{11}$ and R$_{12}$ taken together with the atoms to which they are attached join together to form a heteroaryl;

R$_{12}$ is hydrogen, halo, cyano, C$_{1-6}$ alkyl, C$_{1-6}$ alkoxy, —N(R$_{13}$R$_{14}$), CF$_3$, —OCF$_3$, —S(=O)$_2$R$_{20}$, or R$_{11}$ and R$_{12}$ taken together with the atoms to which they are attached join together to form a heteroaryl;

R$_{20}$ is hydrogen or C$_{1-6}$ alkyl, C$_{1-6}$ alkoxy, or —N(R$_{13}$)(R$_{14}$);

R$_5$, R$_6$, R$_7$, R$_8$, R$_9$ R$_{10}$, R$_{13}$, and R$_{14}$ are each independently hydrogen, C$_{1-6}$ alkyl, cycloalkyl, aryl, heterocyclyl, heteroaryl, hydroxyalkyl, alkylamino, —N(R$_{15}$R$_{16}$), or —S(=O)$_2$R$_{20}$;

R$_{15}$ and R$_{16}$ are each independently hydrogen, C$_{1-6}$ alkyl, cycloalkyl, aryl, heterocyclyl, heteroaryl, or alkylamino;

R$_{17}$ and R$_{18}$ are each independently hydrogen or alkyl or can optionally join together to form a bond;

R$_{19}$ is aryl, heteroaryl, cycloalkyl, or heterocyclyl;

n is 0, 1, or 2; and m is 0 or 1.

In various aspects, the present disclosure provides for compounds of Structures (IV-A), (IV-B), or (IV-C):

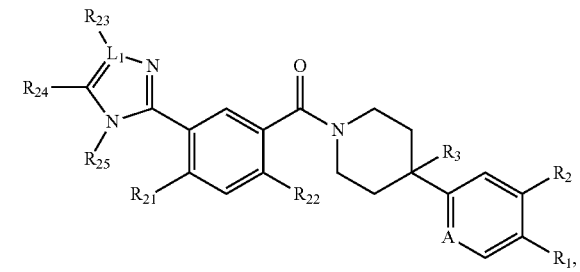

(IV-A)

-continued (IV-B)

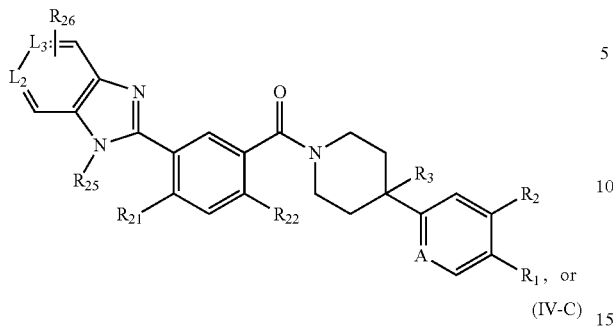

or (IV-C)

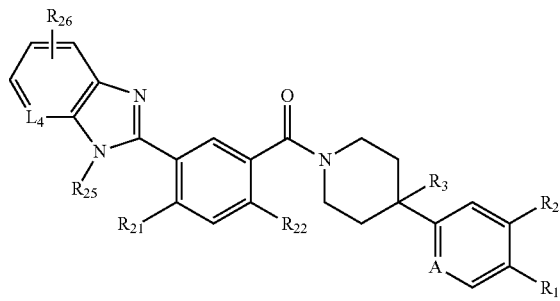

or a pharmaceutically acceptable salt thereof, wherein:

$L_1$, $L_2$, $L_3$, $L_4$, and A are each independently CH or N;

$R_1$ is hydrogen, cyano, halo, $C_{1-6}$ alkyl, $C_{1-6}$ alkoxy, —C(=O)N($R_{13}$)($R_{14}$), —(CH$_2$)$_q$C(=O)N($R_{13}$)($R_{14}$), CF$_3$, —OCF$_3$, or —S(=O)$_2$R$_{20}$;

q is 0, 1, 2, 3, or 4;

$R_{20}$ is hydrogen or $C_{1-6}$ alkyl, $C_{1-6}$ alkoxy, or —N($R_{13}$)($R_{14}$);

$R_2$ is hydrogen, halo, $C_{1-6}$ alkoxy, or $C_{1-6}$ alkyl;

$R_3$ is hydrogen, hydroxyl, halo, $C_{1-6}$ alkyl, or $C_{1-6}$ alkoxy;

$R_{21}$ and $R_{22}$ are each independently hydrogen, halo, cyano, $C_{1-6}$ alkyl, $C_{1-6}$ alkoxy, CF$_3$, —OCF$_3$, or —S(=O)$_2$R$_{20}$;

$R_{23}$ is hydrogen, —N($R_{13}$)($R_{14}$), $C_{1-6}$ alkyl, $C_{1-6}$ alkoxy, is absent if $L_1$ is N, or $R_{23}$ and $R_{24}$ taken together with the atoms to which they are attached join together to form a heterocyclyl, heteroaryl, or cycloalkyl;

$R_{24}$ is hydrogen, —N($R_{13}$)($R_{14}$), $C_{1-6}$ alkyl, $C_{1-6}$ alkoxy, —(C$_{1-6}$ alkoxy)(heterocyclyl), heterocyclyl, or $R_{23}$ and $R_{24}$ taken together with the atoms to which they are attached join together to form a heterocyclyl, heteroaryl, or cycloalkyl;

$R_{26}$ is hydrogen, heteroaryl, heterocycyl, —N($R_{13}$)($R_{14}$), or —S(=O)$_2$R$_{20}$;

$R_{13}$ and $R_{14}$ are each independently hydrogen, $C_{1-6}$ alkyl, cycloalkyl, aryl, heterocyclyl, heteroaryl, hydroxyalkyl, alkylamino, —N($R_{15}R_{16}$), or —S(=O)$_2$R$_{20}$;

$R_{25}$ is hydrogen, $C_{1-6}$ alkyl, or $C_{1-6}$ alkoxy; and $R_{15}$ and $R_{16}$ are each independently hydrogen, $C_{1-6}$ alkyl, $C_{1-6}$ alkoxy, cycloalkyl, aryl, heterocyclyl, heteroaryl, hydroxyalkyl, or alkylamino.

In various aspects, the present disclosure provides for compounds of Structure (V):

(V)

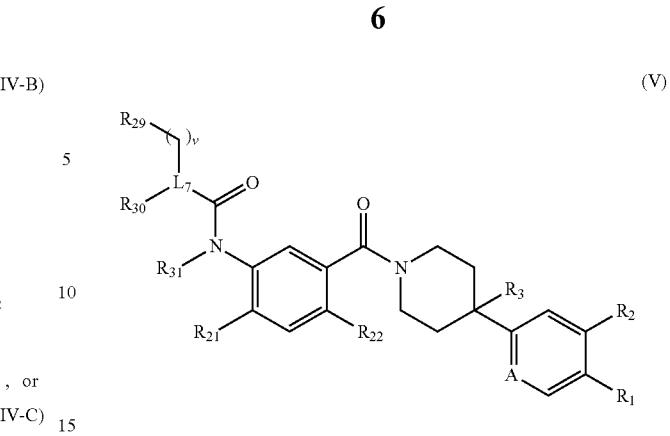

or a pharmaceutically acceptable salt thereof, wherein:

$L_7$ is N or O, wherein $R_{30}$ is absent if $L_7$ is O;

A is CH or N;

$R_1$ is hydrogen, cyano, halo, $C_{1-6}$ alkyl, $C_{1-6}$ alkoxy, —C(=O)N($R_{13}$)($R_{14}$), —(CH$_2$)$_q$C(=O)N($R_{13}$)($R_{14}$), CF$_3$, —OCF$_3$, or —S(=O)$_2$R$_{20}$;

q is 0, 1, 2, 3, or 4;

$R_{20}$ is hydrogen or $C_{1-6}$ alkyl, $C_{1-6}$ alkoxy, or —N($R_{13}$)($R_{14}$);

$R_2$ is hydrogen, halo, $C_{1-6}$ alkoxy, or $C_{1-6}$ alkyl;

$R_3$ is halo, $C_{1-6}$ alkyl, or $C_{1-6}$ alkoxy;

$R_{21}$ and $R_{22}$ are each independently hydrogen, halo, cyano, $C_{1-6}$ alkyl, $C_{1-6}$ alkoxy, CF$_3$, —OCF$_3$, or —S(=O)$_2$R$_{20}$;

$R_{29}$ and $R_{30}$ are each independently hydrogen, $C_{1-6}$ alkyl, $C_{1-6}$ alkoxy, hydroxyalkyl, heteroaryl, heterocyclyl, —N($R_{15}R_{16}$), —C(=O)$R_{46}$, —$R_{48}$C(=O)$R_{47}$, or $R_{29}$ and $R_{30}$ taken together with the atoms to which they are attached join together to form a heteroaryl or heterocyclyl, wherein $R_{30}$ is absent if $L_7$ is O;

$R_{46}$ and $R_{47}$ are each independently hydrogen, $C_{1-6}$ alkyl, cycloalkyl, aryl, heterocyclyl, heteroaryl, hydroxyalkyl, —N($R_{15}R_{16}$), or —S(=O)$_2$R$_{20}$;

$R_{48}$ is alkyl or is absent;

$R_{31}$ is hydrogen, $C_{1-6}$ alkyl, or $C_{1-6}$ alkoxy;

$R_{13}$ and $R_{14}$ are each independently hydrogen, $C_{1-6}$ alkyl, cycloalkyl, aryl, heterocyclyl, heteroaryl, hydroxyalkyl, alkylamino, —N($R_{15}R_{16}$), or —S(=O)$_2$R$_{20}$;

$R_{15}$ and $R_{16}$ are each independently hydrogen, $C_{1-6}$ alkyl, cycloalkyl, aryl, heterocyclyl, heteroaryl, hydroxyalkyl, or alkylamino; and v is 0 or 1.

In various aspects, the present disclosure provides for compounds of Structures (VI-A) or (VI-B):

(VI-A)

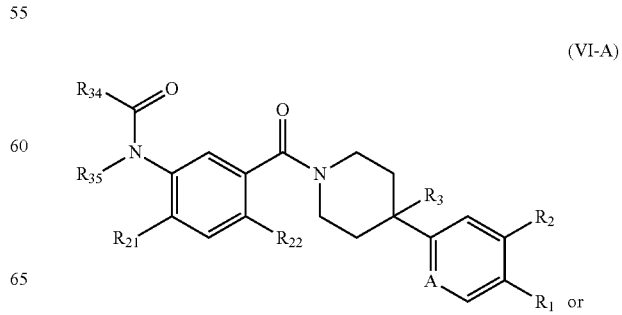

or

-continued (VI-B)

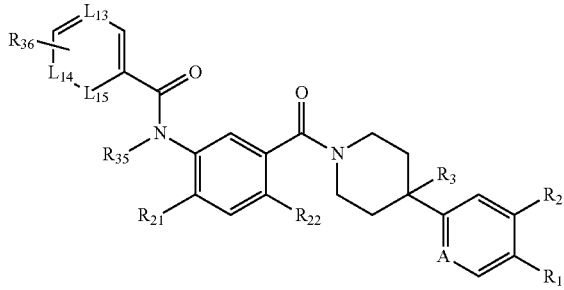

or a pharmaceutically acceptable salt thereof, wherein:
$L_{13}$, $L_{14}$, $L_{15}$, and A are each independently CH or N;
$R_1$ is hydrogen, cyano, halo, $C_{1-6}$ alkyl, $C_{1-6}$ alkoxy, —C(=O)N($R_{13}$)($R_{14}$), —(CH$_2$)$_q$C(=O)N($R_{13}$)($R_{14}$), CF$_3$, —OCF$_3$, or —S(=O)$_2$R$_{20}$;
q is 0, 1, 2, 3, or 4;
$R_{20}$ is hydrogen or $C_{1-6}$ alkyl, $C_{1-6}$ alkoxy, or —N($R_{13}$)($R_{14}$);
$R_2$ is hydrogen, halo, $C_{1-6}$ alkoxy, or $C_{1-6}$ alkyl;
$R_3$ is halo, $C_{1-6}$ alkyl, or $C_{1-6}$ alkoxy;
$R_{21}$ and $R_{22}$ are each independently hydrogen, halo, cyano, $C_{1-6}$ alkyl, $C_{1-6}$ alkoxy, CF$_3$, —OCF$_3$, or —S(=O)$_2$R$_{20}$;
$R_{34}$ is hydrogen, $C_{1-6}$ alkyl, $C_{1-6}$ alkoxy, cycloalkyl, hydroxyl, hydroxyalkyl, aryl, heterocyclyl, heteroaryl, alkylamino, CF$_3$, —OCF$_3$, —S(=O)$_2$R$_{20}$, or —N($R_{15}R_{16}$);
$R_{35}$ is hydrogen, $C_{1-6}$ alkyl, or $C_{1-6}$ alkoxy;
$R_{36}$ is hydrogen, $C_{1-6}$ alkyl, $C_{1-6}$ alkoxy, heterocyclyl, or heteroaryl;
$R_{13}$ and $R_{14}$ are each independently hydrogen, $C_{1-6}$ alkyl, cycloalkyl, aryl, heterocyclyl, heteroaryl, hydroxyalkyl, alkylamino, —N($R_{15}R_{16}$), or —S(=O)$_2$R$_{20}$; and
$R_{15}$ and $R_{16}$ are each independently hydrogen, $C_{1-6}$ alkyl, $C_{1-6}$ alkoxy, cycloalkyl, aryl, heterocyclyl, heteroaryl, hydroxyalkyl, or alkylamino.

In various aspects, the present disclosure provides for compounds of Structure (VI-J):

(VI-J)

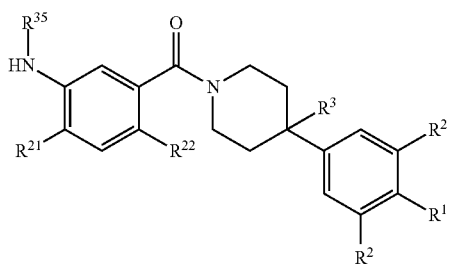

or a pharmaceutically acceptable salt thereof, wherein:
$R^1$ is H, —CN, halogen, $C_1$-$C_4$ straight or branched alkyl, —O—($C_3$-$C_5$ cycloalkyl), —O—($C_1$-$C_4$ straight or branched alkyl) wherein:
the $C_3$-$C_5$ cycloalkyl optionally includes an oxygen or nitrogen heteroatom; and when $R^1$ is not H, —CN or halogen, it is optionally substituted with one or more halogens;
each $R^2$ is independently H, halogen or $C_1$-$C_4$ straight or branched alkyl;
$R^3$ is H, —OH, or halogen;
$R^{21}$ is cyclobutyl, azetidin-1-yl, or cyclopropyl;
$R^{22}$ is H, halogen, or $C_1$-$C_2$ alkyl;
$R^{35}$ is —C(O)—R$^{351}$, —C(O)—NHR$^{351}$, —C(O)—O—R$^{351}$ or S(O)$_2$R$^{351}$; and
$R^{351}$ is $C_1$-$C_6$ straight or branched alkyl, cycloalkyl, heterocyclyl, aryl or heteroaryl.

In some aspects of Structure (VI-J), $R^3$ is H or halogen.

In some aspects of Structure (VI-J), $R^1$ is halogen, —CN or $C_1$-$C_2$ haloalkyl.

In some aspects of Structure (VI-J), $R^{22}$ is $C_1$-$C_2$ alkyl.

In some aspects of Structure (VI-J), $R^{21}$ is cyclobutyl and $R^{22}$ is $C_1$-$C_2$ alkyl.

In some aspects of Structure (VI-J), $R^{21}$ is cyclobutyl.

In some aspects of Structure (VI-J), $R^3$ is H or F.

In some aspects of Structure (VI-J), $R^1$ is —CN.

In some aspects of Structure (VI-J), $R^1$ is —CF$_3$.

In some aspects of Structure (VI-J), $R^{22}$ is H, methyl or ethyl.

In some aspects of Structure (VI-J), $R^{22}$ is H.

In some aspects of Structure (VI-J), $R^{22}$ is methyl.

In some aspects of Structure (VI-J), $R^{35}$ is —C(O)—NHR$^{351}$.

In some aspects of Structure (VI-J), $R^{351}$ is isopropyl, isobutyl, (R)-3-tetrahydrofuranyl, (S)-3-tetrahydrofuranyl, (R)-(tetrahydrofuran-2-yl)methyl, (S)-(tetrahydrofuran-2-yl)methyl, (R)-tetrahydro-2H-pyran-3-yl or (S)-tetrahydro-2H-pyran-3-yl.

In some aspects of Structure (VI-J), $R^{351}$ is (R)-(tetrahydrofuran-2-yl)methyl or (S)-(tetrahydrofuran-2-yl)methyl.

In some aspects of Structure (VI-J), $R^1$ is —CN, each $R^2$ is hydrogen, $R^3$ is H or F, $R^{21}$ is $C_3$-$C_4$ cycloalkyl, $R^{22}$ is H, $R^{35}$ is —C(O)—NHR$^{351}$ where $R^{351}$ is isopropyl, isobutyl, (R)-3-tetrahydrofuranyl, (S)-3-tetrahydrofuranyl, (R)-(tetrahydrofuran-2-yl)methyl, (S)-(tetrahydrofuran-2-yl)methyl, (R)-tetrahydro-2H-pyran-3-yl, or (S)-tetrahydro-2H-pyran-3-yl.

In some aspects of Structure (VI-J), $R^{35}$ is —C(O)—O—R$^{351}$.

In some aspects of Structure (VI-J), $R^{351}$ is isopropyl, isobutyl, (R)-3-tetrahydrofuranyl, (S)-3-tetrahydrofuranyl, (R)-(tetrahydrofuran-2-yl)methyl, (S)-(tetrahydrofuran-2-yl)methyl, (R)-tetrahydro-2H-pyran-3-yl, or (S)-tetrahydro-2H-pyran-3-yl.

In some aspects of Structure (VI-J), $R^1$ is —CN, each $R^2$ is H, $R^3$ is H or F, $R^{21}$ is $C_3$-$C_4$ cycloalkyl, $R^{22}$ is H, $R^{35}$ is —C(O)—O—R$^{351}$ where $R^{351}$ is isopropyl, isobutyl, (R)-3-tetrahydrofuranyl, (S)-3-tetrahydrofuranyl, (R)-(tetrahydrofuran-2-yl)methyl, (S)-(tetrahydrofuran-2-yl)methyl, (R)-tetrahydro-2H-pyran-3-yl, or (S)-tetrahydro-2H-pyran-3-yl.

In some aspects of Structure (VI-J), $R^{351}$ is (R)-3-tetrahydrofuranyl or (S)-3-tetrahydrofuranyl.

In some aspects of Structure (VI-J), compounds have a structure selected from the group consisting of:

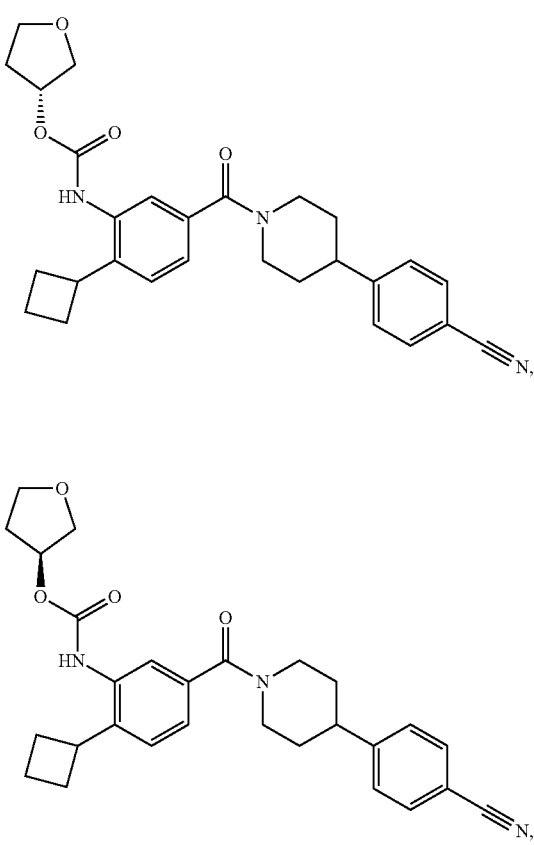
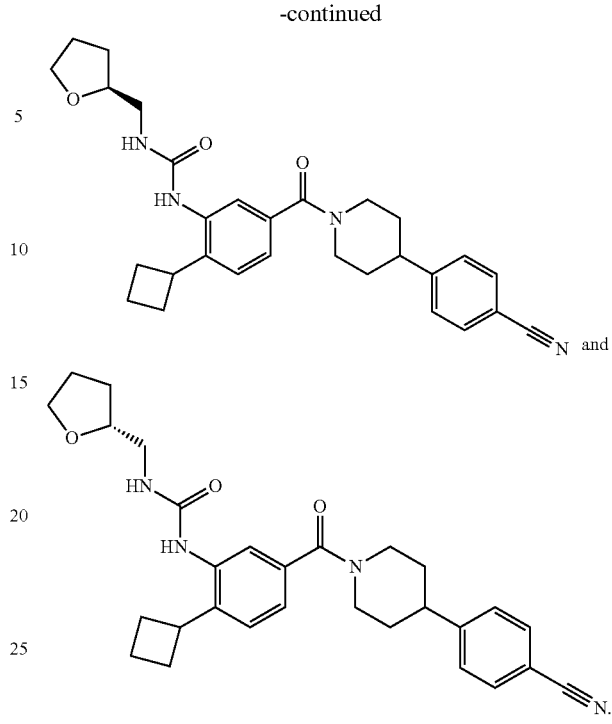
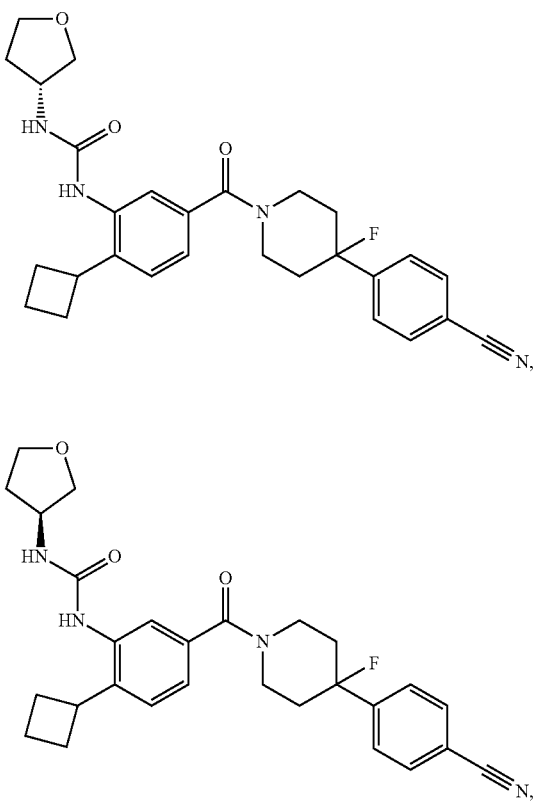
In various aspects, the present disclosure provides for compounds of Structures (VII-A) or (VII-B):
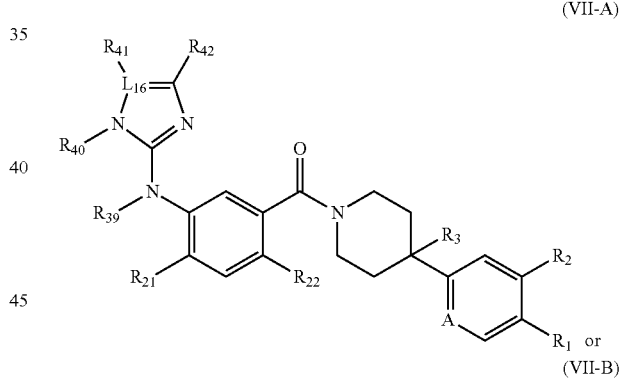
(VII-A)
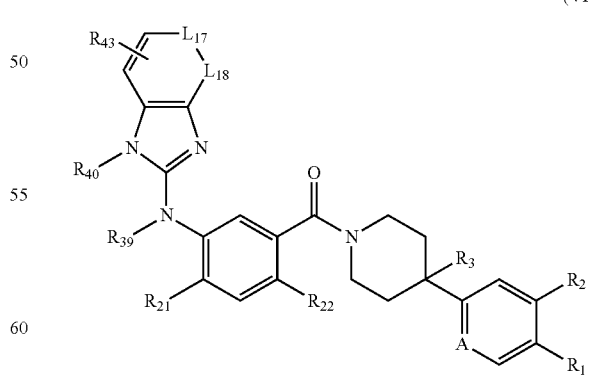
(VII-B)
or a pharmaceutically acceptable salt thereof, wherein:
$L_{16}$ is C or N, wherein $R_{41}$ is absent if $L_{16}$ is N;
$L_{17}$, $L_{18}$, and A are each independently CH or N;

$R_1$ is hydrogen, cyano, halo, $C_{1-6}$ alkyl, $C_{1-6}$ alkoxy, —C(=O)N($R_{13}$)($R_{14}$), —(CH$_2$)$_q$C(=O)N($R_{13}$)($R_{14}$), CF$_3$, —OCF$_3$, or —S(=O)$_2$R$_{20}$;

q is 0, 1, 2, 3, or 4;

$R_{20}$ is hydrogen or $C_{1-6}$ alkyl, $C_{1-6}$ alkoxy, or —N($R_{13}$)($R_{14}$);

$R_2$ is hydrogen, halo, $C_{1-6}$ alkoxy, or $C_{1-6}$ alkyl;

$R_3$ is hydrogen, hydroxyl, halo, $C_{1-6}$ alkyl, or $C_{1-6}$ alkoxy;

$R_{21}$ and $R_{22}$ are each independently hydrogen, halo, cyano, $C_{1-6}$ alkyl, $C_{1-6}$ alkoxy, CF$_3$, —OCF$_3$, or —S(=O)$_2$R$_{20}$;

$R_{40}$, $R_{42}$, and $R_{43}$ are each independently hydrogen, $C_{1-6}$ alkyl, $C_{1-6}$ alkoxy, —S(=O)$_2$R$_{20}$, —C(=O)R, hydroxyalkyl, hydroxyl, —N($R_{13}R_{14}$), or $R_{41}$ and $R_{42}$ taken together with the atoms they are attached join together to form a heteroaryl or heterocyclyl;

$R_{41}$ is hydrogen, $C_{1-6}$ alkyl, $C_{1-6}$ alkoxy, —S(=O)$_2$R$_{20}$, —C(=O)R, hydroxyalkyl, hydroxyl, —N($R_{13}R_{14}$), $R_{41}$ is absent if $L_{16}$ is N, or $R_{41}$ and $R_{42}$ taken together with the atoms to which they are attached join together to form a heteroaryl or heterocyclyl;

R is hydrogen, $C_{1-6}$ alkyl, cycloalkyl, aryl, heterocyclyl, heteroaryl, hydroxyalkyl, —N($R_{15}R_{16}$), or —S(=O)$_2$R$_{20}$;

$R_{39}$ is hydrogen, $C_{1-6}$ alkyl, or $C_{1-6}$ alkoxy;

$R_{13}$ and $R_{14}$ are each independently hydrogen, $C_{1-6}$ alkyl, cycloalkyl, aryl, heterocyclyl, heteroaryl, hydroxyalkyl, alkylamino, —N($R_{15}R_{16}$), or —S(=O)$_2$R$_{20}$; and $R_{15}$ and $R_{16}$ are each independently hydrogen, $C_{1-6}$ alkyl, cycloalkyl, aryl, heterocyclyl, heteroaryl, hydroxyalkyl, or alkylamino.

In various aspects, the present disclosure provides for compounds of Structures (VIII-A), (VIII-B), or (VIII-C):

(VIII-A)

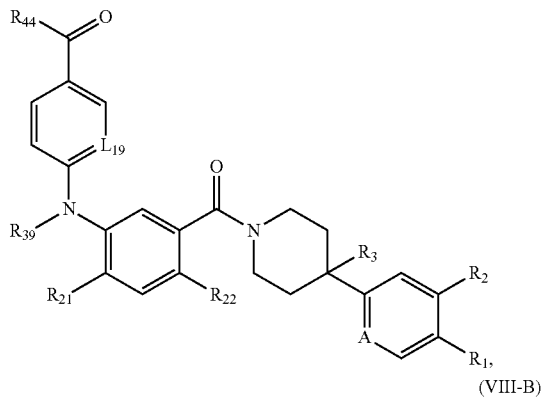

(VIII-B)

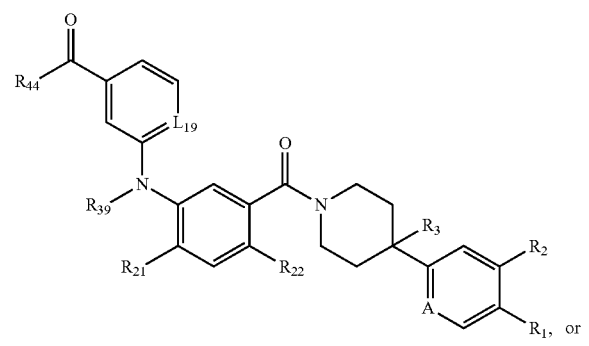

or (VIII-C)

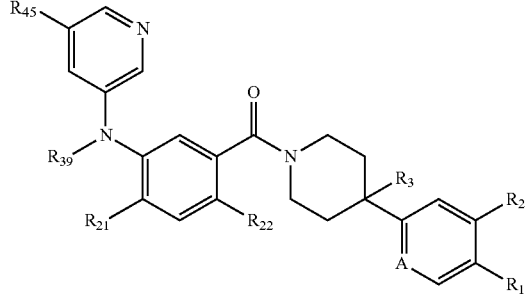

or a pharmaceutically acceptable salt thereof, wherein:

$L_{19}$ and A are each independently CH or N;

$R_1$ is hydrogen, cyano, halo, $C_{1-6}$ alkyl, $C_{1-6}$ alkoxy, —C(=O)N($R_{13}$)($R_{14}$), —(CH$_2$)$_q$C(=O)N($R_{13}$)($R_{14}$), CF$_3$, —OCF$_3$, or —S(=O)$_2$R$_{20}$;

q is 0, 1, 2, 3, or 4;

$R_{20}$ is hydrogen or $C_{1-6}$ alkyl, $C_{1-6}$ alkoxy, or —N($R_{13}$)($R_{14}$);

$R_2$ is hydrogen, halo, $C_{1-6}$ alkoxy, or $C_{1-6}$ alkyl;

$R_3$ is hydrogen, hydroxyl, halo, $C_{1-6}$ alkyl, or $C_{1-6}$ alkoxy;

$R_{21}$ and $R_{22}$ are each independently hydrogen, halo, cyano, $C_{1-6}$ alkyl, $C_{1-6}$ alkoxy, CF$_3$, —OCF$_3$, or —S(=O)$_2$R$_{20}$;

$R_{39}$ is hydrogen, $C_{1-6}$ alkyl, or $C_{1-6}$ alkoxy;

$R_{44}$ and $R_{45}$ are each independently hydrogen, $C_{1-6}$ alkyl, $C_{1-6}$ alkoxy, cycloalkyl, hydroxyalkyl, aryl, heterocyclyl, heteroaryl, alkylamino, —S(=O)$_2$R$_{20}$, —C(=O)R, or —N($R_{13}R_{14}$); and $R_{13}$ and $R_{14}$ are each independently hydrogen, $C_{1-6}$ alkyl, cycloalkyl, aryl, heterocyclyl, heteroaryl, hydroxyalkyl, alkylamino, —N($R_{15}R_{16}$), or —S(=O)$_2$R$_{20}$; and $R_{15}$ and $R_{16}$ are each independently hydrogen, $C_{1-6}$ alkyl, cycloalkyl, aryl, heterocyclyl, heteroaryl, hydroxyalkyl, or alkylamino.

In various aspects, compounds of Structure (IX) are provided:

(IX)

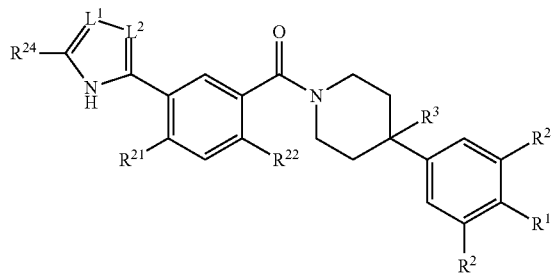

or a pharmaceutically acceptable salt thereof, wherein:

$R^1$ is H, —CN, halogen, $C_1$-$C_4$ straight or branched alkyl, —O—($C_3$-$C_5$ cycloalkyl), —O—($C_1$-$C_4$ straight or branched alkyl) wherein:

$C_3$-$C_5$ cycloalkyl optionally includes an oxygen or nitrogen heteroatom; and when $R^1$ is not H, —CN or halogen, it is optionally substituted with one or more halogens;

each $R^2$ is independently hydrogen, halogen or $C_1$-$C_4$ straight or branched alkyl;

$R^3$ is H, —OH, or halogen;

$R^{21}$ is $R^2H$, halogen, $C_1$-$C_4$ straight or branched alkyl, $C_3$-$C_5$ cycloalkyl wherein the $C_3$-$C_5$ cycloalkyl optionally includes an oxygen or nitrogen heteroatom;

$R^{22}$ is H, halogen, or $C_1$-$C_2$ alkyl;

$R^{24}$ is H, $C_1$-$C_4$ straight or branched alkyl, —($C_1$-$C_4$ alkyl)$_t$-OH,
—($C_1$-$C_4$ alkyl)$_t$-O$_t$—($C_3$-$C_5$ cycloalkyl), or
—($C_1$-$C_4$ alkyl)$_t$-O—($C_1$-$C_4$ straight or branched alkyl) wherein:
t is 0 or 1;
the $C_3$-$C_5$ cycloalkyl optionally includes an oxygen or nitrogen heteroatom;

$L^1$ is $CR^{23}$ or N;
$L^2$ is CH or N;
at least one of $L^1$ or $L^2$ is N; and
$R^{23}$ is H or $C_1$-$C_4$ straight or branched alkyl.

In some aspects of Structure (IX), $R^{24}$ is $C_1$-$C_4$ straight or branched alkyl or —($C_1$-$C_4$ alkyl)$_t$-O—($C_1$-$C_4$ straight or branched alkyl) wherein t is 0 or 1.

In some aspects of Structure (IX), $R^{21}$ is halogen, $C_1$-$C_4$ straight or branched alkyl, $C_3$-$C_5$ cycloalkyl wherein the $C_3$-$C_5$ cycloalkyl optionally includes an oxygen or nitrogen heteroatom, —S(O)$_u$—($C_1$-$C_4$ straight or branched alkyl) wherein u is 0 or 2, or —S(O)$_u$—($C_3$-$C_5$ cycloalkyl) wherein u is 0 or 2;

In some aspects of Structure (IX), $R^3$ is H or halogen.

In some aspects of Structure (IX), $R^1$ is halogen, —CN or $C_1$-$C_2$ haloalkyl.

In some aspects of Structure (IX), both $L^1$ and $L^2$ are N.

In some aspects of Structure (IX), $R^{21}$ is $C_1$-$C_2$ alkyl or $C_3$-$C_5$ cycloalkyl and $R^{22}$ is $C_1$-$C_2$ alkyl.

In some aspects of Structure (IX), $R^{21}$ is $C_3$-$C_5$ cycloalkyl and $R^{22}$ is $C_1$-$C_2$ alkyl.

In some aspects of Structure (IX), $R^{24}$ is —($C_1$-$C_2$ alkyl)$_t$-O—($C_1$-$C_2$ alkyl) wherein t is 0 or 1.

In some aspects of Structure (IX), $R^{21}$ is $C_3$-$C_5$ cycloalkyl, $R^{22}$ is $C_1$-$C_2$ alkyl and $R^{24}$ is $C_1$-$C_2$ alkyl.

In some aspects of Structure (IX), $R^{21}$ is cyclobutyl, $R^{22}$ is $C_1$-$C_2$ alkyl and $R^{24}$ is $C_1$-$C_2$ alkyl.

In some aspects of Structure (IX), $R^{21}$ is cyclobutyl.

In some aspects of Structure (IX), $R^3$ is H or F.

In some aspects of Structure (IX), $R^1$ is —CN.

In some aspects of Structure (IX), $R^1$ is —CF$_3$.

In some aspects of Structure (IX), $R^{22}$ is H, methyl or ethyl.

In some aspects of Structure (IX), $R^{22}$ is H.

In some aspects of Structure (IX), $R^{22}$ is methyl.

In some aspects of Structure (IX), $R^1$ is —CN, each $R^2$ is H, $R^3$ is H or F, $R^{21}$ is $C_3$-$C_4$ cycloalkyl, $R^{22}$ is methyl, $L^1$ and $L^2$ are N, and $R^{24}$ is methyl, ethyl, hydroxymethyl, methoxymethyl, 2-methoxyethyl.

In some aspects of Structure (IX), $R^1$ is —CN, each $R^2$ is H, $R^3$ is H or F, $R^{21}$ is $C_3$-$C_4$ cycloalkyl, $R^{22}$ is methyl, $L^1$ and $L^2$ are N, and $R^{24}$ is methoxy or ethoxy.

In some aspects of Structure (IX), $R^1$ is —CN, each $R^2$ is H, $R^3$ is H or F, $R^{21}$ is $C_3$-$C_4$ cycloalkyl, $R^{22}$ is methyl, $L^1$ is CH, $L^2$ is N, and $R^{24}$ is methyl, ethyl, hydroxymethyl, methoxymethyl, or 2-methoxyethyl.

In some aspects of Structure (IX), $R^1$ is —CN, each $R^2$ is H, $R^3$ is H or F, $R^{21}$ is $C_3$-$C_4$ cycloalkyl, $R^{22}$ is methyl, $L^1$ is N, $L^2$ is CH, and $R^{24}$ is methyl, ethyl, hydroxymethyl, methoxymethyl, or 2-methoxyethyl.

In some aspects of Structure (IX), compounds have a structure selected from the group consisting of:

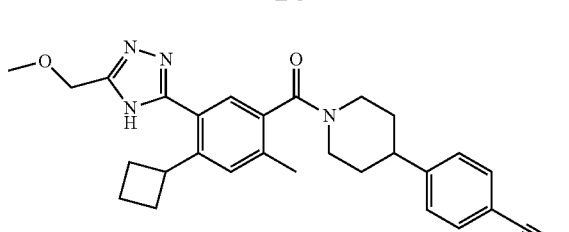

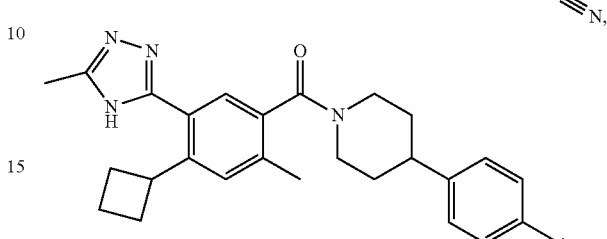

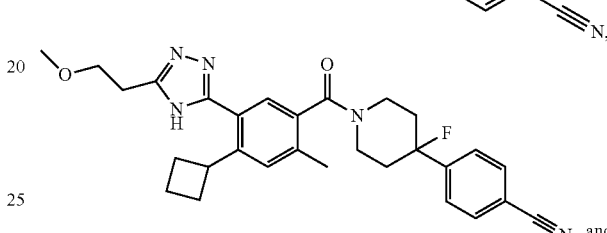

and

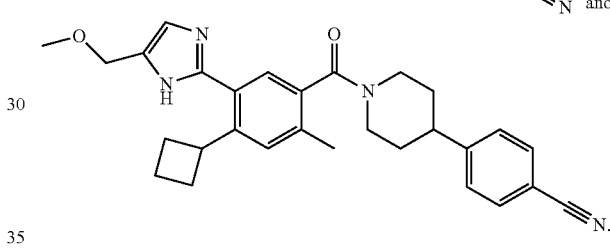

In various aspects, compounds of Structure (X) are provided:

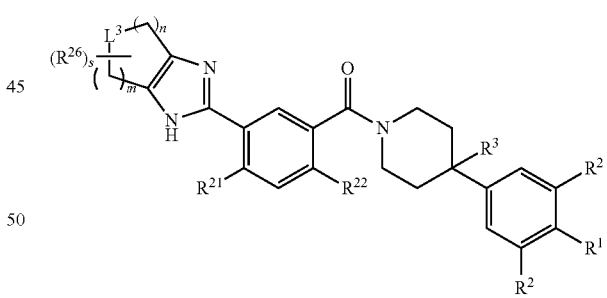

X or a pharmaceutically acceptable salt thereof, wherein:

$R^1$ is H, —CN, halogen, $C_1$-$C_4$ straight or branched alkyl, —O—($C_3$-$C_5$ cycloalkyl), —O—($C_1$-$C_4$ straight or branched alkyl) wherein:
the $C_3$-$C_5$ cycloalkyl optionally includes an oxygen or nitrogen heteroatom; and
when $R^1$ is not H, —CN or halogen, it is optionally substituted with one or more halogens;

each $R^2$ is independently hydrogen, halogen or $C_1$-$C_4$ straight or branched alkyl;

$R^3$ is H, —OH or halogen;

$L^3$ is $C(R^{60})_2$, O or $NR^{50}$;

each $R^{60}$ is independently H, —OH, —CN, —O$_t$—(C$_3$-C$_5$ cycloalkyl), —O—(C$_1$-C$_4$ straight or branched alkyl), or —C(O)—N(R$^{601}$)$_2$ wherein:
t is 0 or 1, and
the C$_3$-C$_5$ cycloalkyl optionally includes an oxygen or nitrogen heteroatom;
each $R^{50}$ is independently H, —C(O)—O$_t$—(C$_1$-C$_4$ straight or branched alkyl), —C(O)—O$_t$—(C$_3$-C$_5$ cyclic alkyl), —C$_3$-C$_5$ cyclic alkyl optionally containing an oxygen or nitrogen heteroatom, —C(O)—N (R$^{501}$)$_2$, C$_1$-C$_4$ straight or branched alkyl wherein:
t is 0 or 1, and
the C$_3$-C$_5$ cycloalkyl optionally includes an oxygen or nitrogen heteroatom;
n is 1, 2 or 3;
m is 1 or 2;
$R^{21}$ is H, halogen, C$_1$-C$_4$ straight or branched alkyl, C$_3$-C$_5$ cycloalkyl wherein the C$_3$-C$_5$ cycloalkyl optionally includes an oxygen or nitrogen heteroatom
$R^{22}$ is H, halogen, C$_1$-C$_2$ alkyl;
each $R^{26}$ is independently —OH, —CN, halogen, C$_1$-C$_4$ straight or branched alkyl, —(C$_1$-C$_4$ alkyl)$_t$-O$_t$—(C$_3$-C$_5$ cycloalkyl), —(C$_1$-C$_4$ alkyl)$_t$-O—(C$_1$-C$_4$ straight or branched alkyl), —C(O)—O$_t$—(C$_1$-C$_4$ alkyl), or —C(O)—N(R$^{501}$)$_2$ wherein:
t is 0 or 1, and
the C$_3$-C$_5$ cycloalkyl optionally includes an oxygen or nitrogen heteroatom;
s is 0, 1 or 2;
each $R^{601}$ and $R^{501}$ is independently H or C$_1$-C$_4$ straight or branched alkyl; and
wherein two of $R^{26}$, $R^{60}$, $R^{50}$, $R^{501}$ and $R^{601}$ optionally join to form a ring wherein the two of $R^{26}$, $R^{60}$, $R^{50}$, $R^{501}$ and $R^{601}$ may be two $R^{26}$, two $R^{60}$, two $R^{50}$, two $R^{501}$ or two $R^{601}$.

In some aspects of Structure (X), $R^{21}$ is halogen, C$_1$-C$_4$ straight or branched alkyl or C$_3$-C$_5$ cycloalkyl.
In some aspects of Structure (X), $R^3$ is H or halogen.
In some aspects of Structure (X), $R^1$ is —CN or C$_1$-C$_2$ haloalkyl.
In some aspects of Structure (X), $R^3$ is H or F.
In some aspects of Structure (X), $R^1$ is —CN.
In some aspects of Structure (X), $R^1$ is —CF$_3$.
In some aspects of Structure (X), n is 1.
In some aspects of Structure (X), n is 2.
In some aspects of Structure (X), m is 1
In some aspects of Structure (X), m is 2.
In some aspects of Structure (X), $R^{21}$ is C$_1$-C$_2$ alkyl or C$_3$-C$_5$ cycloalkyl and $R^{22}$ is C$_1$-C$_2$ alkyl.
In some aspects of Structure (X), $R^{21}$ is C$_3$-C$_5$ cycloalkyl and $R^{22}$ is C$_1$-C$_2$ alkyl.
In some aspects of Structure (X), n is 2, m is 1, $L^3$ is —N—C(O)—O—(C$_1$-C$_2$ alkyl).
In some aspects of Structure (X), $L^3$ is NR$^{50}$; $R^{50}$ is C$_1$-C$_2$ alkyl; $R^{21}$ is cyclobutyl; $R^{22}$ is H or methyl; $R^3$ is H; $R^1$ is —CN; m is 2 and n is 1 or 2.
In some aspects of Structure (X), n is 2, m is 1, $L^3$ is O and s is 0.
In some aspects of Structure (X), $R^{22}$ is H, methyl or ethyl.
In some aspects of Structure (X), $R^{22}$ is methyl.
In some aspects of Structure (X), $R^{22}$ is H.
In some aspects of Structure (X), $R^1$ is —CN, each $R^2$ is H, $R^3$ is H or F, $R^{21}$ is C$_3$-C$_4$ cycloalkyl, $R^{22}$ is methyl, n is 2 and $L^3$ is NR$^{50}$ where $R^{50}$ is methyl or ethyl.

In some aspects of Structure (X), $R^1$ is —CN, each $R^2$ is H, $R^3$ is H or F, $R^{21}$ is C$_3$-C$_4$ cycloalkyl, $R^{22}$ is methyl, n is 2 and $L^3$ is O.

In some aspects of Structure (X), the compound has a structure selected from the group consisting of:

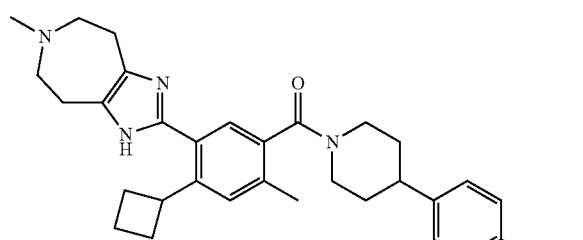

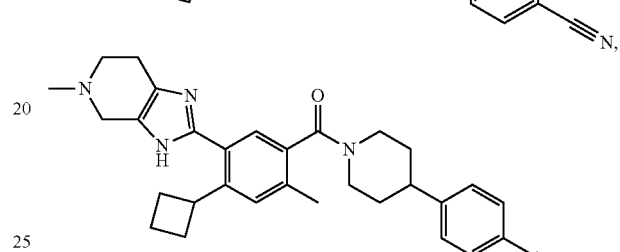
and

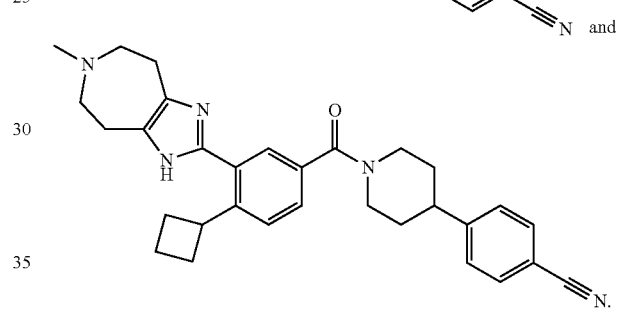

In various aspects, compounds of Structure (XI) are provided:

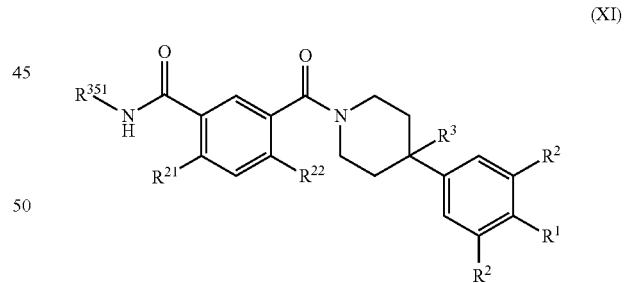

(XI)

or a pharmaceutically acceptable salt thereof, wherein:
$R^1$ is H, —CN, halogen, C$_1$-C$_4$ straight or branched alkyl, —O—(C$_3$-C$_5$ cycloalkyl), —O—(C$_1$-C$_4$ straight or branched alkyl) wherein:
the C$_3$-C$_5$ cycloalkyl optionally includes an oxygen or nitrogen heteroatom; and
when $R^1$ is not H, —CN or halogen, it is optionally substituted with one or more halogens;
each $R^2$ is independently H, halogen or C$_1$-C$_4$ straight or branched alkyl;
$R^3$ is H, —OH, or halogen;
$R^{21}$ is cyclobutyl, azetidin-1-yl, or cyclopropyl;
$R^{22}$ is H, halogen, C$_1$-C$_2$ alkyl; and $R^{351}$ is $C_1$-$C_2$ alkyl or $C_2$—O—($C_1$ or $C_2$ alkyl).

In some aspects of Structure (XI), $R^3$ is H or halogen.

In some aspects of Structure (XI), $R^1$ is halogen, —CN or $C_1$-$C_2$ haloalkyl.

In some aspects of Structure (XI), $R^{21}$ is $C_3$-$C_4$ cycloalkyl and $R^{22}$ is $C_1$-$C_2$ alkyl.

In some aspects of Structure (XI), $R^{21}$ is cyclobutyl and $R^{22}$ is $C_1$-$C_2$ alkyl.

In some aspects of Structure (XI), $R^{21}$ is cyclobutyl.

In some aspects of Structure (XI), $R^3$ is H or F.

In some aspects of Structure (XI), $R^1$ is —CN.

In some aspects of Structure (XI), $R^1$ is —$CF_3$.

In some aspects of Structure (XI), $R^{22}$ is H, methyl or ethyl.

In some aspects of Structure (XI), $R^{22}$ is H.

In some aspects of Structure (XI), $R^{22}$ is methyl.

In some aspects of Structure (XI), $R^1$ is —CN, each $R^2$ is H, $R^3$ is H or F, $R^{21}$ is cyclobutyl, $R^{22}$ is methyl and $R^{351}$ is methyl or ethyl.

In some aspects of Structure (XI), the compound has a structure selected from the group consisting of:

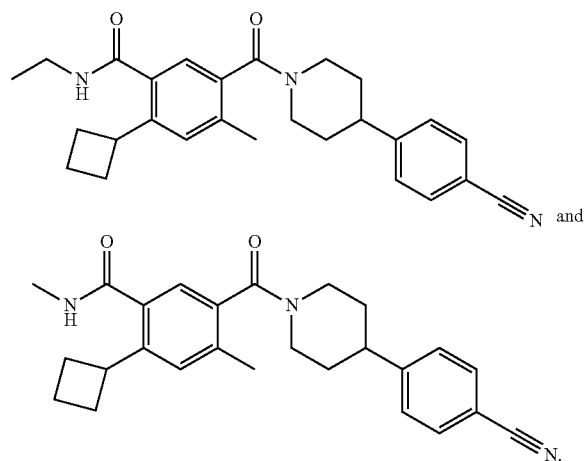

In various aspects, the present disclosure provides pharmaceutical compositions comprising any one of the compounds of Structures (I), (II), (III), (IV), (V), (VI), (VII), (VIII), (IX), (X) or (XI) and a pharmaceutically acceptable carrier, excipient, or diluent.

In various aspects, the present disclosure provides methods of treating a condition characterized by disregulation of a fatty acid synthase function in subject, the method comprising administering to the subject in need of such treatment an effective amount of a compound of any one of the Structures (I), (II), (III), (IV), (V), (VI), (VII), (VIII), (IX), (X) or (XI). In various aspects the condition characterized by disregulation of the fatty acid synthase function is a viral infection or cancer. In various aspects the viral infection is treated using a compound of any one of the Structures (I), (II), (III), (IV), (V), (VI), (VII), (VIII), (IX), (X) or (XI) in combination with one or more additional antiviral treatments. In various aspects the cancer is treated using a compound of any one of the Structures (I), (II), (III), (IV), (V), (VI), (VII), (VIII), (IX), (X) or (XI) in combination with one or more additional cancer treatments. In various aspects, the viral infection is hepatitis C.

BRIEF DESCRIPTION OF THE DRAWINGS

FIG. 1 illustrates a correlation between FASN inhibition and HCV inhibition.

DETAILED DESCRIPTION

The present disclosure addresses the deficiencies in treating conditions characterized by disregulation of the FASN function in a subject, such as viral infection, cancer and metabolic disorders, by providing novel heterocyclic modulators of lipid synthesis.

In certain aspects, the present disclosure provides compositions and methods for treatment of viral infections. In general, the compositions and methods for treatment of viral infections are directed toward modulation of the fatty acid synthesis pathway. The fatty acid synthesis pathway is involved in the replication of viruses into the host cells. The present invention embodies methods for the treatment of viral infection, such as hepatitis C infections, yellow fever infections, and human rhinovirus infections, or any virus that targets the fatty acid synthesis pathway.

In certain aspects, the present disclosure provides compositions and methods for the treatment of cancer. Fatty acid synthase is responsible for conversion of malonyl-CoA into long-chain fatty acids, which is an early reaction in fatty acid biosynthesis. Fatty acid synthase is overexpressed in many cancer cells. Without being bound by any particular theory, it is hypothesized that inhibition of fatty acid synthase expression or fatty acid synthase activity selectivity suppresses proliferation and induces cell death of cancer cells, with little toxicity towards normal cells.

Further, the present disclosure provides compounds and methods for modulating host cell targets that are targeted by viruses. Such modulation of host cell targets can include either activation or inhibition of the host cell targets. Accordingly, compounds that modulate, e.g., inhibit, the activity of a non-viral protein, e.g., a host cell protein, e.g., components of the fatty acid synthesis pathway, can be used as antiviral pharmaceutical agents.

DEFINITIONS

Chemical moieties referred to as univalent chemical moieties (e.g., alkyl, aryl, etc.) also encompass structurally permissible multivalent moieties, as understood by those skilled in the art. For example, while an "alkyl" moiety generally refers to a monovalent radical (e.g., $CH_3CH_2$—), in appropriate circumstances an "alkyl" moiety can also refer to a divalent radical (e.g., —$CH_2CH_2$—, which is equivalent to an "alkylene" group). Similarly, under circumstances where a divalent moiety is required, those skilled in the art will understand that the term "aryl" refers to the corresponding divalent arylene group.

All atoms are understood to have their normal number of valences for bond formation (e.g., 4 for carbon, 3 for N, 2 for O, and 2, 4, or 6 for S, depending on the atom's oxidation state). On occasion a moiety can be defined, for example, as $(A)_aB$, wherein a is 0 or 1. In such instances, when a is 0 the moiety is B and when a is 1 the moiety is AB.

Where a substituent can vary in the number of atoms or groups of the same kind (e.g., alkyl groups can be $C_1$, $C_2$, $C_3$, etc.), the number of repeated atoms or groups can be represented by a range (e.g., $C_1$-$C_6$ alkyl) which includes each and every number in the range and any and all sub ranges. For example, $C_1$-$C_3$ alkyl includes $C_1$, $C_2$, $C_3$, $C_{1-2}$, $C_{1-3}$, and $C_{2-3}$ alkyl.

"Alkanoyl" refers to a carbonyl group with a lower alkyl group as a substituent.

"Alkylamino" refers to an amino group substituted by an alkyl group.

"Alkoxy" refers to an O-atom substituted by an alkyl group as defined herein, for example, methoxy [—OCH$_3$, a C$_1$alkoxy]. The term "C$_{1-6}$ alkoxy" encompasses C$_1$ alkoxy, C$_2$ alkoxy, C$_3$ alkoxy, C$_4$ alkoxy, C$_5$ alkoxy, C$_6$ alkoxy, and any sub-range thereof.

"Alkoxycarbonyl" refers to a carbonyl group with an alkoxy group as a substituent.

"Alkyl," "alkenyl," and "alkynyl," refer to optionally substituted, straight and branched chain aliphatic groups having from 1 to 30 carbon atoms, or preferably from 1 to 15 carbon atoms, or more preferably from 1 to 6 carbon atoms. Examples of alkyl groups include, without limitation, methyl, ethyl, propyl, isopropyl, butyl, tert-butyl, isobutyl, pentyl, hexyl, vinyl, allyl, isobutenyl, ethynyl, and propynyl. The term "heteroalkyl" as used herein contemplates an alkyl with one or more heteroatoms.

"Alkylene" refers to an optionally substituted divalent radical which is a branched or unbranched hydrocarbon fragment containing the specified number of carbon atoms, and having two points of attachment. An example is propylene [—CH$_2$CH$_2$CH$_2$—, a C$_3$alkylene].

"Amino" refers to the group —NH$_2$.

"Aryl" refers to optionally substituted aromatic groups which have at least one ring having a conjugated pi electron system and includes carbocyclic aryl, and biaryl groups, all of which can be optionally substituted. Phenyl and naphthyl groups are preferred carbocyclic aryl groups.

"Aralkyl" or "arylalkyl" refer to alkyl-substituted aryl groups. Examples of aralkyl groups include butylphenyl, propylphenyl, ethylphenyl, methylphenyl, 3,5-dimethylphenyl, tert-butylphenyl.

"Carbamoyl" as used herein contemplates a group of the structure

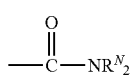

where in R$^N$ is selected from the group consisting of hydrogen, —OH, C$_1$ to C$_{12}$ alkyl, C$_1$ to C$_{12}$ heteroalkyl, alkenyl, alkynyl, cycloalkyl, heterocycle, aryl, heteroaryl, aralkyl, alkoxy, alkoxycarbonyl, alkanoyl, carbamoyl, sulfonyl, sulfonate and sulfonamide.

"Carbonyl" refers to a group of the structure

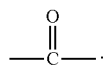

"Cycloalkyl" refers to an optionally substituted ring, which can be saturated or unsaturated and monocyclic, bicyclic, or tricyclic formed entirely from carbon atoms. An example of a cycloalkyl group is the cyclopentenyl group (C$_5$H$_7$—), which is a five carbon (C$_5$) unsaturated cycloalkyl group.

"Heterocycle" refers to an optionally substituted 5- to 7-membered cycloalkyl ring system containing 1, 2 or 3 heteroatoms, which can be the same or different, selected from N, O or S, and optionally containing one double bond.

"Halogen" refers to a chloro, bromo, fluoro or iodo atom radical. The term "halogen" also contemplates terms "halo" or "halide."

"Heteroatom" refers to a non-carbon atom, where boron, nitrogen, oxygen, sulfur and phosphorus are preferred heteroatoms, with nitrogen, oxygen and sulfur being particularly preferred heteroatoms in the compounds of the present disclosure.

"Heteroaryl" refers to optionally substituted aryl groups having from 1 to 9 carbon atoms and the remainder of the atoms are heteroatoms, and includes those heterocyclic systems described in "Handbook of Chemistry and Physics," 49th edition, 1968, R. C. Weast, editor; The Chemical Rubber Co., Cleveland, Ohio. See particularly Section C, Rules for Naming Organic Compounds, B. Fundamental Heterocyclic Systems. Suitable heteroaryls include thienyl, pyrryl, furyl, pyridyl, pyrimidyl, pyrazinyl, pyrazolyl, oxazolyl, isoxazolyl, imidazolyl, thiazolyl, pyranyl, tetrazolyl, pyrrolyl, pyrrolinyl, pyridazinyl, triazolyl, indolyl, isoindolyl, indolizinyl, benzimidazolyl, quinolyl, isoquinolyl, indazolyl, benzotriazolyl, tetrazolopyridazinyl, oxadiazolyl, benzoxazolyl, benzoxadiazolyl, thiadiazolyl, benzothiazolyl, benzothiadiazolyl, and the like.

An "optionally substituted" moiety can be substituted with from one to four, or preferably from one to three, or more preferably one or two non-hydrogen substituents. Unless otherwise specified, when the substituent is on a carbon, it is selected from the group consisting of —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino, none of which are further substituted. Unless otherwise specified, when the substituent is on a nitrogen, it is selected from the group consisting of C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, sulfonyl, sulfonate and sulfonamide none of which are further substituted.

The term "sulfonamide" as used herein contemplates a group having the structure

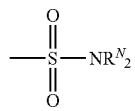

wherein R$^N$ is selected from the group consisting of hydrogen, —OH, C$_1$ to C$_{12}$ alkyl, C$_1$ to C$_{12}$ heteroalkyl, alkenyl, alkynyl, cycloalkyl, heterocycle, aryl, heteroaryl, aralkyl, alkoxy, alkoxycarbonyl, alkanoyl, carbamoyl, substituted sulfonyl, sulfonate and sulfonamide.

The term "sulfonate" as used herein contemplates a group having the structure

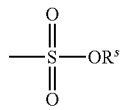

wherein R$^s$ is selected from the group consisting of hydrogen, C$_1$-C$_{10}$ alkyl, C$_2$-C$_{10}$ alkenyl, C$_2$-C$_{10}$ alkynyl, C$_1$-C$_{10}$ alkanoyl, or C$_1$-C$_{10}$ alkoxycarbonyl.

"Sulfonyl" as used herein alone or as part of another group, refers to an $SO_2$ group. The $SO_2$ moiety is optionally substituted.

Compounds of the present disclosure can exist as stereoisomers, wherein asymmetric or chiral centers are present. Stereoisomers are designated (R) or (S) depending on the configuration of substituents around the chiral carbon atom. The terms (R) and (S) used herein are configurations as defined in IUPAC 1974 Recommendations for Section E, Fundamental Stereochemistry, Pure Appl. Chem., (1976), 45: 13-30, hereby incorporated by reference. The present disclosure contemplates various stereoisomers and mixtures thereof and are specifically included within the scope of the present disclosure. Stereoisomers include enantiomers, diastereomers, and mixtures of enantiomers or diastereomers. Individual stereoisomers of compounds of the present disclosure can be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

Also, moieties disclosed herein which exist in multiple tautomeric forms include all such forms encompassed by a given tautomeric structure.

Individual atoms in the disclosed compounds may be any isotope of that element. For example hydrogen may be in the form of deuterium.

"Pharmaceutically acceptable" means approved or approvable by a regulatory agency of the Federal or state government or listed in the U.S. Pharmacopoeia or other generally recognized pharmacopoeia for use in animals, and more particularly in humans. It can be material which is not biologically or otherwise undesirable, i.e., the material can be administered to an individual without causing any undesirable biological effects or interacting in a deleterious manner with any of the components of the composition in which it is contained.

The term "pharmaceutically acceptable salt" of a compound means a salt that is pharmaceutically acceptable and that possesses the desired pharmacological activity of the parent compound. Such salts include, for example, acid addition salts and base addition salts.

"Acid addition salts" according to the present disclosure, are formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like.

"Base addition salts" according to the present disclosure are formed when an acidic proton present in the parent compound either is replaced by a metal ion, e.g., an alkali metal ion, an alkaline earth ion, or an aluminum ion; or coordinates with an organic base. Acceptable organic bases include ethanolamine, diethanolamine, triethanolamine, tromethamine, N-methylglucamine, and the like. Acceptable inorganic bases include aluminum hydroxide, calcium hydroxide, potassium hydroxide, sodium carbonate, sodium hydroxide, and the like. It should be understood that a reference to a pharmaceutically acceptable salt includes the solvent addition forms or crystal forms thereof, particularly solvates or polymorphs. Solvates contain either stoichiometric or non-stoichiometric amounts of a solvent, and are often formed during the process of crystallization. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature can cause a single crystal form to dominate.

The term "treating" includes the administration of the compounds or agents of the present invention to a subject to prevent or delay, to alleviate, or to arrest or inhibit development of the symptoms or conditions associated with fatty acid synthase-associated disorders, e.g., tumor growth associated with cancer. A skilled medical practitioner will know how to use standard methods to determine whether a patient is suffering from a disease associated with activity of fatty acid synthase, e.g., by examining the patient and determining whether the patient is suffering from a disease known to be associated with fatty acid synthase activity or by assaying for fatty acid synthase levels in blood plasma or tissue of the individual suspected of suffering from fatty acid synthase associated disease and comparing fatty acid synthase levels in the blood plasma or tissue of the individual suspected of suffering from a fatty acid synthase assoicated disease fatty acid synthase levels in the blood plasma or tissue of a healthy individual. Increased securin levels are indicative of disease. Accordingly, the present invention provides, inter alia, methods of administering a compound of the present invention to a subject and determining fatty acid synthase activity in the subject. Fatty acid synthase activity in the subject can be determined before and/or after administration of the compound.

A "therapeutically effective amount" or "pharmaceutically effective amount" means the amount that, when administered to a subject, produces effects for which it is administered. For example, a "therapeutically effective amount," when administered to a subject to inhibit fatty acid synthase activity, is sufficient to inhibit fatty acid synthase activity. A "therapeutically effective amount," when administered to a subject for treating a disease, is sufficient to effect treatment for that disease.

Except when noted, the terms "subject" or "patient" are used interchangeably and refer to mammals such as human patients and non-human primates, as well as experimental animals such as rabbits, rats, and mice, and other animals. Accordingly, the term "subject" or "patient" as used herein means any mammalian patient or subject to which the compounds of the invention can be administered. In an exemplary aspect of the present invention, to identify subject patients for treatment according to the methods of the invention, accepted screening methods are employed to determine risk factors associated with a targeted or suspected disease or condition or to determine the status of an existing disease or condition in a subject. These screening methods include, for example, conventional work-ups to determine risk factors that are associated with the targeted or suspected disease or condition. These and other routine methods allow the clinician to select patients in need of therapy using the methods and formulations of the present invention.

FASN Pathway Modulators

One aspect of the present disclosure includes a method of inhibiting viral infection or treating cancer by contacting a cell with an agent that modulates the fatty acid synthesis pathway. This method of inhibiting viral infection or treating cancer can be performed in vitro by contacting virally infected/cancerous cells with an agent that modulates the fatty acid synthesis pathway, or in vivo by administering an agent that modulates the fatty acid synthesis pathway to a subject infected with a virus/having cancer. In one aspect, an agent can be an inhibitor of the fatty acid synthesis pathway.

Examples of inhibitors of the fatty acid synthesis pathway that can be used in the methods and compositions of the present disclosure are described below.

Compounds of Structure (I)

In various aspects, the present disclosure provides for compounds of Structure (I):

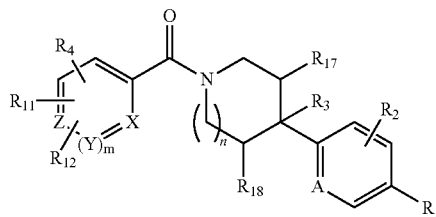

(I)

or a pharmaceutically acceptable salt thereof, wherein:

X, Y, and Z are each independently CR or NW, wherein R is hydrogen or $C_{1-6}$ alkyl and R' is hydrogen, $C_{1-6}$ alkyl, or absent;

A is CH or N;

$R_1$ is hydrogen, cyano, halo, $C_{1-6}$ alkyl, $C_{1-6}$ alkoxy, —C(=O)N($R_{13}$)($R_{14}$), —(CH$_2$)$_q$C(=O)N($R_{13}$)($R_{14}$), CF$_3$, —OCF$_3$, or —S(=O)$_2$R$_{20}$;

q is 0, 1, 2, 3, or 4;

$R_{20}$ is hydrogen or $C_{1-6}$ alkyl, $C_{1-6}$ alkoxy, or —N($R_{13}$)($R_{14}$);

$R_2$ is hydrogen, halo, $C_{1-6}$ alkoxy, $C_{1-6}$ alkyl, or $R_2$ and $R_3$ taken together with the atoms to which they are attached form a 5-membered heterocyclyl;

$R_3$ is hydrogen, hydroxyl, halo, $C_{1-6}$ alkyl, $C_{1-6}$ alkoxy, or $R_2$ and $R_3$ taken together with the atoms to which they are attached form a 5-membered heterocyclyl;

$R_4$ is hydrogen, heteroaryl, heterocyclyl, —C(=O)N($R_5R_6$), —N($R_7$)C(=O)$R_8$, —N($R_9R_{10}$), $C_{1-6}$ alkyl, $C_{1-6}$ alkoxy, —S(=O)$_2$R$_{20}$, or $R_4$ and $R_{11}$ taken together with the atoms to which they are attached join together to form a heteroaryl;

$R_{11}$ is hydrogen, halo, cyano, $C_{1-6}$ alkyl, $C_{1-6}$ alkoxy, —N($R_{13}R_{14}$), CF$_3$, —OCF$_3$, —S(=O)$_2$R$_{20}$, $R_4$ and $R_{11}$ taken together with the atoms to which they are attached join together to form a heteroaryl, or $R_{11}$ and $R_{12}$ taken together with the atoms to which they are attached join together to form a heteroaryl;

$R_{12}$ is hydrogen, halo, cyano, $C_{1-6}$ alkyl, $C_{1-6}$ alkoxy, —N($R_{13}R_{14}$), CF$_3$, —OCF$_3$, —S(=O)$_2$R$_{20}$, or $R_{11}$ and $R_{12}$ taken together with the atoms to which they are attached join together to form a heteroaryl;

$R_5$, $R_6$, $R_7$, $R_8$, $R_9$ $R_{10}$, $R_{13}$, and $R_{14}$ are each independently hydrogen, $C_{1-6}$ alkyl, cycloalkyl, aryl, heterocyclyl, heteroaryl, hydroxyalkyl, alkylamino, —N($R_{15}R_{16}$), Or —S(=O)$_2$R$_{20}$;

$R_{15}$ and $R_{16}$ are each independently hydrogen, $C_{1-6}$ alkyl, cycloalkyl, aryl, heterocyclyl, heteroaryl, or alkylamino;

$R_{17}$ and $R_{18}$ are each independently hydrogen or alkyl or can optionally join together to form a bond;

n is 1 or 2; and m is 0 or 1.

In certain aspects of Structure (I), $R_3$ is F.

In certain aspects of Structure (I), A is CH.

In certain aspects of Structure (I), A is N.

In certain aspects of Structure (I), X, Y, and Z are NR'.

In certain aspects of Structure (I), $R_4$ is heteroaryl, heterocyclyl, —C(=O)N($R_5R_6$), —N($R_7$)C(=O)$R_8$, —N($R_9R_{10}$), $C_{1-6}$ alkyl, $C_{1-6}$ alkoxy, or $R_4$ and $R_{11}$ taken together with the atoms to which they are attached join together to form a heteroaryl.

In certain aspects of Structure (I), $R_5$ is hydrogen and $R_6$ is aryl or heteroaryl.

In certain aspects, the compounds of Structure (I) have one of the following Structures (I-A) or (I-B):

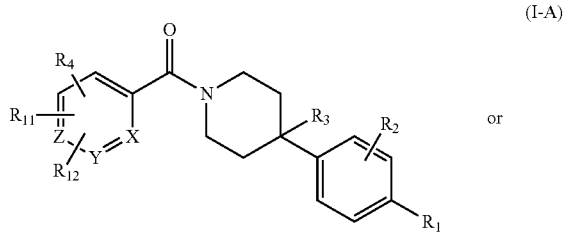

(I-A)

or

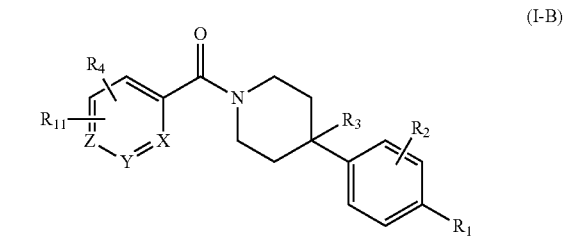

(I-B)

or a pharmaceutically acceptable salt thereof, wherein:

X, Y, and Z are each independently CR or NR', wherein R is hydrogen or $C_{1-6}$ alkyl and R' is hydrogen, $C_{1-6}$ alkyl, or absent;

$R_1$ is hydrogen, cyano, halo, $C_{1-6}$ alkyl, $C_{1-6}$ alkoxy, —C(=O)N($R_{13}$)($R_{14}$), —(CH$_2$)$_q$C(=O)N($R_{13}$)($R_{14}$), CF$_3$, —OCF$_3$, or —S(=O)$_2$R$_{20}$;

q is 0, 1, 2, 3, or 4;

$R_{20}$ is hydrogen or $C_{1-6}$ alkyl, $C_{1-6}$ alkoxy, or —N($R_{13}$)($R_{14}$);

$R_2$ is hydrogen, halo, $C_{1-6}$ alkoxy, $C_{1-6}$ alkyl, or $R_2$ and $R_3$ taken together with the atoms to which they are attached form a 5-membered heterocyclyl;

$R_3$ is hydrogen, hydroxyl, halo, $C_{1-6}$ alkyl, $C_{1-6}$ alkoxy, or $R_2$ and $R_3$ taken together with the atoms to which they are attached form a 5-membered heterocyclyl;

$R_4$ is hydrogen, heteroaryl, heterocyclyl, —C(=O)N($R_5R_6$), —N($R_7$)C(=O)$R_8$, —N($R_9R_{10}$); $C_{1-6}$ alkyl, $C_{1-6}$ alkoxy, —S(=O)$_2R_{20}$, or $R_4$ and $R_{11}$ taken together with the atoms to which they are attached join together to form a heteroaryl;

$R_{11}$ is hydrogen, halo, cyano, $C_{1-6}$ alkyl, $C_{1-6}$ alkoxy, —N($R_{13}R_{14}$), CF$_3$, —OCF$_3$, —S(=O)$_2R_{20}$, $R_4$ and $R_{11}$ taken together with the atoms to which they are attached join together to form a heteroaryl, or $R_{11}$ and $R_{12}$ taken together with the atoms to which they are attached join together to form a heteroaryl;

$R_{12}$ is hydrogen, halo, cyano, $C_{1-6}$ alkyl, $C_{1-6}$ alkoxy, —N($R_{13}R_{14}$), CF$_3$, —OCF$_3$, —S(=O)$_2R_{20}$, or $R_{11}$ and $R_{12}$ taken together with the atoms to which they are attached join together to form a heteroaryl;

$R_5$, $R_6$, $R_7$, $R_8$, $R_9$ $R_{10}$, $R_{13}$, and $R_{14}$ are each independently hydrogen, $C_{1-6}$ alkyl, cycloalkyl, aryl, heterocyclyl, heteroaryl, hydroxyalkyl, alkylamino, —N($R_{15}R_{16}$), or —S(=O)$_2R_{20}$;

$R_{15}$ and $R_{16}$ are each independently hydrogen, $C_{1-6}$ alkyl, cycloalkyl, aryl, heterocyclyl, heteroaryl, or alkylamino; and $R_{17}$ and $R_{18}$ are each independently hydrogen or alkyl or can optionally join together to form a bond.

In certain aspects, the compounds of Structure (I) have one of the following Structures (I-C) or (I-D):

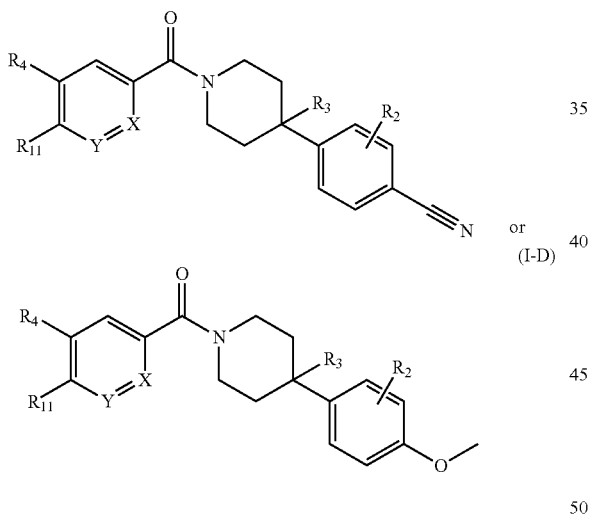

or a pharmaceutically acceptable salt thereof, wherein:

X, Y, and Z are each independently CR or NR', wherein R is hydrogen or $C_{1-6}$ alkyl and R' is hydrogen, $C_{1-6}$ alkyl, or absent;

$R_2$ is hydrogen, halo, $C_{1-6}$ alkoxy, $C_{1-6}$ alkyl, or $R_2$ and $R_3$ taken together with the atoms to which they are attached form a 5-membered heterocyclyl;

$R_3$ is hydrogen, hydroxyl, halo, $C_{1-6}$ alkyl, $C_{1-6}$ alkoxy, or $R_2$ and $R_3$ taken together with the atoms to which they are attached form a 5-membered heterocyclyl;

$R_4$ is hydrogen, heteroaryl, heterocyclyl, —C(=O)N($R_5R_6$), —N($R_7$)C(=O)$R_8$, —N($R_9R_{10}$), $C_{1-6}$ alkyl, $C_{1-6}$ alkoxy, —S(=O)$_2R_{20}$, or $R_4$ and $R_{11}$ taken together with the atoms to which they are attached join together to form a heteroaryl;

$R_{20}$ is hydrogen or $C_{1-6}$ alkyl, $C_{1-6}$ alkoxy, or —N($R_{13}$)($R_{14}$);

$R_{11}$ is hydrogen, halo, cyano, $C_{1-6}$ alkyl, $C_{1-6}$ alkoxy, —N($R_{13}R_{14}$), CF$_3$, —OCF$_3$, —S(=O)$_2R_{20}$, or $R_4$ and $R_{11}$ taken together with the atoms to which they are attached join together to form a heteroaryl;

$R_5$, $R_6$, $R_7$, $R_8$, $R_9$, and $R_{10}$ are each independently H, $C_{1-6}$ alkyl, cycloalkyl, aryl, heterocyclyl, heteroaryl, alkylamino, or —N($R_{15}R_{16}$); and $R_{15}$ and $R_{16}$ are each independently H, $C_{1-6}$ alkyl, cycloalkyl, aryl, heterocyclyl, heteroaryl, or alkylamino.

In certain aspects, the compounds of Structure (I) have one of the following Structures (I-E), (I-F), (I-G), (I-H):

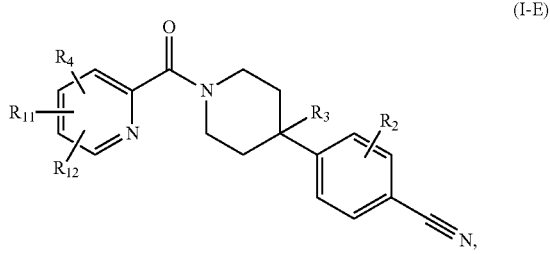

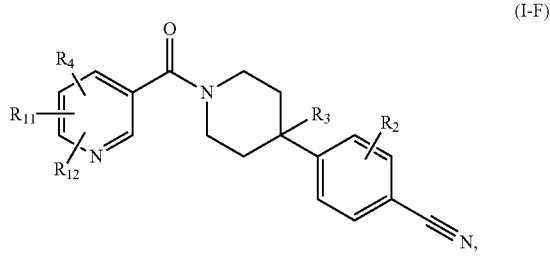

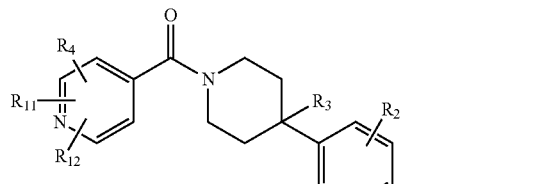

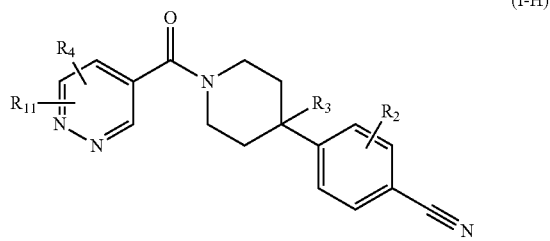

or a pharmaceutically acceptable salt thereof, wherein:

$R_2$ is hydrogen, halo, $C_{1-6}$ alkoxy, $C_{1-6}$ alkyl, or $R_2$ and $R_3$ taken together with the atoms to which they are attached form a 5-membered heterocyclyl;

$R_3$ is hydrogen, hydroxyl, halo, $C_{1-6}$ alkyl, $C_{1-6}$ alkoxy, or $R_2$ and $R_3$ taken together with the atoms to which they are attached form a 5-membered heterocyclyl;

$R_4$ is hydrogen, heteroaryl, heterocyclyl, —C(=O)N($R_5R_6$), —N($R_7$)C(=O)$R_8$, —N($R_9R_{10}$), $C_{1-6}$ alkyl, $C_{1-6}$ alkoxy, —S(=O)$_2R_{20}$, or $R_4$ and $R_{11}$ taken together with the atoms to which they are attached join together to form a heteroaryl;

$R_{20}$ is hydrogen or $C_{1-6}$ alkyl, $C_{1-6}$ alkoxy, or $-N(R_{13})(R_{14})$;

$R_{11}$ is hydrogen, halo, cyano, $C_{1-6}$ alkyl, $C_{1-6}$ alkoxy, $-N(R_{13}R_{14})$, $CF_3$, $-OCF_3$, $-S(=O)_2R_{20}$, $R_4$ and $R_{11}$ taken together with the atoms to which they are attached join together to form a heteroaryl, or $R_{11}$ and $R_{12}$ taken together with the atoms to which they are attached join together to form a heteroaryl;

$R_{12}$ is hydrogen, halo, cyano, $C_{1-6}$ alkyl, $C_{1-6}$ alkoxy, $-N(R_{13}R_{14})$, $CF_3$, $-OCF_3$, $-S(=O)_2R_{20}$, or $R_{11}$ and $R_{12}$ taken together with the atoms to which they are attached join together to form a heteroaryl;

$R_5$, $R_6$, $R_7$, $R_8$, $R_9$, $R_{10}$, $R_{13}$, and $R_{14}$ are each independently H, $C_{1-6}$ alkyl, cycloalkyl, aryl, heterocyclyl, heteroaryl, alkylamino, or $-N(R_{15}R_{16})$; and $R_{15}$ and $R_{16}$ are each independently H, $C_{1-6}$ alkyl, cycloalkyl, aryl, heterocyclyl, heteroaryl, or alkylamino.

In certain aspects, the compounds of Structure (I) have one of the following Structures (I-I), (I-J), or (I-K):

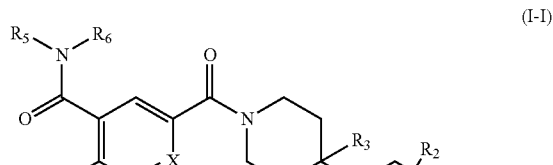

(I-I)

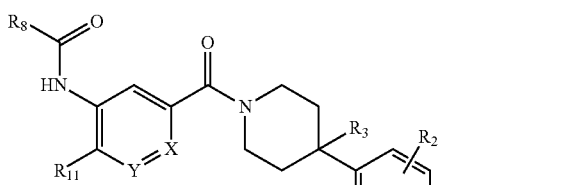

(I-J)

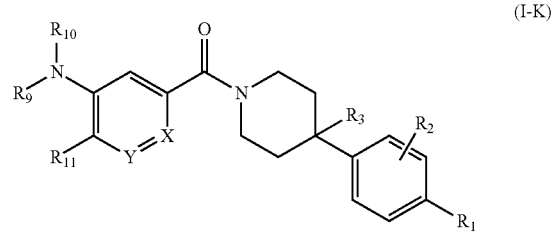

(I-K)

or a pharmaceutically acceptable salt thereof, wherein:

X and Y are each independently CR or NR', wherein R is H or $C_{1-6}$ alkyl and R' is H, $C_{1-6}$ alkyl, or absent;

$R_1$ is hydrogen, cyano, halo, $C_{1-6}$ alkyl, $C_{1-6}$ alkoxy, $-C(=O)N(R_{13})(R_{14})$, $(CH_2)_qC(=O)N(R_{13})(R_{14})$, $CF_3$, $-OCF_3$, or $-S(=O)_2R_{20}$;

q is 0, 1, 2, 3, or 4;

$R_{20}$ is hydrogen or $C_{1-6}$ alkyl, $C_{1-6}$ alkoxy, or $-N(R_{13})(R_{14})$;

$R_2$ is hydrogen, halo, $C_{1-6}$ alkoxy, $C_{1-6}$ alkyl, or $R_2$ and $R_3$ taken together with the atoms to which they are attached form a 5-membered heterocyclyl;

$R_3$ is hydrogen, hydroxyl, halo, $C_{1-6}$ alkyl, $C_{1-6}$ alkoxy, or $R_2$ and $R_3$ taken together with the atoms to which they are attached form a 5-membered heterocyclyl;

$R_{11}$ is hydrogen, halo, cyano, $C_{1-6}$ alkyl, $C_{1-6}$ alkoxy, $-N(R_{13}R_{14})$, $CF_3$, $-OCF_3$, or $-S(=O)_2R_{20}$;

$R_5$, $R_6$, $R_7$, $R_8$, $R_9$, and $R_{10}$ are each independently H, $C_{1-6}$ alkyl, cycloalkyl, aryl, heterocyclyl, heteroaryl, alkylamino, or $-N(R_{15}R_{16})$; and $R_{15}$ and $R_{16}$ are each independently H, $C_{1-6}$ alkyl, cycloalkyl, aryl, heterocyclyl, heteroaryl, or alkylamino.

In certain aspects, the compounds of Structure (I) have one of the following Structures (I-L) or (I-M):

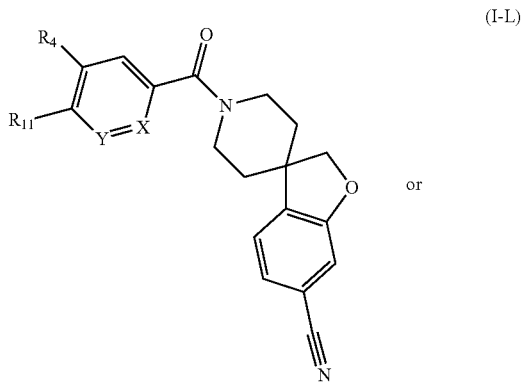

(I-L)

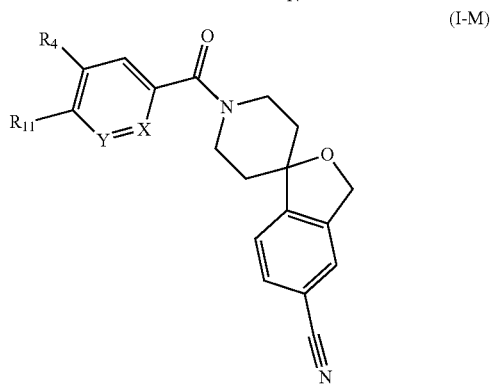

(I-M)

or a pharmaceutically acceptable salt thereof, wherein:

X and Y are each independently CR or NR', wherein R is H or $C_{1-6}$ alkyl and R' is H, $C_{1-6}$ alkyl, or absent;

$R_4$ is hydrogen, heteroaryl, heterocyclyl, $-C(=O)N(R_5R_6)$, $-N(R_7)C(=O)R_8$, $-N(R_9R_{10})$, $C_{1-6}$ alkyl, $C_{1-6}$ alkoxy, $-S(=O)_2R_{20}$, or $R_4$ and $R_{11}$ taken together with the atoms to which they are attached join together to form a heteroaryl;

$R_{20}$ is hydrogen or $C_{1-6}$ alkyl, $C_{1-6}$ alkoxy, or $-N(R_{13})(R_{14})$;

$R_{11}$ is hydrogen, halo, cyano, $C_{1-6}$ alkyl, $C_{1-6}$ alkoxy, $-N(R_{13}R_{14})$, $CF_3$, $-OCF_3$, $-S(=O)_2R_{20}$, or $R_4$ and $R_{11}$ taken together with the atoms to which they are attached join together to form a heteroaryl;

$R_5$, $R_6$, $R_7$, $R_8$, $R_9$, and $R_{10}$ are each independently H, $C_{1-6}$ alkyl, cycloalkyl, aryl, heterocyclyl, heteroaryl, alkylamino, or $-N(R_{15}R_{16})$; and $R_{15}$ and $R_{16}$ are each independently H, $C_{1-6}$ alkyl, cycloalkyl, aryl, heterocyclyl, heteroaryl, or alkylamino.

In certain aspects, the compounds of Structure (I) have one of the following Structures (I-N) or (I-O):

(I-N)

(I-O)

or a pharmaceutically acceptable salt thereof.

In certain aspects, the compounds of Structure (I) have the following Structure (I-P):

(I-P)

or a pharmaceutically acceptable salt thereof, wherein:

$R_2$ is hydrogen, halo, $C_{1-6}$ alkoxy, $C_{1-6}$ alkyl, or $R_2$ and $R_3$ taken together with the atoms to which they are attached form a 5-membered heterocyclyl;

$R_3$ is hydrogen, hydroxyl, halo, $C_{1-6}$ alkyl, $C_{1-6}$ alkoxy, or $R_2$ and $R_3$ taken together with the atoms to which they are attached form a 5-membered heterocyclyl;

$R_4$ is hydrogen, heteroaryl, heterocyclyl, —C(=O)N($R_5R_6$), —N($R_7$)C(=O)$R_8$, —N($R_9R_{10}$), $C_{1-6}$ alkyl, $C_{1-6}$ alkoxy, —S(=O)$_2R_{20}$, or $R_4$ and $R_{11}$ taken together with the atoms to which they are attached join together to form a heteroaryl;

$R_{20}$ is hydrogen or $C_{1-6}$ alkyl, $C_{1-6}$ alkoxy, or —N($R_{13}$)($R_{14}$);

$R_{11}$ is hydrogen, halo, cyano, $C_{1-6}$ alkyl, $C_{1-6}$ alkoxy, —N($R_{13}R_{14}$), $CF_3$, —$OCF_3$, —S(=O)$_2R_{20}$, $R_4$ and $R_{11}$ taken together with the atoms to which they are attached join together to form a heteroaryl, or $R_{11}$ and $R_{12}$ taken together with the atoms to which they are attached join together to form a heteroaryl;

$R_{12}$ is hydrogen, halo, cyano, $C_{1-6}$ alkyl, $C_{1-6}$ alkoxy, —N($R_{13}R_{14}$), $CF_3$, —$OCF_3$, —S(=O)$_2R_{20}$, or $R_{11}$ and $R_{12}$ taken together with the atoms to which they are attached join together to form a heteroaryl;

$R_5$, $R_6$, $R_7$, $R_8$, $R_9$, $R_{10}$, $R_{13}$, and $R_{14}$ are each independently H, $C_{1-6}$ alkyl, cycloalkyl, aryl, heterocyclyl, heteroaryl, alkylamino, or —N($R_{15}R_{16}$); and $R_{15}$ and $R_{16}$ are each independently H, $C_{1-6}$ alkyl, cycloalkyl, aryl, heterocyclyl, heteroaryl, or alkylamino.

In certain aspects, the compounds of Structure (I) have one of the following Structures (I-Q), (I-R), or (I-S):

(I-Q)

(I-R)

(I-S)

or a pharmaceutically acceptable salt thereof.

In certain aspects, the compounds of Structure (I) have the following Structure (I-T):

(I-T)

or a pharmaceutically acceptable salt thereof, wherein:

X, Y, and Z are each independently CR or NR', wherein R is H or $C_{1-6}$ alkyl and R' is H, $C_{1-6}$ alkyl, or absent;

$R_1$ is hydrogen, cyano, halo, $C_{1-6}$ alkyl, $C_{1-6}$ alkoxy, —C(=O)N($R_{13}$)($R_{14}$), —(CH$_2$)$_q$C(=O)N($R_{13}$)($R_{14}$), CF$_3$, —OCF$_3$, or —S(=O)$_2$R$_{20}$;

q is 0, 1, 2, 3, or 4;

$R_{20}$ is hydrogen or $C_{1-6}$ alkyl, $C_{1-6}$ alkoxy, or —N($R_{13}$)($R_{14}$);

$R_2$ is hydrogen, halo, $C_{1-6}$ alkoxy, $C_{1-6}$ alkyl, or $R_2$ and $R_3$ taken together with the atoms to which they are attached form a 5-membered heterocyclyl;

$R_3$ is hydrogen, hydroxyl, halo, $C_{1-6}$ alkyl, $C_{1-6}$ alkoxy, or $R_2$ and $R_3$ taken together with the atoms to which they are attached form a 5-membered heterocyclyl;

$R_4$ is hydrogen, heteroaryl, heterocyclyl, —C(=O)N($R_5R_6$), —N($R_7$)C(=O)$R_8$, —N($R_9R_{10}$), $C_{1-6}$ alkyl, $C_{1-6}$ alkoxy, —S(=O)$_2$R$_{20}$, or $R_4$ and $R_{11}$ taken together with the atoms to which they are attached join together to form a heteroaryl;

$R_{11}$ is hydrogen, halo, cyano, $C_{1-6}$ alkyl, $C_{1-6}$ alkoxy, —N($R_{13}R_{14}$), CF$_3$, —OCF$_3$, —S(=O)$_2$R$_{20}$, $R_4$ and $R_{11}$ taken together with the atoms to which they are attached join together to form a heteroaryl, or $R_{11}$ and $R_{12}$ taken together with the atoms to which they are attached join together to form a heteroaryl;

$R_{12}$ is hydrogen, halo, cyano, $C_{1-6}$ alkyl, $C_{1-6}$ alkoxy, —N($R_{13}R_{14}$), CF$_3$, —OCF$_3$, —S(=O)$_2$R$_{20}$, or $R_{11}$ and $R_{12}$ taken together with the atoms to which they are attached join together to form a heteroaryl;

$R_5$, $R_6$, $R_7$, $R_8$, $R_9$, $R_{10}$, $R_{13}$, and $R_{14}$ are each independently H, $C_{1-6}$ alkyl, cycloalkyl, aryl, heterocyclyl, heteroaryl, alkylamino, or —N($R_{15}R_{16}$); and $R_{15}$ and $R_{16}$ are each independently H, $C_{1-6}$ alkyl, cycloalkyl, aryl, heterocyclyl, heteroaryl, or alkylamino.

In certain aspects, the compounds of Structure (I) have the following Structure (I-U):

(I-U)

or a pharmaceutically acceptable salt thereof.

In certain aspects, the compounds of Structure (I) have one of the following Structures (I-V):

(I-V)

or a pharmaceutically acceptable salt thereof, wherein:

X, Y, and Z are each independently CR or NR', wherein R is H or $C_{1-6}$ alkyl and R' is H, $C_{1-6}$ alkyl, or absent;

$R_1$ is hydrogen, cyano, halo, $C_{1-6}$ alkyl, $C_{1-6}$ alkoxy, —C(=O)N($R_{13}$)($R_{14}$), —(CH$_2$)$_q$C(=O)N($R_{13}$)($R_{14}$), CF$_3$, —OCF$_3$, or —S(=O)$_2$R$_{20}$;

q is 0, 1, 2, 3, or 4;

$R_{20}$ is hydrogen or $C_{1-6}$ alkyl, $C_{1-6}$ alkoxy, or —N($R_{13}$)($R_{14}$);

$R_2$ is hydrogen, halo, $C_{1-6}$ alkoxy, $C_{1-6}$ alkyl, or $R_2$ and $R_3$ taken together with the atoms to which they are attached form a 5-membered heterocyclyl;

$R_3$ is hydrogen, hydroxyl, halo, $C_{1-6}$ alkyl, $C_{1-6}$ alkoxy, or $R_2$ and $R_3$ taken together with the atoms to which they are attached form a 5-membered heterocyclyl;

$R_4$ is hydrogen, heteroaryl, heterocyclyl, —C(=O)N($R_5R_6$), —N($R_7$)C(=O)$R_8$, —N($R_9R_{10}$), $C_{1-6}$ alkyl, $C_{1-6}$ alkoxy, —S(=O)$_2$R$_{20}$, or $R_4$ and $R_{11}$ taken together with the atoms to which they are attached join together to form a heteroaryl;

$R_{11}$ is hydrogen, halo, cyano, $C_{1-6}$ alkyl, $C_{1-6}$ alkoxy, —N($R_{13}R_{14}$), CF$_3$, —OCF$_3$, —S(=O)$_2$R$_{20}$, $R_4$ and $R_{11}$ taken together with the atoms to which they are attached join together to form a heteroaryl, or $R_{11}$ and $R_{12}$ taken together with the atoms to which they are attached join together to form a heteroaryl;

$R_{12}$ is hydrogen, halo, cyano, $C_{1-6}$ alkyl, $C_{1-6}$ alkoxy, —N($R_{13}R_{14}$), CF$_3$, —OCF$_3$, —S(=O)$_2$R$_{20}$, or $R_{11}$ and $R_{12}$ taken together with the atoms to which they are attached join together to form a heteroaryl;

$R_5$, $R_6$, $R_7$, $R_8$, $R_9$, $R_{10}$, $R_{13}$, and $R_{14}$ are each independently H, $C_{1-6}$ alkyl, cycloalkyl, aryl, heterocyclyl, heteroaryl, alkylamino, or —N($R_{15}R_{16}$); and $R_{15}$ and $R_{16}$ are each independently H, $C_{1-6}$ alkyl, cycloalkyl, aryl, heterocyclyl, heteroaryl, or alkylamino.

In certain aspects, the compound of Structure (I) has the following Structure (I-W):

(I-W)

or a pharmaceutically acceptable salt thereof.

In certain aspects, the compounds of Structure (I) have one of the following Structures (I-X), (I-Y), (I-Z), (I-AA), (I-AB), (I-AC), (I-AD), (I-AF), (I-AG), or (I-AH):

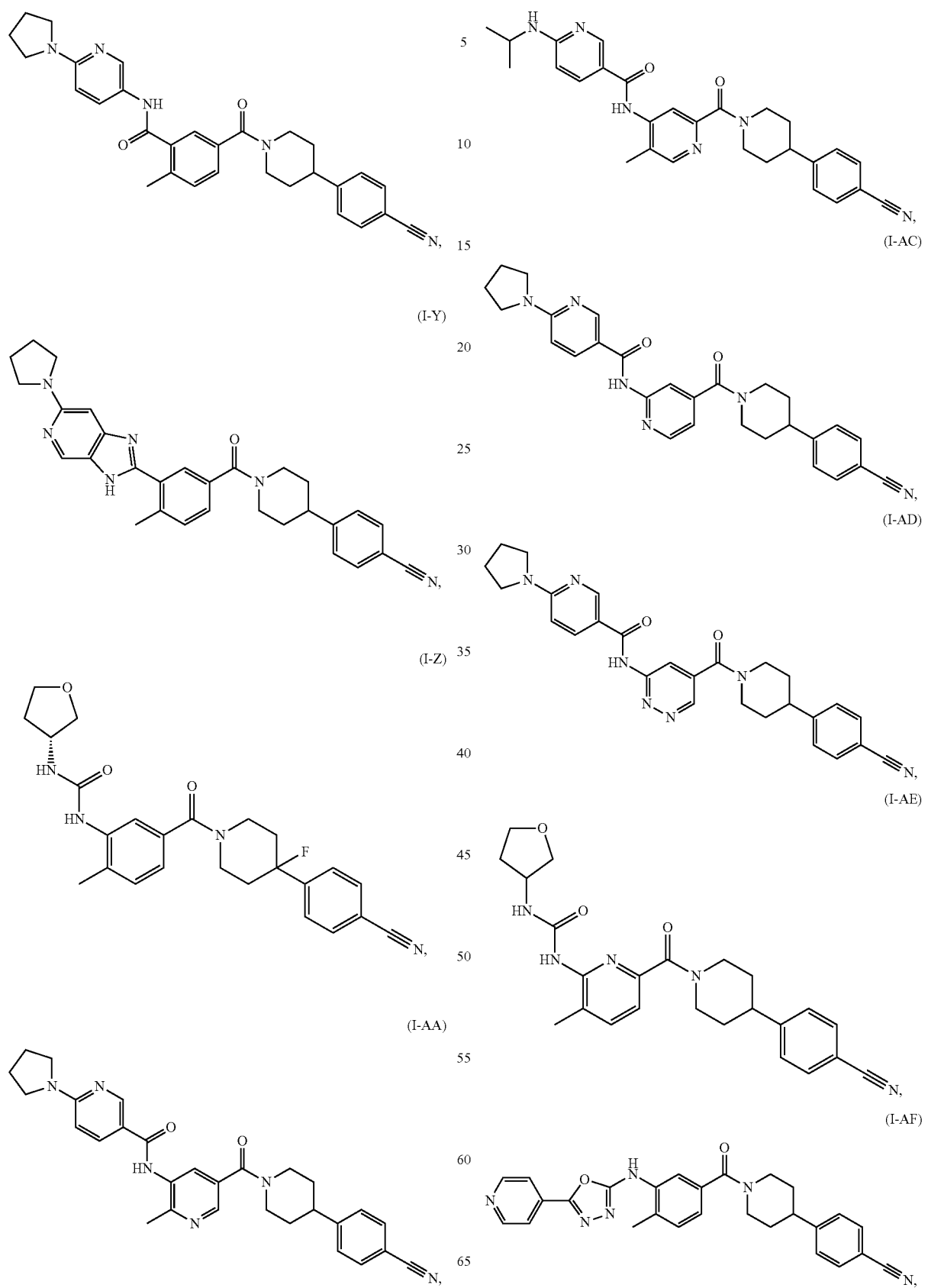

-continued

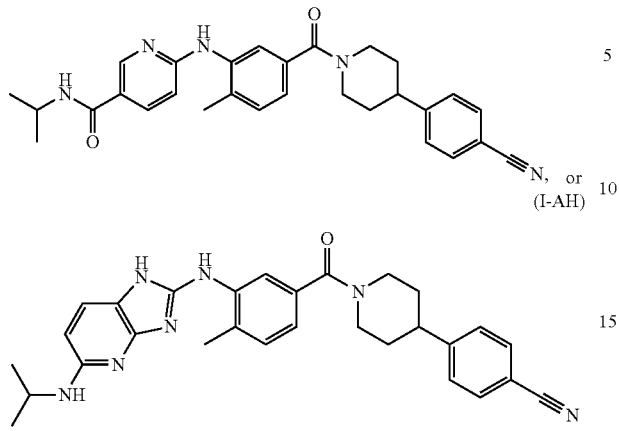

or a pharmaceutically acceptable salt thereof.

Compounds of Structure (II)

In various aspects, the present disclosure provides for compounds of Structure (II):

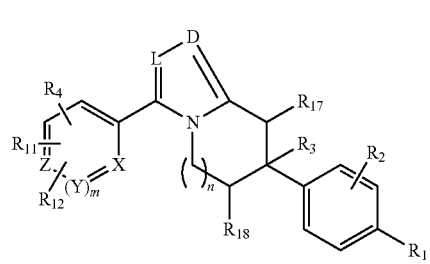

or a pharmaceutically acceptable salt thereof, wherein:

X, Y, and Z are each independently CR or NW, wherein R is H or $C_{1-6}$ alkyl and R' is H, $C_{1-6}$ alkyl, or absent;

L and D are each independently C or N;

$R_1$ is hydrogen, cyano, halo, $C_{1-6}$ alkyl, $C_{1-6}$ alkoxy, —C(=O)N($R_{13}$)($R_{14}$), —($CH_2$)$_q$C(=O)N($R_{13}$)($R_{14}$), $CF_3$, —$OCF_3$, or —S(=O)$_2R_{20}$;

q is 0, 1, 2, 3, or 4;

$R_{20}$ is hydrogen or $C_{1-6}$ alkyl, $C_{1-6}$ alkoxy, or —N($R_{13}$)($R_{14}$);

$R_2$ is hydrogen, halo, $C_{1-6}$ alkoxy, $C_{1-6}$ alkyl, or $R_2$ and $R_3$ taken together with the atoms to which they are attached form a 5-membered heterocyclyl;

$R_3$ is hydrogen, hydroxyl, halo, $C_{1-6}$ alkyl, $C_{1-6}$ alkoxy, or $R_2$ and $R_3$ taken together with the atoms to which they are attached form a 5-membered heterocyclyl;

$R_4$ is hydrogen, heteroaryl, heterocyclyl, —C(=O)N($R_5R_6$), —N($R_7$)C(=O)$R_8$, —N($R_9R_{10}$), $C_{1-6}$ alkyl, $C_{1-6}$ alkoxy, —S(=O)$_2R_{20}$, or $R_4$ and $R_{11}$ taken together with the atoms to which they are attached join together to form a heteroaryl;

$R_{11}$ is hydrogen, halo, cyano, $C_{1-6}$ alkyl, $C_{1-6}$ alkoxy, —N($R_{13}R_{14}$), $CF_3$, —$OCF_3$, —S(=O)$_2R_{20}$, $R_4$ and $R_{11}$ taken together with the atoms to which they are attached join together to form a heteroaryl, or $R_{11}$ and $R_{12}$ taken together with the atoms to which they are attached join together to form a heteroaryl;

$R_{12}$ is hydrogen, halo, cyano, $C_{1-6}$ alkyl, $C_{1-6}$ alkoxy, —N($R_{13}R_{14}$), $CF_3$, —$OCF_3$, —S(=O)$_2R_{20}$, or $R_{11}$ and $R_{12}$ taken together with the atoms to which they are attached join together to form a heteroaryl;

$R_5$, $R_6$, $R_7$, $R_8$, $R_9$, $R_{10}$, $R_{13}$, and $R_{14}$ are each independently H, $C_{1-6}$ alkyl, cycloalkyl, aryl, heterocyclyl, heteroaryl, alkylamino, or —N($R_{15}R_{16}$);

$R_{15}$ and $R_{16}$ are each independently H, $C_{1-6}$ alkyl, cycloalkyl, aryl, heterocyclyl, heteroaryl, or alkylamino;

$R_{17}$ and $R_{18}$ are each independently hydrogen or alkyl or can optionally join together to form a bond;

n is 1 or 2; and m is 0 or 1.

In certain aspects, the compounds of Structure (II) have the following Structure (II-A):

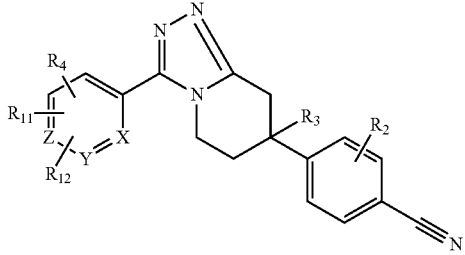

or a pharmaceutically acceptable salt thereof, wherein:

X, Y, and Z are each independently CR or NR', wherein R is H or $C_{1-6}$ alkyl and R' is H, $C_{1-6}$ alkyl, or absent;

$R_2$ is hydrogen, halo, $C_{1-6}$ alkoxy, $C_{1-6}$ alkyl, or $R_2$ and $R_3$ taken together with the atoms to which they are attached form a 5-membered heterocyclyl;

$R_3$ is hydrogen, hydroxyl, halo, $C_{1-6}$ alkyl, $C_{1-6}$ alkoxy, or $R_2$ and $R_3$ taken together with the atoms to which they are attached form a 5-membered heterocyclyl;

$R_4$ is hydrogen, heteroaryl, heterocyclyl, —C(=O)N($R_5R_6$), —N($R_7$)C(=O)$R_8$, —N($R_9R_{10}$), $C_{1-6}$ alkyl, $C_{1-6}$ alkoxy, —S(=O)$_2R_{20}$, or $R_4$ and $R_{11}$ taken together with the atoms to which they are attached join together to form a heteroaryl;

$R_{20}$ is hydrogen or $C_{1-6}$ alkyl, $C_{1-6}$ alkoxy, or —N($R_{13}$)($R_{14}$);

$R_{11}$ is hydrogen, halo, cyano, $C_{1-6}$ alkyl, $C_{1-6}$ alkoxy, —N($R_{13}R_{14}$), $CF_3$, —$OCF_3$, —S(=O)$_2R_{20}$, $R_4$ and $R_{11}$ taken together with the atoms to which they are attached join together to form a heteroaryl, or $R_{11}$ and $R_{12}$ taken together with the atoms to which they are attached join together to form a heteroaryl;

$R_{12}$ is hydrogen, halo, cyano, $C_{1-6}$ alkyl, $C_{1-6}$ alkoxy, —N($R_{13}R_{14}$), $CF_3$, —$OCF_3$, —S(=O)$_2R_{20}$, or $R_{11}$ and $R_{12}$ taken together with the atoms to which they are attached join together to form a heteroaryl;

$R_5$, $R_6$, $R_7$, $R_8$, $R_9$, $R_{10}$, $R_{13}$, and $R_{14}$ are each independently H, $C_{1-6}$ alkyl, cycloalkyl, aryl, heterocyclyl, heteroaryl, alkylamino, or —N($R_{15}R_{16}$); and $R_{15}$ and $R_{16}$ are each independently H, $C_{1-6}$ alkyl, cycloalkyl, aryl, heterocyclyl, heteroaryl, or alkylamino.

In certain aspects, the compounds of Structure (II) have the following Structure (II-B):

(II-B)

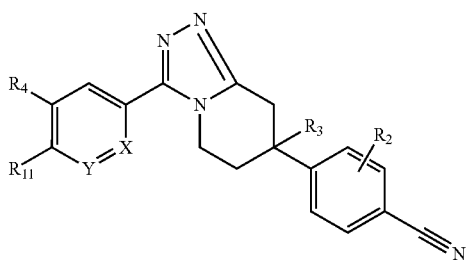

(II-E)

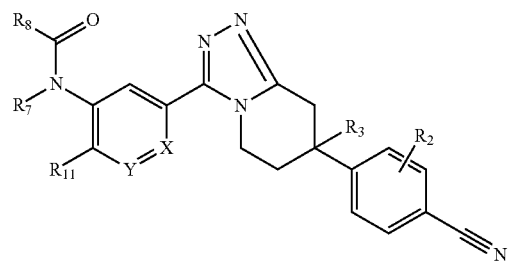

or a pharmaceutically acceptable salt thereof, wherein:

X and Y are each independently CR or NR', wherein R is H or $C_{1-6}$ alkyl and R' is H, $C_{1-6}$ alkyl, or absent;

$R_2$ is hydrogen, halo, $C_{1-6}$ alkoxy, $C_{1-6}$ alkyl, or $R_2$ and $R_3$ taken together with the atoms to which they are attached form a 5-membered heterocyclyl;

$R_3$ is hydrogen, hydroxyl, halo, $C_{1-6}$ alkyl, $C_{1-6}$ alkoxy, or $R_2$ and $R_3$ taken together with the atoms to which they are attached form a 5-membered heterocyclyl;

$R_4$ is hydrogen, heteroaryl, heterocyclyl, —C(=O)N($R_5R_6$), —N($R_7$)C(=O)$R_8$, —N($R_9R_{10}$), $C_{1-6}$ alkyl, $C_{1-6}$ alkoxy, —S(=O)$_2R_{20}$, or $R_4$ and $R_{11}$ taken together with the atoms to which they are attached join together to form a heteroaryl;

$R_{20}$ is hydrogen or $C_{1-6}$ alkyl, $C_{1-6}$ alkoxy, or —N($R_{13}$)($R_{14}$);

$R_{11}$ is hydrogen, halo, cyano, $C_{1-6}$ alkyl, $C_{1-6}$ alkoxy, —N($R_{13}R_{14}$), $CF_3$, —$OCF_3$, —S(=O)$_2R_{20}$, or $R_4$ and $R_{11}$ taken together with the atoms to which they are attached join together to form a heteroaryl;

$R_5$, $R_6$, $R_7$, $R_8$, $R_9$, and $R_{10}$ are each independently H, $C_{1-6}$ alkyl, cycloalkyl, aryl, heterocyclyl, heteroaryl, alkylamino, or —N($R_{15}R_{16}$); and $R_{15}$ and $R_{16}$ are each independently H, $C_{1-6}$ alkyl, cycloalkyl, aryl, heterocyclyl, heteroaryl, or alkylamino.

In certain aspects, the compounds of Structure (II) have one of the following Structures (II-C), (II-D), or (II-E):

(II-C)

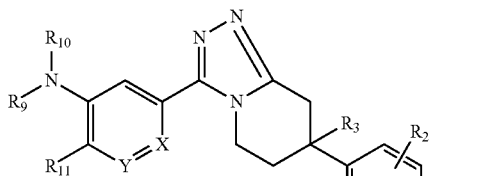

(II-D)

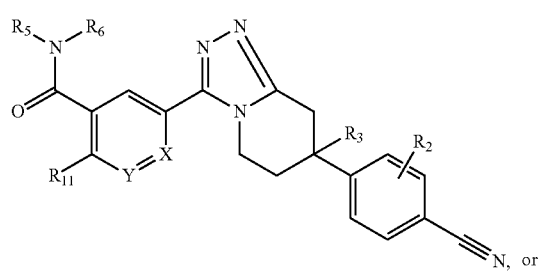

or a pharmaceutically acceptable salt thereof, wherein:

X and Y are each independently CR or NR', wherein R is H or $C_{1-6}$ alkyl and R' is H, $C_{1-6}$ alkyl, or absent;

$R_2$ is hydrogen, halo, $C_{1-6}$ alkoxy, $C_{1-6}$ alkyl, or $R_2$ and $R_3$ taken together with the atoms to which they are attached form a 5-membered heterocyclyl;

$R_3$ is hydrogen, hydroxyl, halo, $C_{1-6}$ alkyl, $C_{1-6}$ alkoxy, or $R_2$ and $R_3$ taken together with the atoms to which they are attached form a 5-membered heterocyclyl;

$R_{11}$ is hydrogen, halo, cyano, $C_{1-6}$ alkyl, $C_{1-6}$ alkoxy, —N($R_{13}R_{14}$), $CF_3$, —$OCF_3$, or —S(=O)$_2R_{20}$;

$R_{20}$ is hydrogen or $C_{1-6}$ alkyl, $C_{1-6}$ alkoxy, or —N($R_{13}$)($R_{14}$);

$R_5$, $R_6$, $R_7$, $R_8$, $R_9$, and $R_{10}$ are each independently H, $C_{1-6}$ alkyl, cycloalkyl, aryl, heterocyclyl, heteroaryl, alkylamino, or —N($R_{15}R_{16}$); and $R_{15}$ and $R_{16}$ are each independently H, $C_{1-6}$ alkyl, cycloalkyl, aryl, heterocyclyl, heteroaryl, or alkylamino.

In certain aspects, the compound of Structure (II) has the following Structure (II-F):

(II-F)

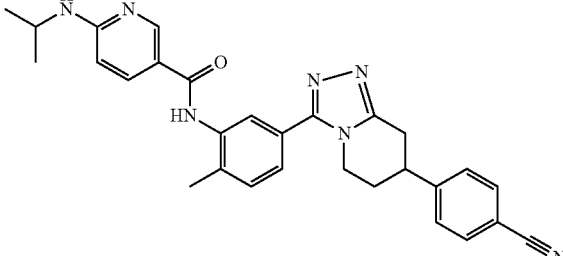

or a pharmaceutically acceptable salt thereof.

Compounds of Structure (III)

In various aspects, the present disclosure provides for compounds of Structure (III):

(III)

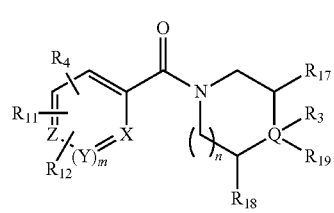

or a pharmaceutically acceptable salt thereof, wherein:

X, Y, and Z are each independently CR or NW, wherein R is H or $C_{1-6}$ alkyl and R' is H, $C_{1-6}$ alkyl, or absent;

Q is C or N;

$R_3$ is hydrogen, hydroxyl, halo, $C_{1-6}$ alkyl, $C_{1-6}$ alkoxy, or if Q is $NR_3$ is absent;

$R_4$ is hydrogen, heteroaryl, heterocyclyl, —C(=O)N($R_5R_6$), —N($R_7$)C(=O)$R_8$, —N($R_9R_{10}$), $C_{1-6}$ alkyl, $C_{1-6}$ alkoxy, —S(=O)$_2R_{20}$, or $R_4$ and $R_{11}$ taken together with the atoms to which they are attached join together to form a heteroaryl;

$R_{20}$ is hydrogen or $C_{1-6}$ alkyl, $C_{1-6}$ alkoxy, or —N($R_{13}$)($R_{14}$);

$R_{11}$ is hydrogen, halo, cyano, $C_{1-6}$ alkyl, $C_{1-6}$ alkoxy, —N($R_{13}R_{14}$), CF$_3$, —OCF$_3$, —S(=O)$_2R_{20}$, $R_4$ and $R_{11}$ taken together with the atoms to which they are attached join together to form a heteroaryl, or $R_{11}$ and $R_{12}$ taken together with the atoms to which they are attached join together to form a heteroaryl;

$R_{12}$ is hydrogen, halo, cyano, $C_{1-6}$ alkyl, $C_{1-6}$ alkoxy, —N($R_{13}R_{14}$), CF$_3$, —OCF$_3$, —S(=O)$_2R_{20}$, or $R_{11}$ and $R_{12}$ taken together with the atoms to which they are attached join together to form a heteroaryl;

$R_5$, $R_6$, $R_7$, $R_8$, $R_9$, $R_{10}$, $R_{13}$, and $R_{14}$ are each independently H, $C_{1-6}$ alkyl, cycloalkyl, aryl, heterocyclyl, heteroaryl, alkylamino, or —N($R_{15}R_{16}$);

$R_{15}$ and $R_{16}$ are each independently H, $C_{1-6}$ alkyl, cycloalkyl, aryl, heterocyclyl, heteroaryl, or alkylamino;

$R_{17}$ and $R_{18}$ are each independently hydrogen or alkyl or can optionally join together to form a bond;

$R_{19}$ is aryl, heteroaryl, cycloalkyl, or heterocyclyl;

n is 0, 1, or 2; and m is 0 or 1.

In certain aspects, the compounds of Structure (III) have one of the following Structures (III-A), (III-B), or (III-C):

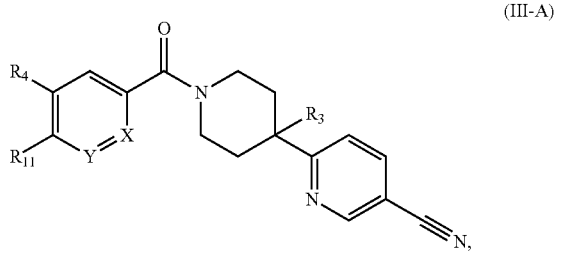

(III-A)

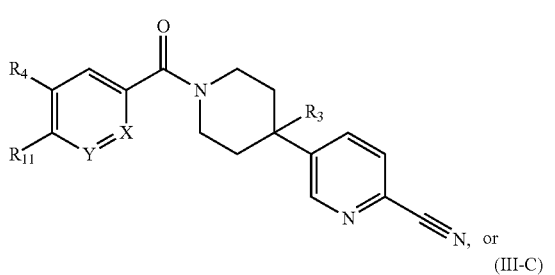

(III-B)

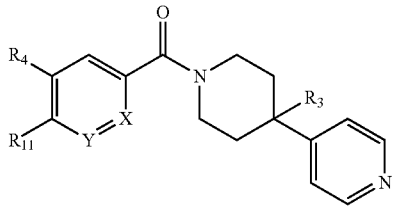

(III-C)

or a pharmaceutically acceptable salt thereof, wherein:

X and Y are each independently CR or NR', wherein R is H or $C_{1-6}$ alkyl and R' is H, $C_{1-6}$ alkyl, or absent;

$R_3$ is hydrogen, hydroxyl, halo, $C_{1-6}$ alkyl, or $C_{1-6}$ alkoxy;

$R_4$ is hydrogen, heteroaryl, heterocyclyl, —C(=O)N($R_5R_6$), —N($R_7$)C(=O)$R_8$, —N($R_9R_{10}$), $C_{1-6}$ alkyl, $C_{1-6}$ alkoxy, —S(=O)$_2R_{20}$, or $R_4$ and $R_{11}$ taken together with the atoms to which they are attached join together to form a heteroaryl;

$R_{11}$ is hydrogen, halo, cyano, $C_{1-6}$ alkyl, $C_{1-6}$ alkoxy, —N($R_{13}R_{14}$), CF$_3$, —OCF$_3$, —S(=O)$_2R_{20}$, or $R_4$ and $R_{11}$ taken together with the atoms to which they are attached join together to form a heteroaryl;

$R_5$, $R_6$, $R_7$, $R_8$, $R_9$, and $R_{10}$ are each independently H, $C_{1-6}$ alkyl, cycloalkyl, aryl, heterocyclyl, heteroaryl, alkylamino, or —N($R_{15}R_{16}$); and $R_{15}$ and $R_{16}$ are each independently H, $C_{1-6}$ alkyl, cycloalkyl, aryl, heterocyclyl, heteroaryl, or alkylamino.

In certain aspects, the compounds of Structure (III) have one of the following Structures (III-D), (III-E), or (III-F):

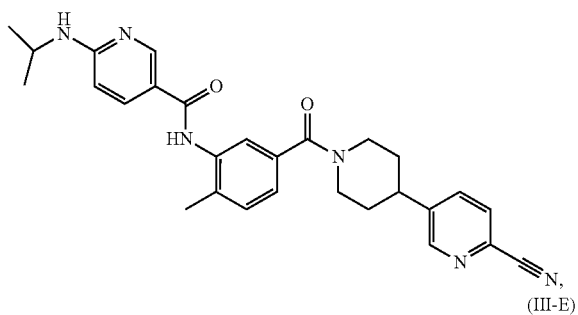

(III-D)

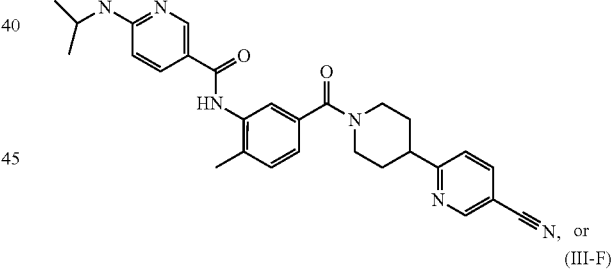

(III-E)

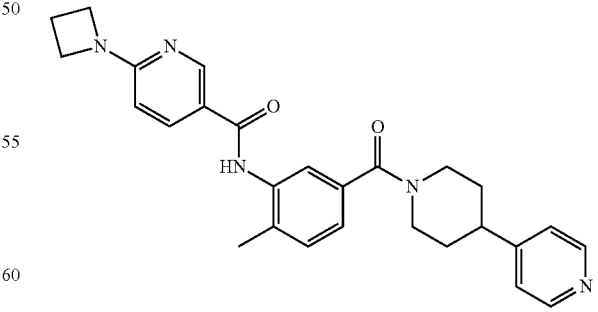

(III-F)

or a pharmaceutically acceptable salt thereof.

Compounds of Structure (IV)

In certain aspects, the compounds of Structure (IV) have one of the following Structures (IV-A), (IV-B), or (IV-C):

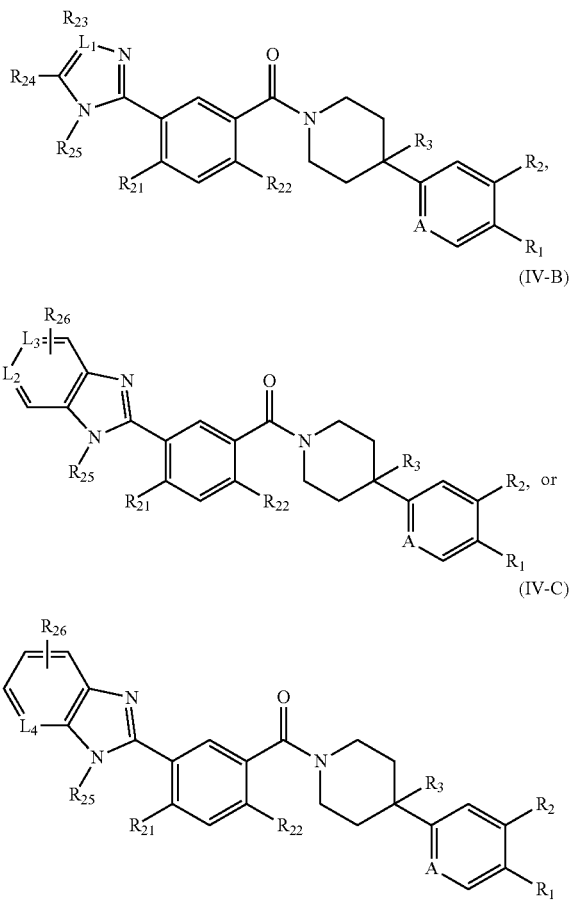

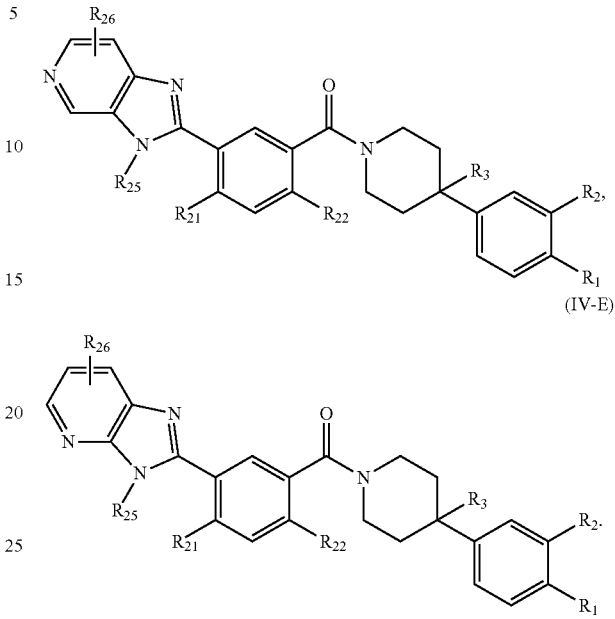

In certain aspects, the compounds of Structure (IV) have one of the following Structures (IV-D) and (IV-E):

or a pharmaceutically acceptable salt thereof, wherein:
$L_1$, $L_2$, $L_3$, $L_4$, and A are each independently CH or N;
$R_1$ is hydrogen, cyano, halo, $C_{1-6}$ alkyl, $C_{1-6}$ alkoxy, —C(=O)N($R_{13}$)($R_{14}$), —(CH$_2$)$_q$C(=O)N($R_{13}$)($R_{14}$), CF$_3$, —OCF$_3$, or —S(=O)$_2$R$_{20}$;
q is 0, 1, 2, 3, or 4;
$R_{20}$ is hydrogen or $C_{1-6}$ alkyl, $C_{1-6}$ alkoxy, or —N($R_{13}$)($R_{14}$);
$R_2$ is hydrogen, halo, $C_{1-6}$ alkoxy, or $C_{1-6}$ alkyl;
$R_3$ is hydrogen, hydroxyl, halo, $C_{1-6}$ alkyl, or $C_{1-6}$ alkoxy;
$R_{21}$ and $R_{22}$ are each independently hydrogen, halo, cyano, $C_{1-6}$ alkyl, $C_{1-6}$ alkoxy, CF$_3$, —OCF$_3$, or —S(=O)$_2$R$_{20}$;
$R_{23}$ is hydrogen, —N($R_{13}$)($R_{14}$), $C_{1-6}$ alkyl, $C_{1-6}$ alkoxy, is absent if $L_1$ is N, or $R_{23}$ and $R_{24}$ taken together with the atoms to which they are attached join together to form a heterocyclyl, heteroaryl, or cycloalkyl;
$R_{24}$ is hydrogen, —N($R_{13}$)($R_{14}$), $C_{1-6}$ alkyl, $C_{1-6}$ alkoxy, —(C$_{1-6}$ alkoxy)(heterocyclyl), heterocyclyl, or $R_{23}$ and $R_{24}$ taken together with the atoms to which they are attached join together to form a heterocyclyl, heteroaryl, or cycloalkyl;
$R_{26}$ is hydrogen, heteroaryl, heterocycyl, —N($R_{13}$)($R_{14}$), or —S(=O)$_2$R$_{20}$;
$R_{13}$ and $R_{14}$ are each independently hydrogen, $C_{1-6}$ alkyl, cycloalkyl, aryl, heterocyclyl, heteroaryl, hydroxyalkyl, alkylamino, or —N($R_{15}R_{16}$), or —S(=O)$_2$R$_{20}$;
$R_{25}$ is hydrogen, $C_{1-6}$ alkyl, or $C_{1-6}$ alkoxy; and
$R_{15}$ and $R_{16}$ are each independently hydrogen, $C_{1-6}$ alkyl, $C_{1-6}$ alkoxy, cycloalkyl, aryl, heterocyclyl, heteroaryl, hydroxyalkyl, or alkylamino.

or a pharmaceutically acceptable salt thereof.
$R_1$ is hydrogen, cyano, halo, $C_{1-6}$ alkyl, $C_{1-6}$ alkoxy, —C(=O)N($R_{13}$)($R_{14}$), —(CH$_2$)$_q$C(=O)N($R_{13}$)($R_{14}$), CF$_3$, —OCF$_3$, or —S(=O)$_2$R$_{20}$;
q is 0, 1, 2, 3, or 4;
$R_{20}$ is hydrogen or $C_{1-6}$ alkyl, $C_{1-6}$ alkoxy, or —N($R_{13}$)($R_{14}$);
$R_2$ is hydrogen, halo, $C_{1-6}$ alkoxy, or $C_{1-6}$ alkyl;
$R_3$ is hydrogen, hydroxyl, halo, $C_{1-6}$ alkyl, or $C_{1-6}$ alkoxy;
$R_{21}$ and $R_{22}$ are each independently hydrogen, halo, cyano, $C_{1-6}$ alkyl, $C_{1-6}$ alkoxy, CF$_3$, —OCF$_3$, or —S(=O)$_2$R$_{20}$;
$R_{26}$ is hydrogen, heteroaryl, heterocycyl, —N($R_{13}$)($R_{14}$), or —S(=O)$_2$R$_{20}$;
$R_{13}$ and $R_{14}$ are each independently hydrogen, $C_{1-6}$ alkyl, cycloalkyl, aryl, heterocyclyl, heteroaryl, hydroxyalkyl, alkylamino, —N($R_{15}R_{16}$), or —S(=O)$_2$R$_{20}$;
$R_{25}$ is hydrogen, $C_{1-6}$ alkyl, or $C_{1-6}$ alkoxy; and
$R_{15}$ and $R_{16}$ are each independently hydrogen, $C_{1-6}$ alkyl, $C_{1-6}$ alkoxy, cycloalkyl, aryl, heterocyclyl, heteroaryl, hydroxyalkyl, or alkylamino.

In certain aspects, the compounds of Structure (IV) have one of the following Structures (IV-F) and (IV-G):

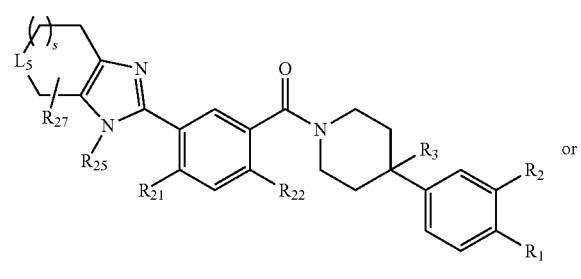

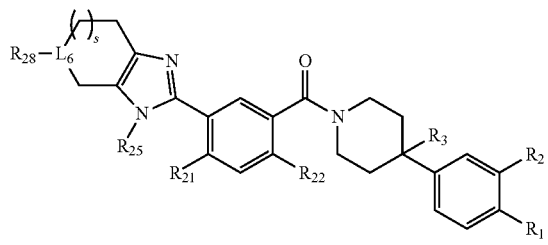

(IV-G)

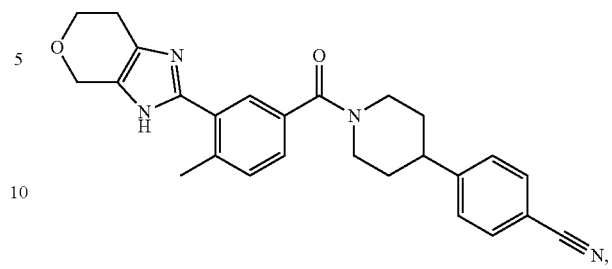

(IV-H)

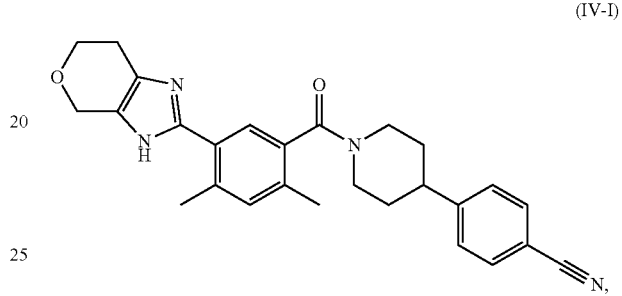

(IV-I)

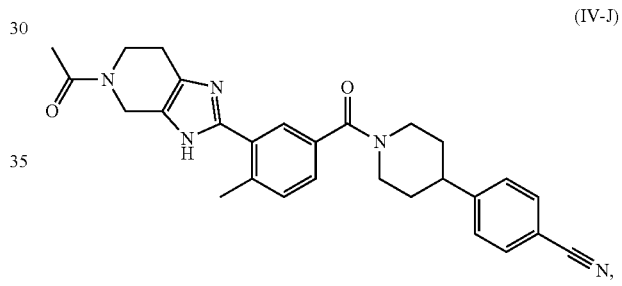

(IV-J)

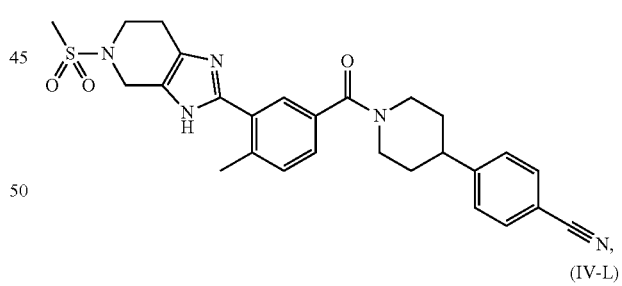

(IV-K)

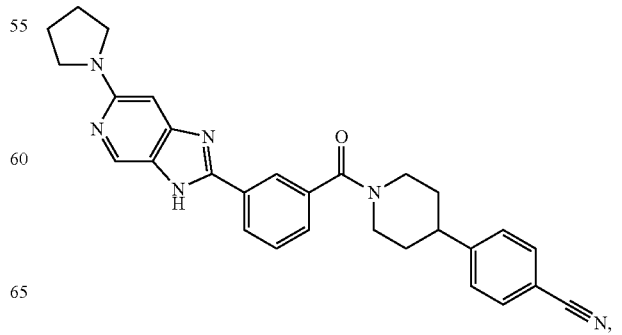

(IV-L)

or a pharmaceutically acceptable salt thereof, wherein:
$R_1$ is hydrogen, cyano, halo, $C_{1-6}$ alkyl, $C_{1-6}$ alkoxy, —C(=O)N($R_{13}$)($R_{14}$), —(CH$_2$)$_q$C(=O)N($R_{13}$)($R_{14}$), CF$_3$, —OCF$_3$, or —S(=O)$_2$R$_{20}$;

q is 0, 1, 2, 3, or 4;

$R_{20}$ is hydrogen or $C_{1-6}$ alkyl, $C_{1-6}$ alkoxy, or —N($R_{13}$)($R_{14}$);

$R_2$ is hydrogen, halo, $C_{1-6}$ alkoxy, or $C_{1-6}$ alkyl;

$R_3$ is hydrogen, hydroxyl, halo, $C_{1-6}$ alkyl, or $C_{1-6}$ alkoxy;

$R_{21}$ and $R_{22}$ are each independently hydrogen, halo, cyano, $C_{1-6}$ alkyl, $C_{1-6}$ alkoxy, CF$_3$, —OCF$_3$, or —S(=O)$_2$R$_{20}$;

$R_{13}$ and $R_{14}$ are each independently hydrogen, $C_{1-6}$ alkyl, cycloalkyl, aryl, heterocyclyl, heteroaryl, hydroxyalkyl, alkylamino, —N($R_{15}R_{16}$), or —S(=O)$_2$R$_{20}$;

$R_{25}$ is hydrogen, $C_{1-6}$ alkyl, or $C_{1-6}$ alkoxy;

$R_{15}$ and $R_{16}$ are each independently hydrogen, $C_{1-6}$ alkyl, $C_{1-6}$ alkoxy, cycloalkyl, aryl, heterocyclyl, heteroaryl, hydroxyalkyl, or alkylamino;

s is 0, 1, or 2;

$L_5$ is CH$_2$, NH, S, or O;

$L_6$ is CH or N;

$R_{27}$ is hydrogen, —C(=O)R", —S(=O)$_2$R$_{20}$;

$R_{28}$ is hydrogen, —C(=O)R", —S(=O)$_2$R$_{20}$, or is absent if $L_6$ is O; and R" is hydrogen, $C_{1-6}$ alkyl, $C_{1-6}$ alkoxy, —C(=O)N($R_{13}$)($R_{14}$), or —N($R_{13}$)($R_{14}$).

In certain aspects of Structure (IV), $R_1$ is hydrogen, cyano, $C_{1-6}$ alkyl, $C_{1-6}$ alkoxy, or —C(=O)N($R_{13}$)($R_{14}$).

In certain aspects of Structure (IV), $R_1$ is cyano.

In certain aspects of Structure (IV), $R_2$ is hydrogen or halo; $R_2$ is hydrogen.

In certain aspects of Structure (IV), $R_3$ is hydrogen.

In certain aspects of Structure (IV), $R_{21}$ and $R_{22}$ are each independently hydrogen or $C_{1-6}$ alkyl.

In certain aspects of Structure (IV), $R_{21}$ and $R_{22}$ are each independently $C_{1-6}$ alkyl.

In certain aspects of Structure (IV), $R_{25}$ is hydrogen.

In certain aspects of Structure (IV), $L_2$ is N.

In certain aspects of Structure (IV), $L_1$ is CH.

In certain aspects of Structure (IV), $L_3$ is CH.

In certain aspects of Structure (IV), $L_4$ is CH.

In certain aspects of Structure (IV), A is N.

In certain aspects of Structure (IV), A is CH.

In certain aspects of Structure (IV), $R_{26}$ is heterocyclyl.

In certain aspects of Structure (IV), $R_{24}$ is —N($R_{13}$)($R_{14}$).

In certain aspects of Structure (IV), $L_5$ and $L_6$ are each independently N. In certain aspects of Structure (IV), s is 1.

In certain aspects of Structure (IV), s is 0.

In certain aspects, the compounds of Structure (IV) have one of the following Structures (IV-H), (IV-I), (IV-J), (IV-K), (IV-L), (IV-M), (IV-N), or (IV-O):

-continued (IV-M)
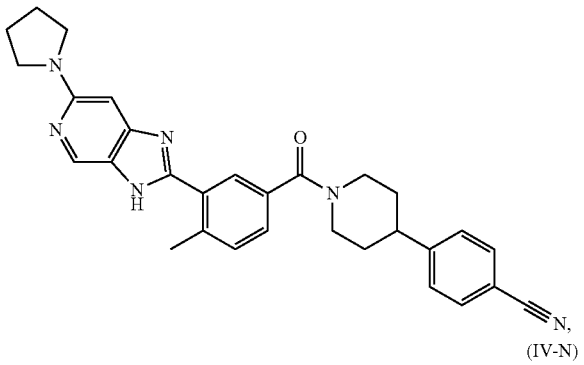

(IV-N)
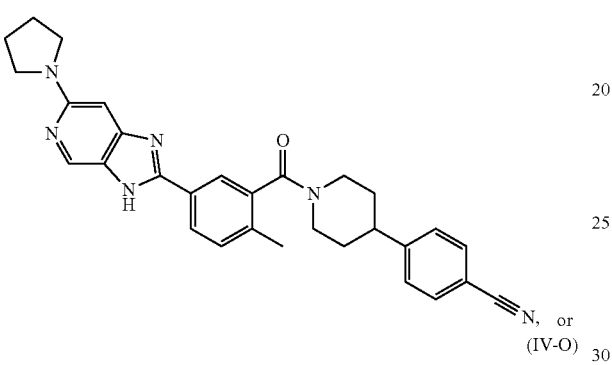

or (IV-O)
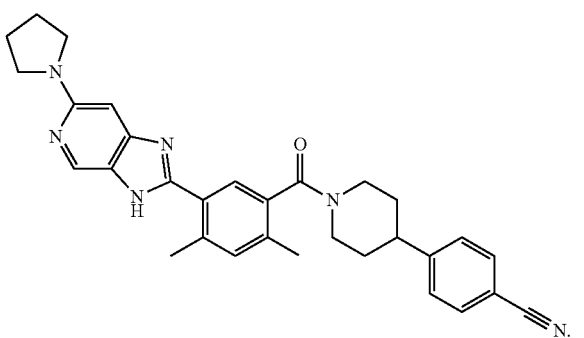

or a pharmaceutically acceptable salt thereof.

Compounds of Structure (V)

In various aspects, the present disclosure provides for compounds of Structure (V):

(V)
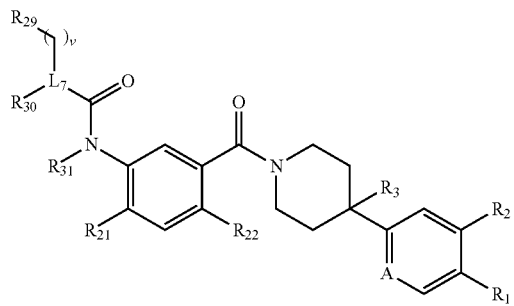

or a pharmaceutically acceptable salt thereof, wherein:

$L_7$ is N or O, wherein $R_{30}$ is absent if $L_7$ is O;

A is CH or N;

$R_1$ is hydrogen, cyano, halo, $C_{1-6}$ alkyl, $C_{1-6}$ alkoxy, —C(=O)N($R_{13}$)($R_{14}$), —(CH$_2$)$_q$C(=O)N($R_{13}$)($R_{14}$), CF$_3$, —OCF$_3$, or —S(=O)$_2$R$_{20}$;

q is 0, 1, 2, 3, or 4;

$R_{20}$ is hydrogen or $C_{1-6}$ alkyl, $C_{1-6}$ alkoxy, or —N($R_{13}$)($R_{14}$);

$R_2$ is hydrogen, halo, $C_{1-6}$ alkoxy, or $C_{1-6}$ alkyl;

$R_3$ is halo, $C_{1-6}$ alkyl, or $C_{1-6}$ alkoxy;

$R_{21}$ and $R_{22}$ are each independently hydrogen, halo, cyano, $C_{1-6}$ alkyl, $C_{1-6}$ alkoxy, CF$_3$, —OCF$_3$, or —S(=O)$_2$R$_{20}$;

$R_{29}$ and $R_{30}$ are each independently hydrogen, $C_{1-6}$ alkyl, $C_{1-6}$ alkoxy, hydroxyalkyl, heteroaryl, heterocyclyl, —N($R_{15}R_{16}$), —C(=O)R$_{46}$, —R$_{48}$C(=O)R$_{47}$, or $R_{29}$ and $R_{30}$ taken together with the atoms to which they are attached join together to form a heteroaryl or heterocyclyl, wherein $R_{30}$ is absent if $L_7$ is O;

$R_{46}$ and $R_{47}$ are each independently hydrogen, $C_{1-6}$ alkyl, cycloalkyl, aryl, heterocyclyl, heteroaryl, hydroxyalkyl, —N($R_{15}R_{16}$), or —S(=O)$_2$R$_{20}$;

$R_{48}$ is alkyl or is absent;

$R_{31}$ is hydrogen, $C_{1-6}$ alkyl, or $C_{1-6}$ alkoxy;

$R_{13}$ and $R_{14}$ are each independently hydrogen, $C_{1-6}$ alkyl, cycloalkyl, aryl, heterocyclyl, heteroaryl, hydroxyalkyl, alkylamino, —N($R_{15}R_{16}$), or —S(=O)$_2$R$_{20}$;

$R_{15}$ and $R_{16}$ are each independently hydrogen, $C_{1-6}$ alkyl, cycloalkyl, aryl, heterocyclyl, heteroaryl, hydroxyalkyl, or alkylamino; and v is 0 or 1.

In certain aspects, the compounds of Structure (V) have one of the following Structures (V-A), (V-B), (V-C), or (V-D):

(V-A)

(V-B)

-continued (V-C)

(V-D)

or a pharmaceutically acceptable salt thereof, wherein:
R$_1$ is hydrogen, cyano, halo, C$_{1-6}$ alkyl, C$_{1-6}$ alkoxy, —C(=O)N(R$_{13}$)(R$_{14}$), —(CH$_2$)$_q$C(=O)N(R$_{13}$)(R$_{14}$), CF$_3$, —OCF$_3$, or —S(=O)$_2$R$_{20}$;
q is 0, 1, 2, 3, or 4;
R$_{20}$ is hydrogen or C$_{1-6}$ alkyl, C$_{1-6}$ alkoxy, or —N(R$_{13}$)(R$_{14}$);
R$_2$ is hydrogen, halo, C$_{1-6}$ alkoxy, or C$_{1-6}$ alkyl;
R$_3$ is halo, C$_{1-6}$ alkyl, or C$_{1-6}$ alkoxy;
R$_{21}$ and R$_{22}$ are each independently hydrogen, halo, cyano, C$_{1-6}$ alkyl, C$_{1-6}$ alkoxy, CF$_3$, —OCF$_3$, or —S(=O)$_2$R$_{20}$;
R$_{30}$ is hydrogen, C$_{1-6}$ alkyl, C$_{1-6}$ alkoxy, hydroxyalkyl, heteroaryl, heterocyclyl, —N(R$_{15}$R$_{16}$), —C(=O)R$_{46}$, or —R$_{48}$C(=O)R$_{47}$, wherein R$_{30}$ is absent if L$_7$ is O;
R$_{46}$ and R$_{47}$ are each independently hydrogen, C$_{1-6}$ alkyl, cycloalkyl, aryl, heterocyclyl, heteroaryl, hydroxyalkyl, —N(R$_{15}$R$_{16}$), or —S(=O)$_2$R$_{20}$;
R$_{48}$ is alkyl or is absent;
R$_{31}$ is hydrogen, C$_{1-6}$ alkyl, or C$_{1-6}$ alkoxy;
R$_{13}$ and R$_{14}$ are each independently hydrogen, C$_{1-6}$ alkyl, cycloalkyl, aryl, heterocyclyl, heteroaryl, hydroxyalkyl, alkylamino, —N(R$_{15}$R$_{16}$), or —S(=O)$_2$R$_{20}$;
R$_{15}$ and R$_{16}$ are each independently hydrogen, C$_{1-6}$ alkyl, cycloalkyl, aryl, heterocyclyl, heteroaryl, hydroxyalkyl, or alkylamino;
L$_8$, L$_9$, and L$_{10}$ are each independently CH$_2$, NH, or O;
L$_{11}$ and L$_{12}$ are each independently CH or N;
R$_{32}$ and R$_{33}$ are each independently hydrogen, C$_{1-6}$ alkyl, C$_{1-6}$ alkoxy, —S(=O)$_2$R$_{20}$, —C(=O)R$_{46}$, hydroxyalkyl, hydroxyl, or are absent;
u is 0, 1, or 2; and
t is 0, 1, or 2.
In certain aspects of Structure (V), L$_7$ is N.
In certain aspects of Structure (V), L$_7$ is O.
In certain aspects of Structure (V), A is N.
In certain aspects of Structure (V), A is CH.
In certain aspects of Structure (V), R$_1$ is hydrogen, cyano, C$_{1-6}$ alkyl, C$_{1-6}$ alkoxy, or —C(=O)N(R$_{13}$)(R$_{14}$).
In certain aspects of Structure (V), R$_1$ is cyano.
In certain aspects of Structure (V), R$_2$ is hydrogen or halo.
In certain aspects of Structure (V), R$_2$ is hydrogen.
In certain aspects of Structure (V), R$_3$ is fluorine.
In certain aspects of Structure (V), R$_{21}$ and R$_{22}$ are each independently hydrogen or C$_{1-6}$ alkyl.
In certain aspects of Structure (V), R$_{21}$ and R$_{22}$ are each independently C$_{1-6}$ alkyl.
In certain aspects of Structure (V), R$_{31}$ is hydrogen.
In certain aspects of Structure (V), R$_{30}$ is hydrogen.
In certain aspects of Structure (V), L$_8$ is O.
In certain aspects of Structure (V), L$_9$ is O.
In certain aspects of Structure (V), L$_{10}$ is O and L$_{11}$ is N.
In certain aspects of Structure (V), L$_{12}$ is N.
In certain aspects of Structure (V), R$_{32}$ and R$_{33}$ are each independently hydrogen.

In certain aspects, the compounds of Structure (V) have one of the following Structures (V-I), (V-J), (V-K), (V-L), (V-M), (V-N), or (V-O):

(V-I)

(V-J)

(V-K)

-continued

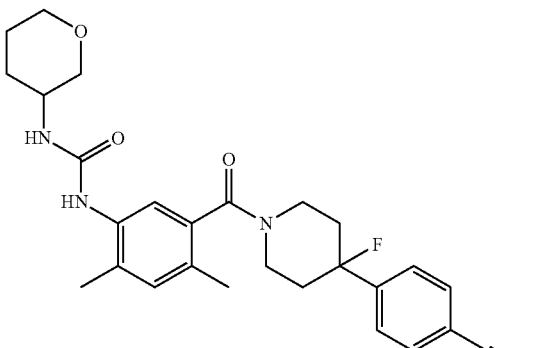

(V-L)

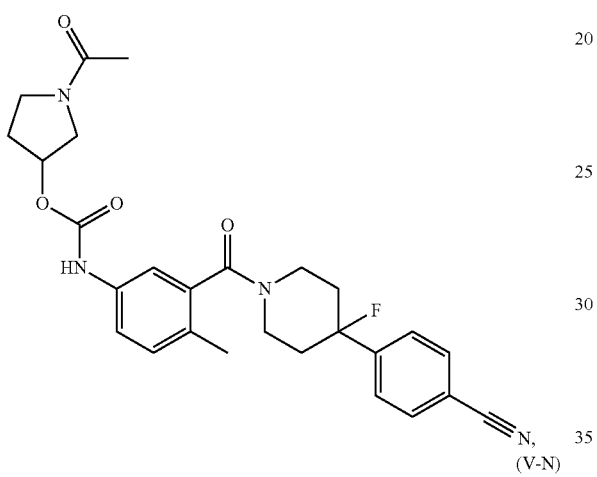

(V-M)

(V-N)

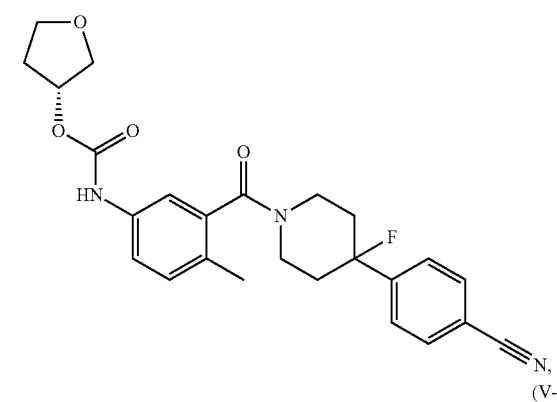

(V-O)

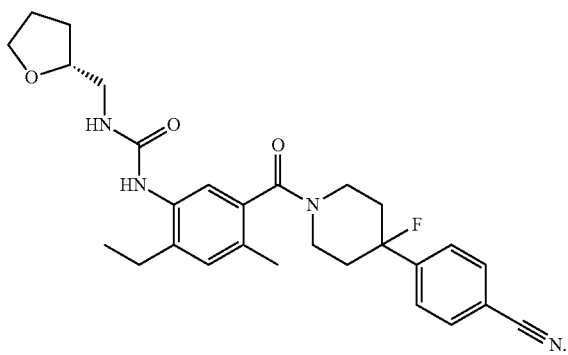

or a pharmaceutically acceptable salt thereof.

Compounds of Structure (VI)

In certain aspects, the compounds of Structure (VI) have one of the following Structures (VI-A) or (VI-B):

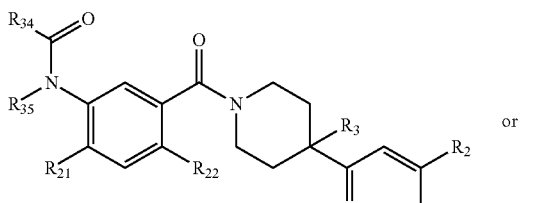

(VI-A)

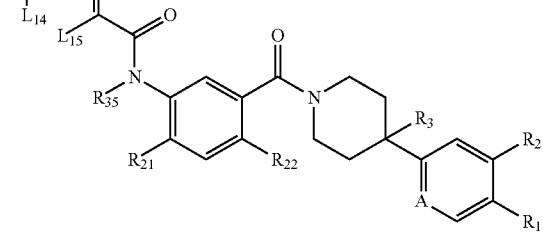

(VI-B)

or a pharmaceutically acceptable salt thereof, wherein:

$L_{13}$, $L_{14}$, $L_{15}$, and A are each independently CH or N;

$R_1$ is hydrogen, cyano, halo, $C_{1-6}$ alkyl, $C_{1-6}$ alkoxy, —C(=O)N($R_{13}$)($R_{14}$), —(CH$_2$)$_q$C(=O)N($R_{13}$)($R_{14}$), CF$_3$, —OCF$_3$, or —S(=O)$_2$R$_{20}$;

q is 0, 1, 2, 3, or 4;

$R_{20}$ is hydrogen or $C_{1-6}$ alkyl, $C_{1-6}$ alkoxy, or —N($R_{13}$)($R_{14}$);

$R_2$ is hydrogen, halo, $C_{1-6}$ alkoxy, or $C_{1-6}$ alkyl;

$R_3$ is halo, $C_{1-6}$ alkyl, or $C_{1-6}$ alkoxy;

$R_{21}$ and $R_{22}$ are each independently hydrogen, halo, cyano, $C_{1-6}$ alkyl, $C_{1-6}$ alkoxy, CF$_3$, —OCF$_3$, or —S(=O)$_2$R$_{20}$;

$R_{34}$ is hydrogen, $C_{1-6}$ alkyl, $C_{1-6}$ alkoxy, cycloalkyl, hydroxyl, hydroxyalkyl, aryl, heterocyclyl, heteroaryl, alkylamino, CF$_3$, —OCF$_3$, —S(=O)$_2$R$_{20}$, or —N($R_{15}R_{16}$);

$R_{35}$ is hydrogen, $C_{1-6}$ alkyl, or $C_{1-6}$ alkoxy;

$R_{36}$ is hydrogen, $C_{1-6}$ alkyl, $C_{1-6}$ alkoxy, —N($R_{15}R_{16}$), heterocyclyl, or heteroaryl;

$R_{13}$ and $R_{14}$ are each independently hydrogen, $C_{1-6}$ alkyl, cycloalkyl, aryl, heterocyclyl, heteroaryl, hydroxyalkyl, alkylamino, —N($R_{15}R_{16}$), or —S(=O)$_2$R$_{20}$; and $R_{15}$ and $R_{16}$ are each independently hydrogen, $C_{1-6}$ alkyl, $C_{1-6}$ alkoxy, cycloalkyl, aryl, heterocyclyl, heteroaryl, hydroxyalkyl, or alkylamino.

In certain aspects, the compounds of Structure (VI) have one of the following Structures (VI-C) or (VI-D):

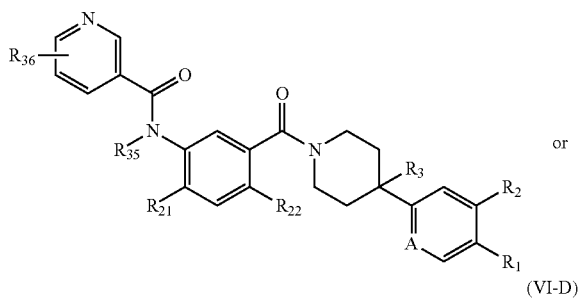

(VI-C)

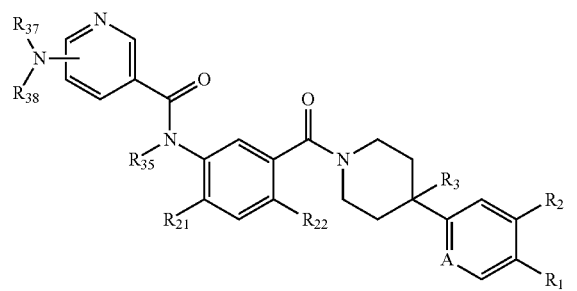

(VI-D)

or a pharmaceutically acceptable salt thereof, wherein:
$R_1$ is hydrogen, cyano, halo, $C_{1-6}$ alkyl, $C_{1-6}$ alkoxy, —C(=O)N($R_{13}$)($R_{14}$), —(CH$_2$)$_q$C(=O)N($R_{13}$)($R_{14}$), CF$_3$, —OCF$_3$, or —S(=O)$_2$R$_{20}$;
q is 0, 1, 2, 3, or 4;
$R_{20}$ is hydrogen or $C_{1-6}$ alkyl, $C_{1-6}$ alkoxy, or —N($R_{13}$)($R_{14}$);
$R_2$ is hydrogen, halo, $C_{1-6}$ alkoxy, or $C_{1-6}$ alkyl;
$R_3$ is halo, $C_{1-6}$ alkyl, or $C_{1-6}$ alkoxy;
$R_{21}$ and $R_{22}$ are each independently hydrogen, halo, cyano, $C_{1-6}$ alkyl, $C_{1-6}$ alkoxy, CF$_3$, —OCF$_3$, or —S(=O)$_2$R$_{20}$;
$R_{35}$ is hydrogen, $C_{1-6}$ alkyl, or $C_{1-6}$ alkoxy;
$R_{36}$ is hydrogen, $C_{1-6}$ alkyl, $C_{1-6}$ alkoxy, —N($R_{15}R_{16}$), heterocyclyl, or heteroaryl;
$R_{13}$ and $R_{14}$ are each independently hydrogen, $C_{1-6}$ alkyl, cycloalkyl, aryl, heterocyclyl, heteroaryl, hydroxyalkyl, alkylamino, —N($R_{15}R_{16}$), or —S(=O)$_2$R$_{20}$;
$R_{15}$ and $R_{16}$ are each independently hydrogen, $C_{1-6}$ alkyl, $C_{1-6}$ alkoxy, cycloalkyl, aryl, heterocyclyl, heteroaryl, hydroxyalkyl, or alkylamino; and
$R_{37}$ and $R_{38}$ are each independently hydrogen, $C_{1-6}$ alkyl, $C_{1-6}$ alkoxy, hydroxyalkyl, heteroaryl, heterocyclyl, or $R_{37}$ and $R_{38}$ taken together with the atoms to which they are attached join together to form a heteroaryl or heterocyclyl.

In certain aspects of Structure (VI), $R_1$ is hydrogen, cyano, $C_{1-6}$ alkyl, $C_{1-6}$ alkoxy, or —C(=O)N($R_{13}$)($R_{14}$).
In certain aspects of Structure (VI), $R_1$ is cyano.
In certain aspects of Structure (VI), $R_2$ is hydrogen or halo.
In certain aspects of Structure (VI), $R_2$ is hydrogen.
In certain aspects of Structure (VI), $R_3$ is fluorine.
In certain aspects of Structure (VI), $R_{21}$ and $R_{22}$ are each independently hydrogen or $C_{1-6}$ alkyl.
In certain aspects of Structure (VI), $R_{21}$ and $R_{22}$ are each independently $C_{1-6}$ alkyl.
In certain aspects of Structure (VI), $R_{35}$ is hydrogen.
In certain aspects of Structure (VI), $R_{34}$ is heteroaryl;
In certain aspects of Structure (VI), $R_{34}$ is thienyl, pyrryl, furyl, pyridyl, pyrimidyl, pyrazinyl, pyrazolyl, oxazolyl, isoxazolyl, imidazolyl, thiazolyl, pyranyl, tetrazolyl, pyrrolyl, pyrrolinyl, pyridazinyl, triazolyl, indolyl, isoindolyl, indolizinyl, benzimidazolyl, quinolyl, isoquinolyl, indazolyl, benzotriazolyl, tetrazolopyridazinyl, oxadiazolyl, benzoxazolyl, benzoxadiazolyl, thiadiazolyl, benzothiazolyl, or benzothiadiazolyl.

In certain aspects of Structure (VI), $L_{13}$ is N.
In certain aspects of Structure (VI), $L_{14}$ and $L_{15}$ are each independently CH.
In certain aspects of Structure (VI), A is N.
In certain aspects of Structure (VI), A is CH.
In certain aspects, the compounds of Structure (VI) have one of the following Structures (VI-E), (VI-F), (VI-G), (VI-H), or (VI-I):

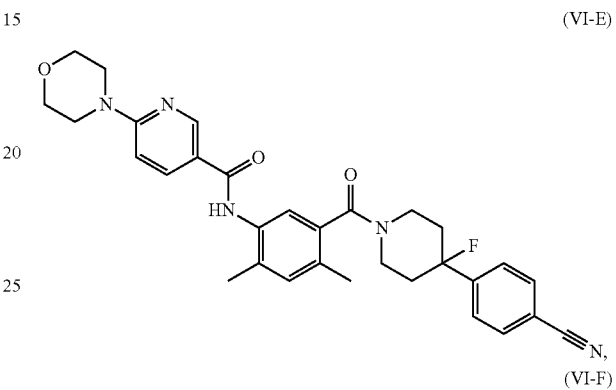

(VI-E)

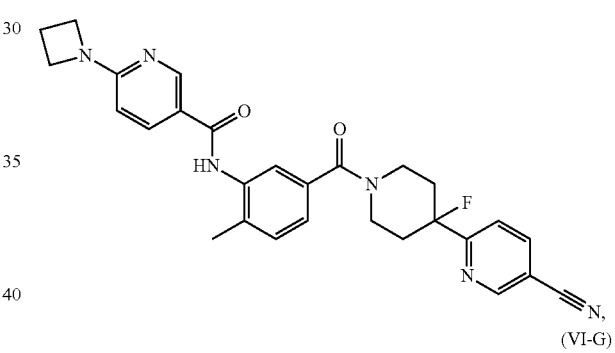

(VI-F)

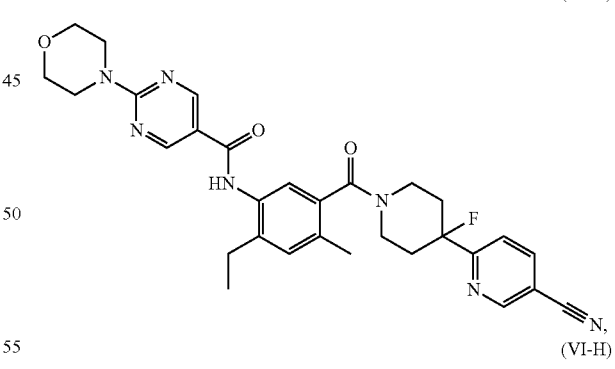

(VI-G)

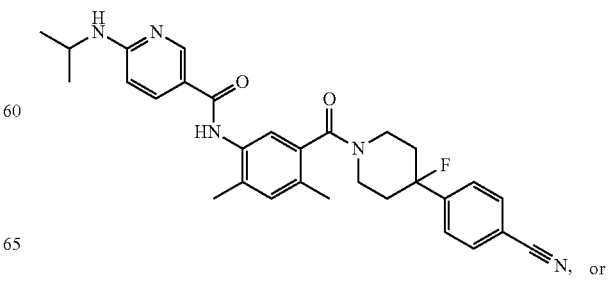

(VI-H)

or

-continued

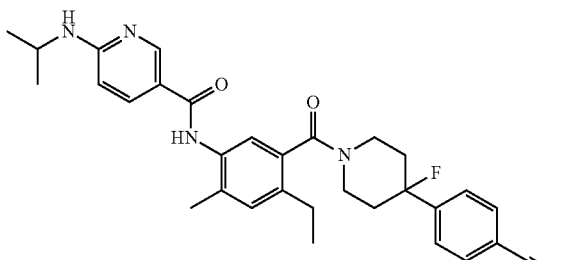

(VI-I)

or a pharmaceutically acceptable salt thereof.

In various aspects, the present disclosure provides for compounds of Structure (VI-J):

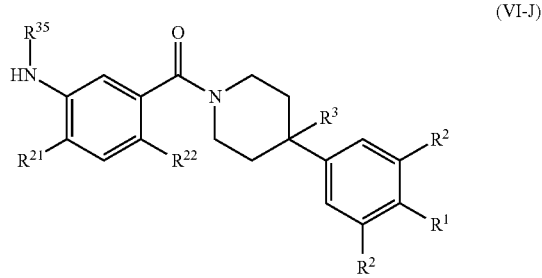

(VI-J)

or a pharmaceutically acceptable salt thereof, wherein:
$R^1$ is H, —CN, halogen, $C_1$-$C_4$ straight or branched alkyl, —O—($C_3$-$C_5$ cycloalkyl), —O—($C_1$-$C_4$ straight or branched alkyl) wherein:
  the $C_3$-$C_5$ cycloalkyl optionally includes an oxygen or nitrogen heteroatom; and
  when $R^1$ is not H, —CN or halogen, it is optionally substituted with one or more halogens;
each $R^2$ is independently H, halogen or $C_1$-$C_4$ straight or branched alkyl;
$R^3$ is H, —OH, or halogen;
$R^{21}$ is cyclobutyl, azetidin-1-yl, or cyclopropyl;
$R^{22}$ is H, halogen, or $C_1$-$C_2$ alkyl;
$R^{35}$ is —C(O)—$R^{351}$, —C(O)—NHR$^{351}$, —C(O)—O—$R^{351}$ or S(O)$_2$R$^{351}$; and
$R^{351}$ is $C_1$-$C_6$ straight or branched alkyl, cycloalkyl, heterocyclyl, aryl or heteroaryl, each of which is optionally substituted.

In some aspects of Structure (VI-J), $R^3$ is H or halogen.
In some aspects of Structure (VI-J), $R^1$ is halogen, —CN or $C_1$-$C_2$ haloalkyl.
In some aspects of Structure (VI-J), $R^{22}$ is $C_1$-$C_2$ alkyl.
In some aspects of Structure (VI-J), $R^{21}$ is cyclobutyl and $R^{22}$ is $C_1$-$C_2$ alkyl.
In some aspects of Structure (VI-J), $R^{21}$ is cyclobutyl.
In some aspects of Structure (VI-J), $R^3$ is H or F.
In some aspects of Structure (VI-J), $R^1$ is —CN.
In some aspects of Structure (VI-J), $R^1$ is —CF$_3$.
In some aspects of Structure (VI-J), $R^{22}$ is H, methyl or ethyl.
In some aspects of Structure (VI-J), $R^{22}$ is H.
In some aspects of Structure (VI-J), $R^{22}$ is methyl.
In some aspects of Structure (VI-J), $R^{35}$ is —C(O)—NHR$^{351}$.

In some aspects of Structure (VI-J), $R^{351}$ is isopropyl, isobutyl, (R)-3-tetrahydrofuranyl, (S)-3-tetrahydrofuranyl, (R)-(tetrahydrofuran-2-yl)methyl, (S)-(tetrahydrofuran-2-yl)methyl, (R)-tetrahydro-2H-pyran-3-yl or (S)-tetrahydro-2H-pyran-3-yl.

In some aspects of Structure (VI-J), $R^{351}$ is (R)-(tetrahydrofuran-2-yl)methyl or (S)-(tetrahydrofuran-2-yl)methyl.

In some aspects of Structure (VI-J), $R^1$ is —CN, each $R^2$ is H, $R^3$ is H or F, $R^{21}$ is $C_3$-$C_4$ cycloalkyl, $R^{22}$ is H, $R^{35}$ is —C(O)—NHR$^{351}$ where $R^{351}$ is isopropyl, isobutyl, (R)-3-tetrahydrofuranyl, (S)-3-tetrahydrofuranyl, (R)-(tetrahydrofuran-2-yl)methyl, (S)-(tetrahydrofuran-2-yl)methyl, (R)-tetrahydro-2H-pyran-3-yl, or (S)-tetrahydro-2H-pyran-3-yl.

In some aspects of Structure (VI-J), $R^{35}$ is —C(O)—O—R$^{351}$.

In some aspects of Structure (VI-J), $R^{351}$ is isopropyl, isobutyl, (R)-3-tetrahydrofuranyl, (S)-3-tetrahydrofuranyl, (R)-(tetrahydrofuran-2-yl)methyl, (S)-(tetrahydrofuran-2-yl)methyl, (R)-tetrahydro-2H-pyran-3-yl, or (S)-tetrahydro-2H-pyran-3-yl.

In some aspects of Structure (VI-J), $R^1$ is —CN, each $R^2$ is H, $R^3$ is H or F, $R^{21}$ is $C_3$-$C_4$ cycloalkyl, $R^{22}$ is H, $R^{35}$ is —C(O)—O—R$^{351}$ where $R^{351}$ is isopropyl, isobutyl, (R)-3-tetrahydrofuranyl, (S)-3-tetrahydrofuranyl, (R)-(tetrahydrofuran-2-yl)methyl, (S)-(tetrahydrofuran-2-yl)methyl, (R)-tetrahydro-2H-pyran-3-yl, or (S)-tetrahydro-2H-pyran-3-yl.

In some aspects of Structure (VI-J), $R^{351}$ is (R)-3-tetrahydrofuranyl or (S)-3-tetrahydrofuranyl.

In some aspects of Structure (VI-J), compounds have a structure selected from the group consisting of:

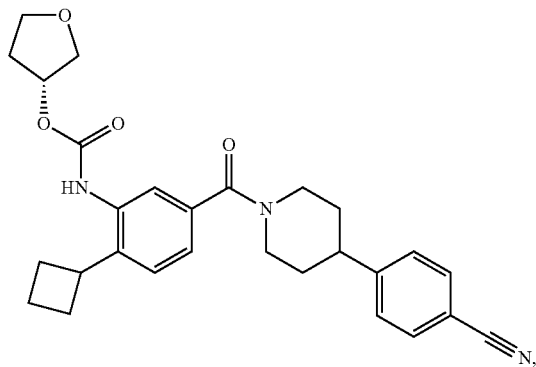

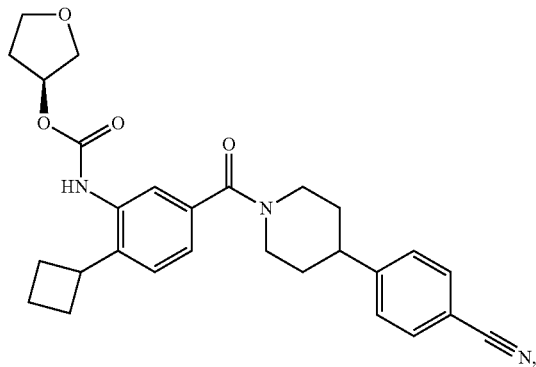

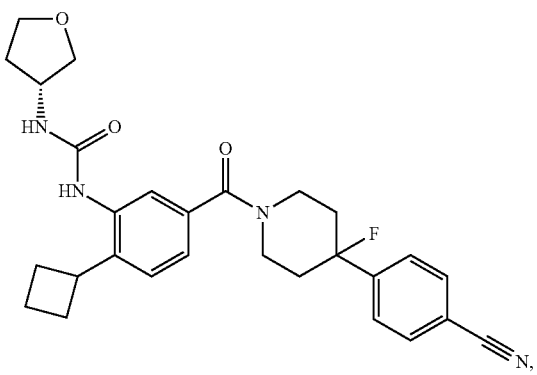

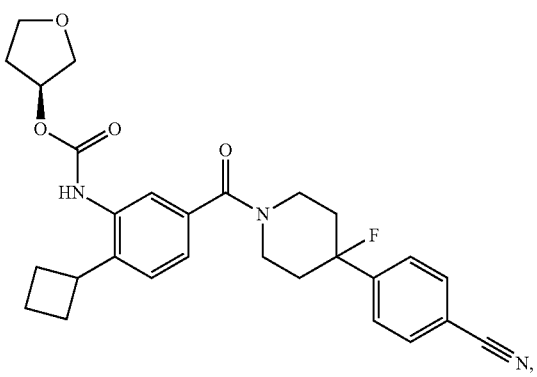

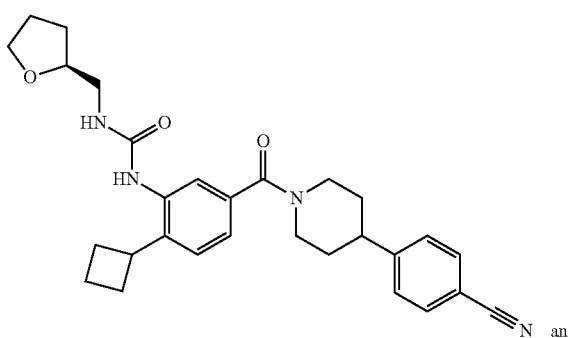

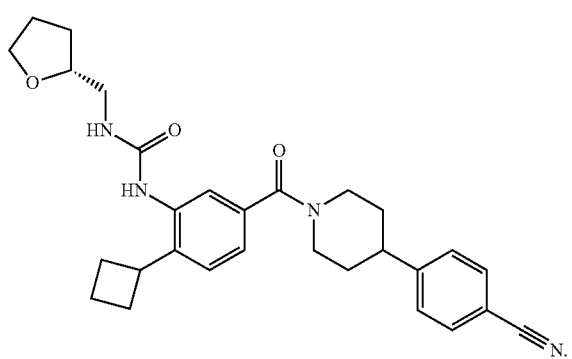

Compounds of Structure (VII)

In certain aspects, the compounds of Structure (VII) have one of the following Structures (VII-A) or (VII-B):

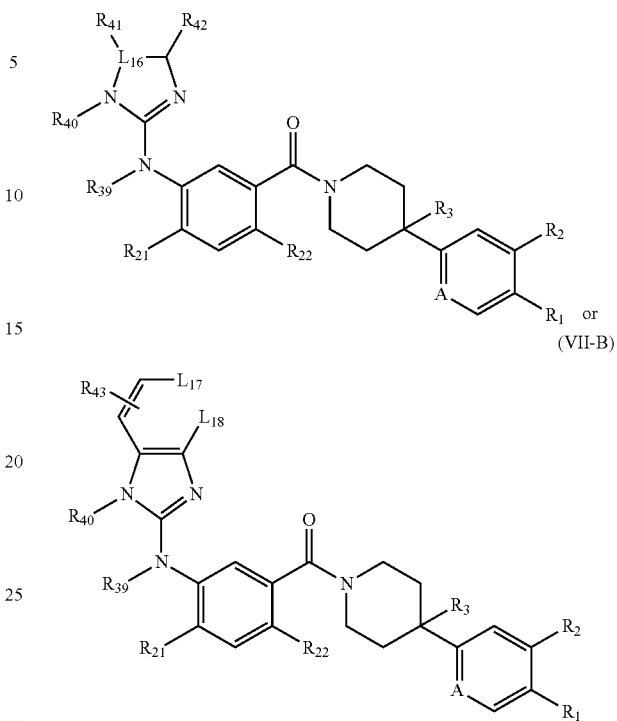

or a pharmaceutically acceptable salt thereof, wherein:
$L_{16}$ is C or N, wherein $R_{41}$ is absent if $L_{16}$ is N;
$L_{17}$, $L_{18}$, and A are each independently CH or N;
$R_1$ is hydrogen, cyano, halo, $C_{1-6}$ alkyl, $C_{1-6}$ alkoxy, —C(=O)N($R_{13}$)($R_{14}$), —(CH$_2$)$_q$C(=O)N($R_{13}$)($R_{14}$), $CF_3$, —$OCF_3$, or —S(=O)$_2R_{20}$;
q is 0, 1, 2, 3, or 4;
$R_{20}$ is hydrogen or $C_{1-6}$ alkyl, $C_{1-6}$ alkoxy, or —N($R_{13}$)($R_{14}$);
$R_2$ is hydrogen, halo, $C_{1-6}$ alkoxy, or $C_{1-6}$ alkyl;
$R_3$ is hydrogen, hydroxyl, halo, $C_{1-6}$ alkyl, or $C_{1-6}$ alkoxy;
$R_{21}$ and $R_{22}$ are each independently hydrogen, halo, cyano, $C_{1-6}$ alkyl, $C_{1-6}$ alkoxy, $CF_3$, —$OCF_3$, or —S(=O)$_2R_{20}$;
$R_{40}$, $R_{42}$, and $R_{43}$ are each independently hydrogen, $C_{1-6}$ alkyl, $C_{1-6}$ alkoxy, —S(=O)$_2R_{20}$, —C(=O)R, hydroxyalkyl, hydroxyl, —N($R_{13}R_{14}$), or $R_{41}$ and $R_{42}$ taken together with the atoms to which they are attached join together to form a heteroaryl or heterocyclyl;
$R_{41}$ is hydrogen, $C_{1-6}$ alkyl, $C_{1-6}$ alkoxy, —S(=O)$_2R_{20}$, —C(=O)R, hydroxyalkyl, hydroxyl, —N($R_{13}R_{14}$), $R_{41}$ is absent if $L_{16}$ is N, or $R_{41}$ and $R_{42}$ taken together with the atoms to which they are attached join together to form a heteroaryl or heterocyclyl;
R is hydrogen, $C_{1-6}$ alkyl, cycloalkyl, aryl, heterocyclyl, heteroaryl, hydroxyalkyl, —N($R_{15}R_{16}$), or —S(=O)$_2R_{20}$;
$R_{39}$ is hydrogen, $C_{1-6}$ alkyl, or $C_{1-6}$ alkoxy;
$R_{13}$ and $R_{14}$ are each independently hydrogen, $C_{1-6}$ alkyl, cycloalkyl, aryl, heterocyclyl, heteroaryl, hydroxyalkyl, alkylamino, —N($R_{15}R_{16}$), or —S(=O)$_2R_{20}$; and
$R_{15}$ and $R_{16}$ are each independently hydrogen, $C_{1-6}$ alkyl, cycloalkyl, aryl, heterocyclyl, heteroaryl, hydroxyalkyl, or alkylamino.

In certain aspects of Structure (VII), $R_1$ is hydrogen, cyano, $C_{1-6}$ alkyl, $C_{1-6}$ alkoxy, or —C(=O)N($R_{13}$)($R_{14}$).

In certain aspects of Structure (VII), $R_1$ is cyano.

In certain aspects of Structure (VII), $R_2$ is hydrogen or halo.

In certain aspects of Structure (VII), $R_2$ is hydrogen.

In certain aspects of Structure (VII), $R_3$ is hydrogen.

In certain aspects of Structure (VII), $R_{21}$ and $R_{22}$ are each independently hydrogen or $C_{1-6}$ alkyl.

In certain aspects of Structure (VII), $R_{21}$ and $R_{22}$ are each independently $C_{1-6}$ alkyl.

In certain aspects of Structure (VII), $R_{39}$ is hydrogen.

In certain aspects of Structure (VII), $R_{40}$ is hydrogen.

In certain aspects of Structure (VII), $L_{16}$ is N.

In certain aspects of Structure (VII), $L_{17}$ is N.

In certain aspects of Structure (VII), $L_{18}$ is CH.

In certain aspects of Structure (VII), $L_{18}$ is N.

In certain aspects of Structure (VII), A is N.

In certain aspects of Structure (VII), A is CH.

In certain aspects of Structure (VII), $R_{42}$ is $C_{1-6}$ alkyl.

In certain aspects of Structure (VII), $R_{41}$ is $C_{1-6}$ alkyl.

In certain aspects, the compounds of Structure (VII) have one of the following Structures (VII-C) or (VII-D):

(VII-C)

(VII-D)

or a pharmaceutically acceptable salt thereof.

Compounds of Structure (VIII)

In certain aspects, the compounds of Structure (VIII) have one of the following Structures (VIII-A), (VIII-B), or (VIII-C):

(VIII-A)

(VIII-B)

(VIII-C)

or a pharmaceutically acceptable salt thereof, wherein:

$L_{19}$ and A are each independently CH or N;

$R_1$ is hydrogen, cyano, halo, $C_{1-6}$ alkyl, $C_{1-6}$ alkoxy, —C(=O)N($R_{13}$)($R_{14}$), —(CH$_2$)$_q$C(=O)N($R_{13}$)($R_{14}$), CF$_3$, —OCF$_3$, or —S(=O)$_2$R$_{20}$;

q is 0, 1, 2, 3, or 4;

$R_{20}$ is hydrogen or $C_{1-6}$ alkyl, $C_{1-6}$ alkoxy, or —N($R_{13}$)($R_{14}$);

$R_2$ is hydrogen, halo, $C_{1-6}$ alkoxy, or $C_{1-6}$ alkyl;

$R_3$ is hydrogen, hydroxyl, halo, $C_{1-6}$ alkyl, or $C_{1-6}$ alkoxy;

$R_{21}$ and $R_{22}$ are each independently hydrogen, halo, cyano, $C_{1-6}$ alkyl, $C_{1-6}$ alkoxy, CF$_3$, —OCF$_3$, or —S(=O)$_2$R$_{20}$;

$R_{39}$ is hydrogen, $C_{1-6}$ alkyl, or $C_{1-6}$ alkoxy;

$R_{44}$ and $R_{45}$ are each independently hydrogen, $C_{1-6}$ alkyl, $C_{1-6}$ alkoxy, cycloalkyl, hydroxyalkyl, aryl, heterocyclyl, heteroaryl, alkylamino, —S(=O)$_2$R$_{20}$, —C(=O)R, or —N($R_{13}R_{14}$); and $R_{13}$ and $R_{14}$ are each independently hydrogen, $C_{1-6}$ alkyl, cycloalkyl, aryl, heterocyclyl, heteroaryl, hydroxyalkyl, alkylamino, —N($R_{15}R_{16}$), or —S(=O)$_2$R$_{20}$; and $R_{15}$ and $R_{16}$ are each independently hydrogen, $C_{1-6}$ alkyl, cycloalkyl, aryl, heterocyclyl, heteroaryl, hydroxyalkyl, or alkylamino.

In certain aspects of Structure (VIII), $R_1$ is hydrogen, cyano, $C_{1-6}$ alkyl, $C_{1-6}$ alkoxy, or —C(=O)NN($R_{13}$)($R_{14}$).

In certain aspects of Structure (VIII), $R_1$ is cyano.

In certain aspects of Structure (VIII), $R_2$ is hydrogen or halo.

In certain aspects of Structure (VIII), $R_2$ is hydrogen.

In certain aspects of Structure (VIII), $R_3$ is hydrogen.

In certain aspects of Structure (VIII), $R_{21}$ and $R_{22}$ are each independently hydrogen or $C_{1-6}$ alkyl.

In certain aspects of Structure (VIII), $R_{21}$ and $R_{22}$ are each independently $C_{1-6}$ alkyl.

In certain aspects of Structure (VIII), $R_{39}$ is hydrogen.

In certain aspects of Structure (VIII), $L_{19}$ is N.

In certain aspects of Structure (VIII), A is N.

In certain aspects of Structure (VIII), A is CH.

In certain aspects, the compounds of Structure (VIII) have the following Structure (VIII-D):

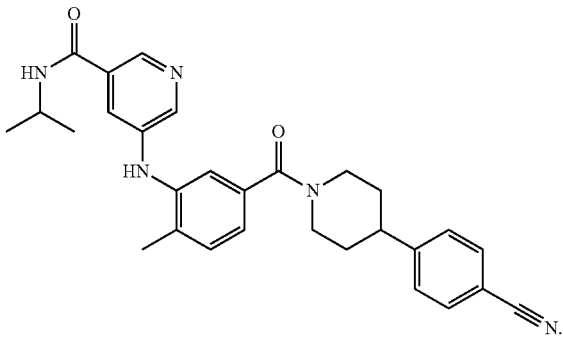

(VIII-D)

or a pharmaceutically acceptable salt thereof.

In various aspects, compounds of formula IX are provided:

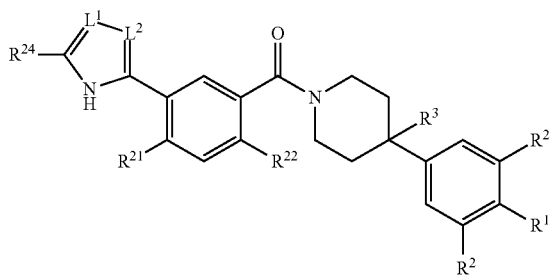

(IX)

or a pharmaceutically acceptable salt thereof, wherein:
$R^1$ is H, —CN, halogen, $C_1$-$C_4$ straight or branched alkyl, —O—($C_3$-$C_5$ cycloalkyl) or —O—($C_1$-$C_4$ straight or branched alkyl) wherein:
  $C_3$-$C_5$ cycloalkyl optionally includes an oxygen or nitrogen heteroatom; and
  when $R^1$ is not H, —CN or halogen, it is optionally substituted with one or more halogens;
each $R^2$ is independently hydrogen, halogen or $C_1$-$C_4$ straight or branched alkyl;
$R^3$ is H, —OH, or halogen;

$R^{21}$ is H, halogen, $C_1$-$C_4$ straight or branched alkyl, $C_3$-$C_5$ cycloalkyl wherein the $C_3$-$C_5$ cycloalkyl optionally includes an oxygen or nitrogen heteroatom;
$R^{22}$ is H, halogen, or $C_1$-$C_2$ alkyl;
$R^{24}$ is H, $C_1$-$C_4$ straight or branched alkyl, —($C_1$-$C_4$ alkyl)$_t$-OH, —($C_1$-$C_4$ alkyl)$_t$-O—($C_3$-$C_5$ cycloalkyl), or —($C_1$-$C_4$ alkyl)$_t$-O—($C_1$-$C_4$ straight or branched alkyl) wherein:
  t is 0 or 1;
  the $C_3$-$C_5$ cycloalkyl optionally includes an oxygen or nitrogen heteroatom;
$L^1$ is $CR^{23}$ or N;
$L^2$ is CH or N;
at least one of $L^1$ or $L^2$ is N; and
$R^{23}$ is H or $C_1$-$C_4$ straight or branched alkyl.

In some aspects of Structure (IX), $R^{24}$ is $C_1$-$C_4$ straight or branched alkyl, —($C_1$-$C_4$ alkyl)$_t$-O—($C_1$-$C_4$ straight or branched alkyl) wherein t is 0 or 1.

In some aspects of Structure (IX), $R^{21}$ is halogen, $C_1$-$C_4$ straight or branched alkyl, $C_3$-$C_5$ cycloalkyl wherein the $C_3$-$C_5$ cycloalkyl optionally includes an oxygen or nitrogen heteroatom, —S(O)$_u$—($C_1$-$C_4$ straight or branched alkyl) wherein u is 0 or 2, or —S(O)$_u$—($C_3$-$C_5$ cycloalkyl) wherein u is 0 or 2;

In some aspects of Structure (IX), $R^3$ is H or halogen.

In some aspects of Structure (IX), $R^1$ is halogen, —CN or $C_1$-$C_2$ haloalkyl.

In some aspects of Structure (IX), both $L^1$ and $L^2$ are N.

In some aspects of Structure (IX), $R^{21}$ is $C_1$-$C_2$ alkyl or $C_3$-$C_5$ cycloalkyl and $R^{22}$ is $C_1$-$C_2$ alkyl.

In some aspects of Structure (IX), $R^{21}$ is $C_3$-$C_5$ cycloalkyl and $R^{22}$ is $C_1$-$C_2$ alkyl.

In some aspects of Structure (IX), $R^{24}$ is —($C_1$-$C_2$ alkyl)$_t$-O—($C_1$-$C_2$ alkyl) wherein t is 0 or 1.

In some aspects of Structure (IX), $R^{21}$ is $C_3$-$C_5$ cycloalkyl, $R^{22}$ is $C_1$-$C_2$ alkyl and $R^{24}$ is $C_1$-$C_2$ alkyl.

In some aspects of Structure (IX), $R^{21}$ is cyclobutyl, $R^{22}$ is $C_1$-$C_2$ alkyl and $R^{24}$ is $C_1$-$C_2$ alkyl.

In some aspects of Structure (IX), $R^{21}$ is cyclobutyl.

In some aspects of Structure (IX), $R^3$ is H or F.

In some aspects of Structure (IX), $R^1$ is —CN.

In some aspects of Structure (IX), $R^1$ is —CF$_3$.

In some aspects of Structure (IX), $R^{22}$ is H, methyl or ethyl.

In some aspects of Structure (IX), $R^{22}$ is H.

In some aspects of Structure (IX), $R^{22}$ is methyl.

In some aspects of Structure (IX), $R^1$ is —CN, each $R^2$ is hydrogen, $R^3$ is H or F, $R^{21}$ is $C_3$-$C_4$ cycloalkyl, $R^{22}$ is methyl, $L^1$ and $L^2$ are N, and $R^{24}$ is methyl, ethyl, hydroxymethyl, methoxymethyl, 2-methoxyethyl.

In some aspects of Structure (IX), $R^1$ is —CN, each $R^2$ is H, $R^3$ is H or F, $R^{21}$ is $C_3$-$C_4$ cycloalkyl, $R^{22}$ is methyl, $L^1$ and $L^2$ are N, and $R^{24}$ is methoxy or ethoxy.

In some aspects of Structure (IX), $R^1$ is —CN, each $R^2$ is H, $R^3$ is H or F, $R^{21}$ is $C_3$-$C_4$ cycloalkyl, $R^{22}$ is methyl, $L^1$ is CH, $L^2$ is N, and $R^{24}$ is methyl, ethyl, hydroxymethyl, methoxymethyl, or 2-methoxyethyl.

In some aspects of Structure (IX), $R^1$ is —CN, each $R^2$ is H, $R^3$ is H or F, $R^{21}$ is $C_3$-$C_4$ cycloalkyl, $R^{22}$ is methyl, $L^1$ is N, $L^2$ is CH, and $R^{24}$ is methyl, ethyl, hydroxymethyl, methoxymethyl, or 2-methoxyethyl.

In some aspects of Structure (IX), compounds have a structure selected from the group consisting of:

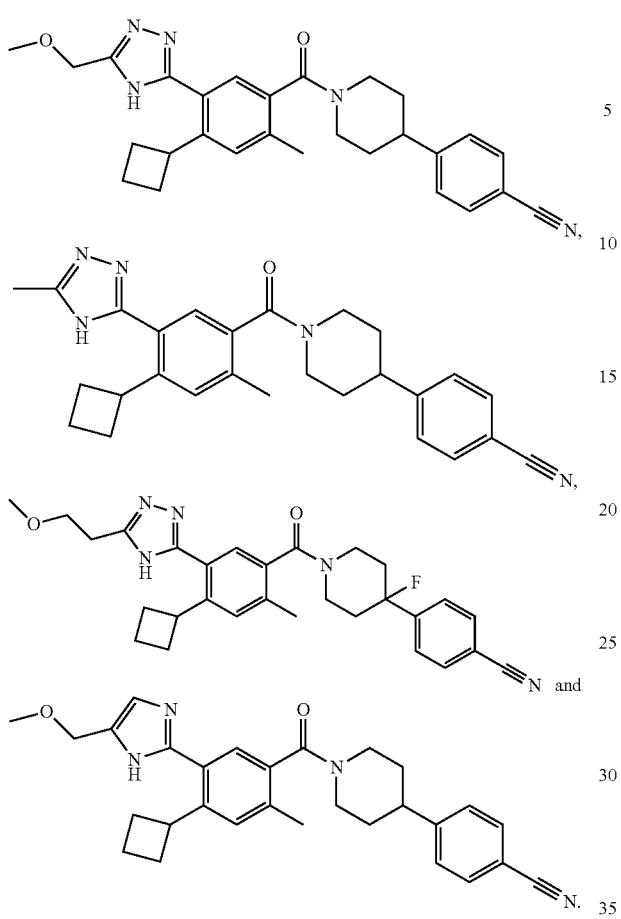

In various aspects, compounds of Structure (X) are provided:

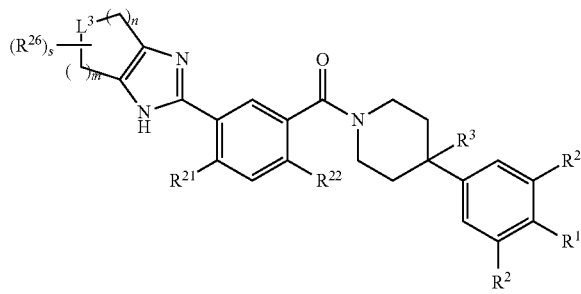

or a pharmaceutically acceptable salt thereof, wherein:
$R^1$ is H, —CN, halogen, $C_1$-$C_4$ straight or branched alkyl, —O—($C_3$-$C_5$ cycloalkyl), —O—($C_1$-$C_4$ straight or branched alkyl) wherein:
  the $C_3$-$C_5$ cycloalkyl optionally includes an oxygen or nitrogen heteroatom; and
  when $R^1$ is not H, —CN or halogen, it is optionally substituted with one or more halogens;
each $R^2$ is independently hydrogen, halogen or $C_1$-$C_4$ straight or branched alkyl;
$R^3$ is H, —OH or halogen;
$L^3$ is C($R^{60}$)$_2$, O or NR$^{50}$;

each $R^{60}$ is independently H, —OH, —CN, —O$_t$—($C_3$-$C_5$ cycloalkyl), —O—($C_1$-$C_4$ straight or branched alkyl), or —C(O)—N($R^{601}$)$_2$ wherein:
  t is 0 or 1, and
  the $C_3$-$C_5$ cycloalkyl optionally includes an oxygen or nitrogen heteroatom;
each $R^{50}$ is independently H, —C(O)—O$_t$—($C_1$-$C_4$ straight or branched alkyl), —C(O)—O$_t$—($C_3$-$C_5$ cyclic alkyl), —$C_3$-$C_5$ cyclic alkyl optionally containing an oxygen or nitrogen heteroatom, —C(O)—N($R^{501}$)$_2$, $C_1$-$C_4$ straight or branched alkyl wherein:
  t is 0 or 1, and
  the $C_3$-$C_5$ cycloalkyl optionally includes an oxygen or nitrogen heteroatom;
n is 1, 2 or 3;
m is 1 or 2;
$R^{21}$ is H, halogen, $C_1$-$C_4$ straight or branched alkyl, $C_3$-$C_5$ cycloalkyl wherein the $C_3$-$C_5$ cycloalkyl optionally includes an oxygen or nitrogen heteroatom
$R^{22}$ is H, halogen, $C_1$-$C_2$ alkyl;
each $R^{26}$ is independently —OH, —CN, halogen, $C_1$-$C_4$ straight or branched alkyl, —($C_1$-$C_4$ alkyl)$_t$-O$_t$—($C_3$-$C_5$ cycloalkyl), —($C_1$-$C_4$ alkyl)$_t$-O—($C_1$-$C_4$ straight or branched alkyl), —C(O)—O$_t$—($C_1$-$C_4$ alkyl), or —C(O)—N($R^{501}$)$_2$ wherein:
  t is 0 or 1, and
  the $C_3$-$C_5$ cycloalkyl optionally includes an oxygen or nitrogen heteroatom;
s is 0, 1 or 2;
each $R^{601}$ and $R^{501}$ is independently H or $C_1$-$C_4$ straight or branched alkyl; and
wherein two of $R^{26}$, $R^{60}$, $R^{50}$, $R^{501}$ and $R^{601}$ optionally join to form a ring wherein the two of $R^{26}$, $R^{60}$, $R^{50}$, $R^{501}$ and $R^{601}$ may be two $R^{26}$, two $R^{60}$, two $R^{50}$, two $R^{501}$, two $R^{601}$.

In some aspects of Structure (X), $R^{21}$ is halogen, $C_1$-$C_4$ straight or branched alkyl or $C_3$-$C_5$ cycloalkyl.
In some aspects of Structure (X), $R^3$ is H or halogen.
In some aspects of Structure (X), $R^1$ is —CN or $C_1$-$C_2$ haloalkyl.
In some aspects of Structure (X), $R^3$ is H or F.
In some aspects of Structure (X), $R^1$ is —CN.
In some aspects of Structure (X), $R^1$ is —CF$_3$.
In some aspects of Structure (X), n is 1.
In some aspects of Structure (X), n is 2.
In some aspects of Structure (X), m is 1
In some aspects of Structure (X), m is 2.
In some aspects of Structure (X), $R^{21}$ is $C_1$-$C_2$ alkyl or $C_3$-$C_5$ cycloalkyl and $R^{22}$ is $C_1$-$C_2$ alkyl.
In some aspects of Structure (X), $R^{21}$ is $C_3$-$C_5$ cycloalkyl and $R^{22}$ is $C_1$-$C_2$ alkyl.
In some aspects of Structure (X), n is 2, m is 1, $L^3$ is —N—C(O)—O—($C_1$-$C_2$ alkyl).
In some aspects of Structure (X), $L^3$ is NR$^{50}$; $R^{50}$ is $C_1$-$C_2$ alkyl; $R^{21}$ is cyclobutyl; $R^{22}$ is H or methyl; $R^3$ is H; $R^1$ is —CN; m is 2 and n is 1 or 2.
In some aspects of Structure (X), n is 2, m is 1, $L^3$ is O and s is 0.
In some aspects of Structure (X), $R^{22}$ is H, methyl or ethyl.
In some aspects of Structure (X), $R^{22}$ is methyl.
In some aspects of Structure (X), $R^{22}$ is H.
In some aspects of Structure (X), $R^1$ is —CN, each $R^2$ is H, $R^3$ is H or F, $R^{21}$ is $C_3$-$C_4$ cycloalkyl, $R^{22}$ is methyl, n is 2 and $L^3$ is NR$^{50}$ where $R^{50}$ is methyl or ethyl.

In some aspects of Structure (X), $R^1$ is —CN, each $R^2$ is H, $R^3$ is H or F, $R^{21}$ is $C_3$-$C_4$ cycloalkyl, $R^{22}$ is methyl, n is 2 and $L^3$ is O.

In some aspects of Structure (X), the compound has a structure selected from the group consisting of:

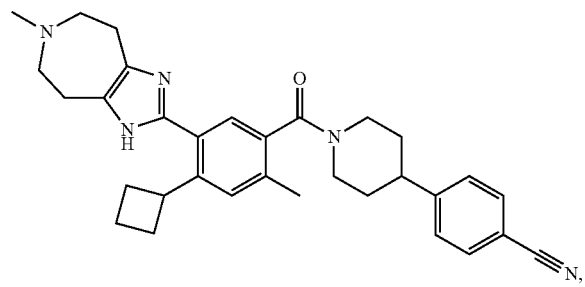

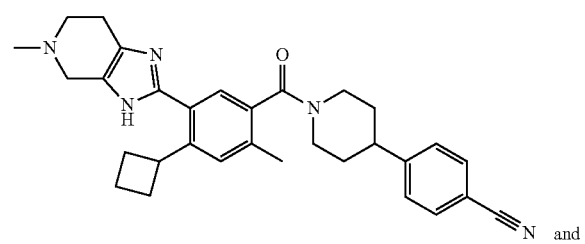
and

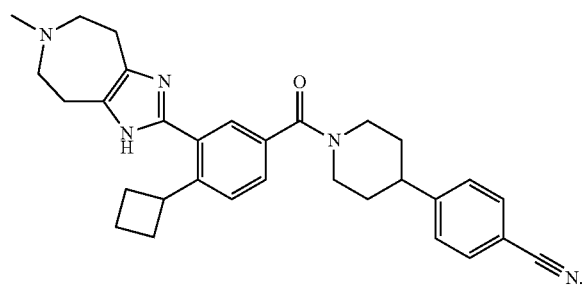

In various aspects, compounds of Structure (XI) are provided:

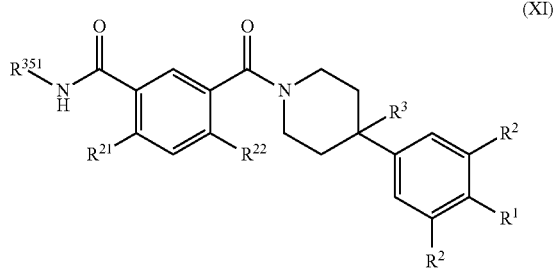

(XI)

or a pharmaceutically acceptable salt thereof, wherein:
$R^1$ is H, —CN, halogen, $C_1$-$C_4$ straight or branched alkyl, —O—($C_3$-$C_5$ cycloalkyl), —O—($C_1$-$C_4$ straight or branched alkyl) wherein:
the $C_3$-$C_5$ cycloalkyl optionally includes an oxygen or nitrogen heteroatom; and
when $R^1$ is not H, —CN or halogen, it is optionally substituted with one or more halogens;

each $R^2$ is independently H, halogen or $C_1$-$C_4$ straight or branched alkyl;
$R^3$ is H, —OH, or halogen;
$R^{21}$ is cyclobutyl, azetidin-1-yl, or cyclopropyl;
$R^{22}$ is H, halogen, $C_1$-$C_2$ alkyl; and
$R^{351}$ is $C_1$-$C_2$ alkyl or $C_2$—O—($C_1$ or $C_2$ alkyl).

In some aspects of Structure (XI), $R^3$ is H or halogen.
In some aspects of Structure (XI), $R^1$ is halogen, —CN or $C_1$-$C_2$ haloalkyl.
In some aspects of Structure (XI), $R^{21}$ is $C_3$-$C_4$ cycloalkyl and $R^{22}$ is $C_1$-$C_2$ alkyl.
In some aspects of Structure (XI), $R^{21}$ is cyclobutyl and $R^{22}$ is $C_1$-$C_2$ alkyl.
In some aspects of Structure (XI), $R^{21}$ is cyclobutyl.
In some aspects of Structure (XI), $R^3$ is H or F.
In some aspects of Structure (XI), $R^1$ is —CN.
In some aspects of Structure (XI), $R^1$ is —CF$_3$.
In some aspects of Structure (XI), $R^{22}$ is H, methyl or ethyl.
In some aspects of Structure (XI), $R^{22}$ is H.
In some aspects of Structure (XI), $R^{22}$ is methyl.
In some aspects of Structure (XI), $R^1$ is —CN, each $R^2$ is H, $R^3$ is H or F, $R^{21}$ is cyclobutyl, $R^{22}$ is methyl and $R^{351}$ is methyl or ethyl.

In some aspects of Structure (XI), the compound has a structure selected from the group consisting of:

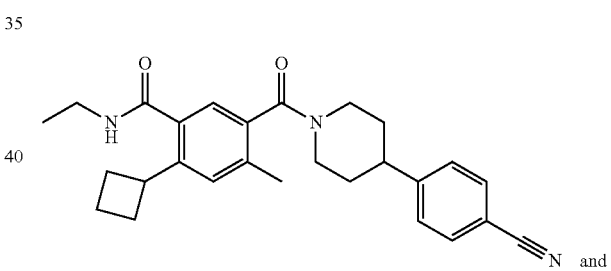
and

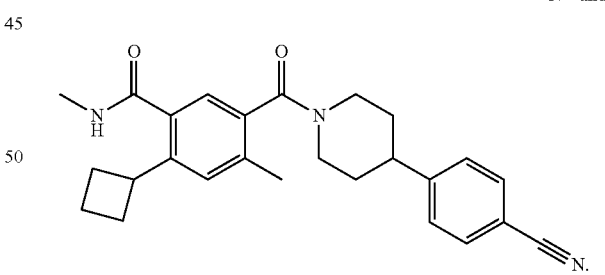

In certain aspects, the present disclosure provides compounds having any one of the structures found in Table 1. According to the present disclosure, the compounds of Table 1 are inhibitors of fatty acid synthase.

Synthesis of Compounds

Also described herein are methods of synthesizing the compounds of the present disclosure. Compounds of the present disclosure can be synthesized as indicated in SYNTHETIC SCHEMES 1-13 below.

Scheme 1
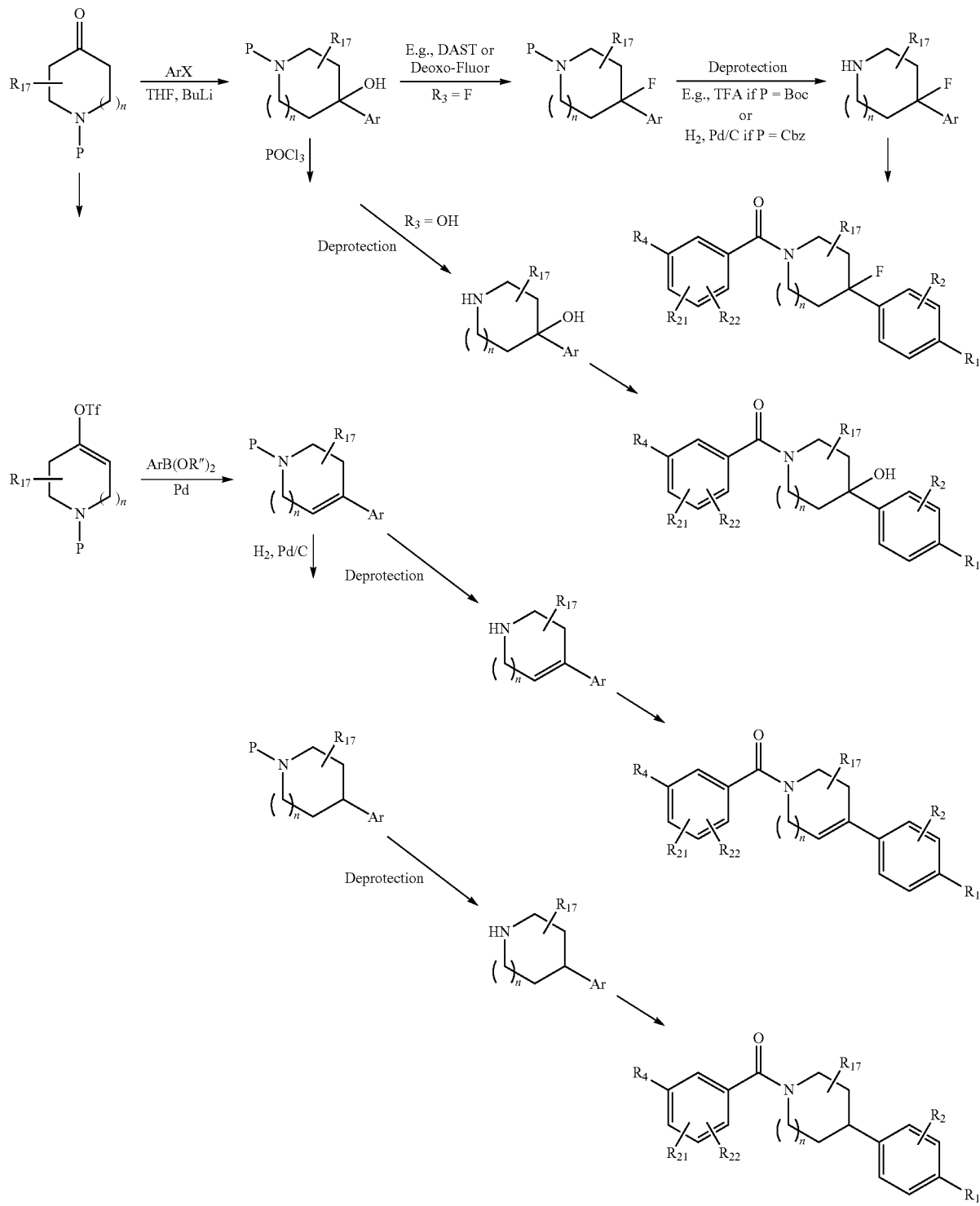
wherein:
R" is hydrogen or alkyl;
R$_1$ is hydrogen, cyano, halo, C$_{1-6}$ alkyl, C$_{1-6}$ alkoxy, —C(=O)N(R$_{13}$)(R$_{14}$), —(CH$_2$)$_q$C(=O)N(R$_{13}$)(R$_{14}$), CF$_3$, —OCF$_3$, or —S(=O)$_2$R$_{20}$;
q is 0, 1, 2, 3, or 4;
R$_{20}$ is hydrogen or C$_{1-6}$ alkyl, C$_{1-6}$ alkoxy, or —N(R$_{13}$)(R$_{14}$);
R$_2$ is hydrogen, halo, C$_{1-6}$ alkoxy, or C$_{1-6}$ alkyl;

$R_3$ is hydrogen, hydroxyl, halo, $C_{1-6}$ alkyl, or $C_{1-6}$ alkoxy;

$R_{21}$ and $R_{22}$ are each independently hydrogen, halo, cyano, $C_{1-6}$ alkyl, $C_{1-6}$ alkoxy, $CF_3$, —$OCF_3$, or —$S(=O)_2R_{20}$;

$R_{13}$ and $R_{14}$ are each independently hydrogen, $C_{1-6}$ alkyl, cycloalkyl, aryl, heterocyclyl, heteroaryl, hydroxyalkyl, alkylamino, —$N(R_{15}R_{16})$, or —$S(=O)_2R_{20}$;

$R_{15}$ and $R_{16}$ are each independently hydrogen, $C_{1-6}$ alkyl, cycloalkyl, aryl, heterocyclyl, heteroaryl, hydroxyalkyl, or alkylamino; and $R_{17}$ is hydrogen or akyl.

Scheme 2

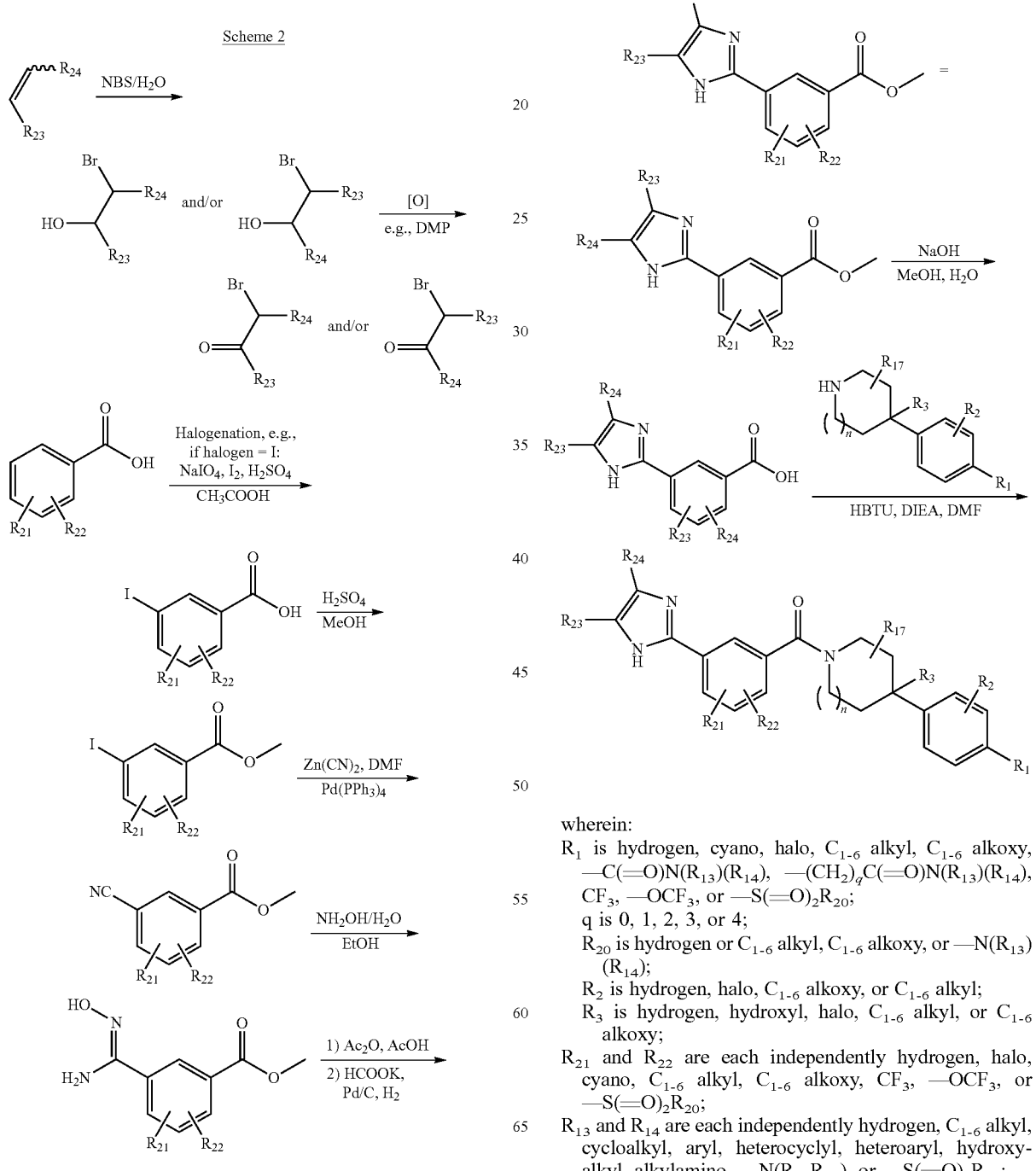

wherein:

$R_1$ is hydrogen, cyano, halo, $C_{1-6}$ alkyl, $C_{1-6}$ alkoxy, —$C(=O)N(R_{13})(R_{14})$, —$(CH_2)_qC(=O)N(R_{13})(R_{14})$, $CF_3$, —$OCF_3$, or —$S(=O)_2R_{20}$;

q is 0, 1, 2, 3, or 4;

$R_{20}$ is hydrogen or $C_{1-6}$ alkyl, $C_{1-6}$ alkoxy, or —$N(R_{13})(R_{14})$;

$R_2$ is hydrogen, halo, $C_{1-6}$ alkoxy, or $C_{1-6}$ alkyl;

$R_3$ is hydrogen, hydroxyl, halo, $C_{1-6}$ alkyl, or $C_{1-6}$ alkoxy;

$R_{21}$ and $R_{22}$ are each independently hydrogen, halo, cyano, $C_{1-6}$ alkyl, $C_{1-6}$ alkoxy, $CF_3$, —$OCF_3$, or —$S(=O)_2R_{20}$;

$R_{13}$ and $R_{14}$ are each independently hydrogen, $C_{1-6}$ alkyl, cycloalkyl, aryl, heterocyclyl, heteroaryl, hydroxyalkyl, alkylamino, —$N(R_{15}R_{16})$, or —$S(=O)_2R_{20}$;

$R_{15}$ and $R_{16}$ are each independently hydrogen, $C_{1-6}$ alkyl, cycloalkyl, aryl, heterocyclyl, heteroaryl, hydroxyalkyl, or alkylamino;

$R_{23}$ is hydrogen, —$N(R_{13})(R_{14})$, $C_{1-6}$ alkyl, $C_{1-6}$ alkoxy, is absent if $L_1$ is N, or $R_{23}$ and $R_{24}$ taken together with the atoms to which they are attached join together to form a heterocyclyl, heteroaryl, or cycloalkyl; and $R_{24}$ is hydrogen, —$N(R_{13})(R_{14})$, $C_{1-6}$ alkyl, $C_{1-6}$ alkoxy, —$(C_{1-6}$ alkoxy$)$(heterocyclyl), heterocyclyl, or $R_{23}$ and $R_{24}$ taken together with the atoms to which they are attached join together to form a heterocyclyl, heteroaryl, or cycloalkyl.

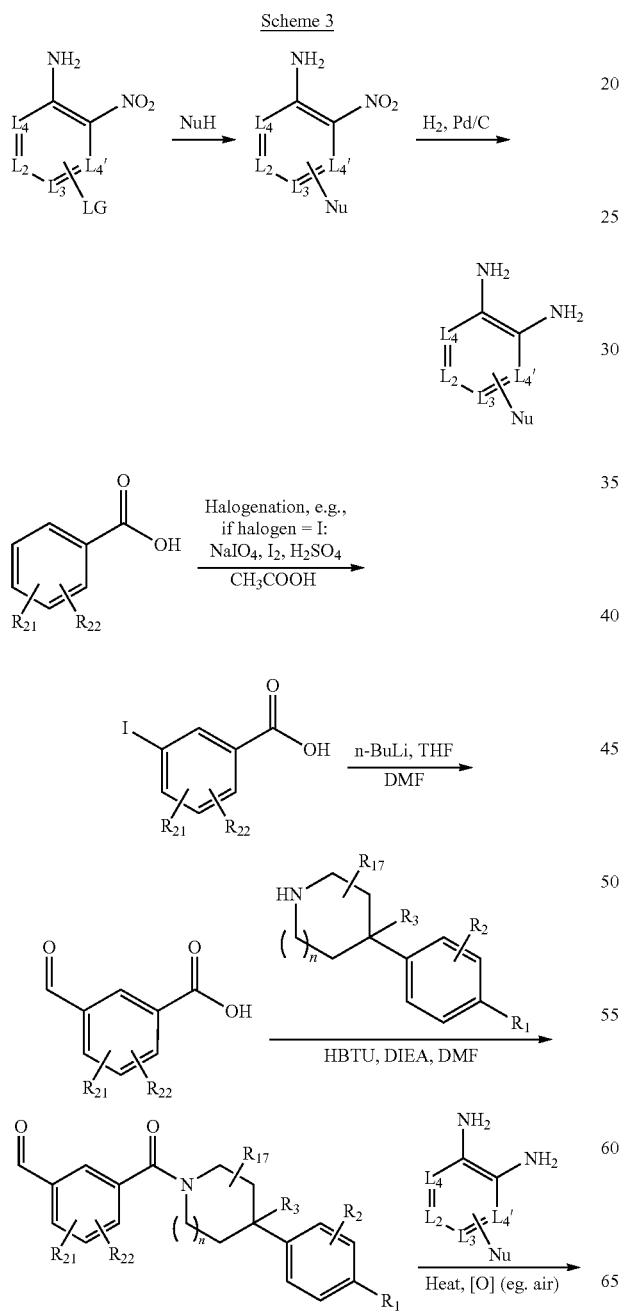

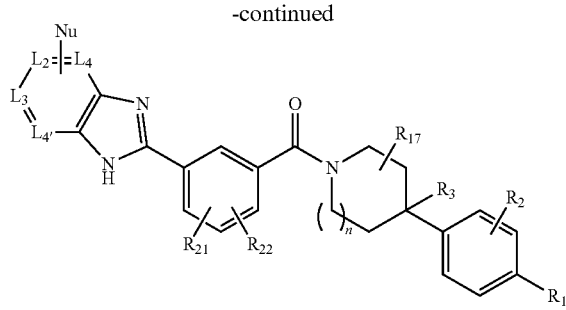

-continued wherein:

LG is a leaving group;

Nu is a nucleophile;

$L_2$, $L_3$, $L_4$, and $L_{4'}$ are each independently CH or N;

$R_1$ is hydrogen, cyano, halo, $C_{1-6}$ alkyl, $C_{1-6}$ alkoxy, —$C(=O)N(R_{13})(R_{14})$, —$(CH_2)_q(=O)N(R_{13})(R_{14})$, $CF_3$, —$OCF_3$, or —$S(=O)_2R_{20}$;

q is 0, 1, 2, 3, or 4;

$R_{20}$ is hydrogen or $C_{1-6}$ alkyl, $C_{1-6}$ alkoxy, or —$N(R_{13})(R_{14})$;

$R_2$ is hydrogen, halo, $C_{1-6}$ alkoxy, or $C_{1-6}$ alkyl;

$R_3$ is hydrogen, hydroxyl, halo, $C_{1-6}$ alkyl, or $C_{1-6}$ alkoxy;

$R_{21}$ and $R_{22}$ are each independently hydrogen, halo, cyano, $C_{1-6}$ alkyl, $C_{1-6}$ alkoxy, $CF_3$, —$OCF_3$, or —$S(=O)_2R_{20}$;

$R_{13}$ and $R_{14}$ are each independently hydrogen, $C_{1-6}$ alkyl, cycloalkyl, aryl, heterocyclyl, heteroaryl, hydroxyalkyl, alkylamino, —$N(R_{15}R_{16})$, or —$S(=O)_2R_{20}$;

$R_{15}$ and $R_{16}$ are each independently hydrogen, $C_{1-6}$ alkyl, cycloalkyl, aryl, heterocyclyl, heteroaryl, hydroxyalkyl, or alkylamino; and $R_{17}$ is hydrogen or alkyl.

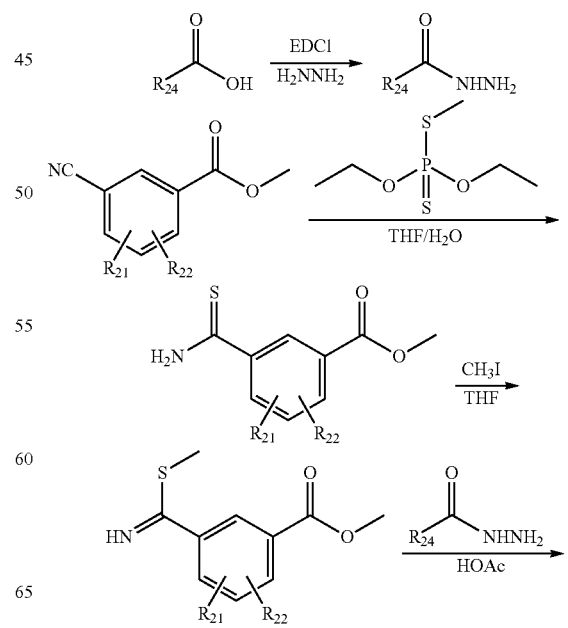

71

-continued

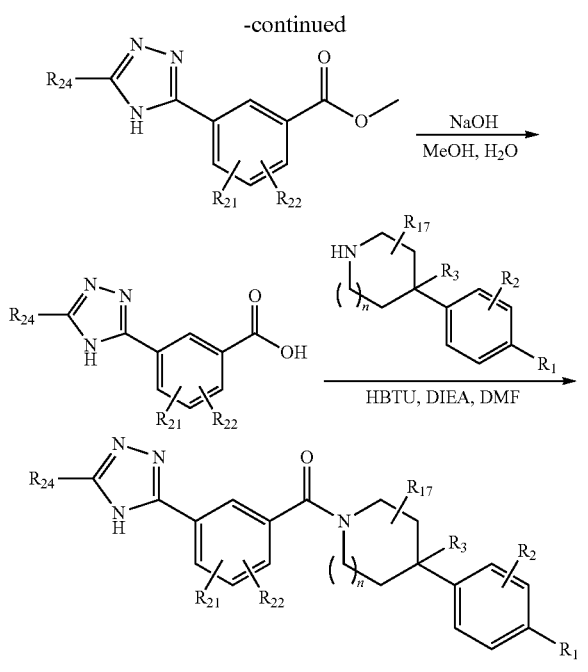

wherein:
R$_1$ is hydrogen, cyano, halo, C$_{1-6}$ alkyl, C$_{1-6}$ alkoxy, —C(=O)N(R$_{13}$)(R$_{14}$), —(CH$_2$)$_q$C(=O)N(R$_{13}$)(R$_{14}$), CF$_3$, —OCF$_3$, or —S(=O)$_2$R$_{20}$;
q is 0, 1, 2, 3, or 4;
R$_{20}$ is hydrogen or C$_{1-6}$ alkyl, C$_{1-6}$ alkoxy, or —N(R$_{13}$)(R$_{14}$);
R$_2$ is hydrogen, halo, C$_{1-6}$ alkoxy, or C$_{1-6}$ alkyl;
R$_3$ is hydrogen, hydroxyl, halo, C$_{1-6}$ alkyl, or C$_{1-6}$ alkoxy;
R$_{21}$ and R$_{22}$ are each independently hydrogen, halo, cyano, C$_{1-6}$ alkyl, C$_{1-6}$ alkoxy, CF$_3$, —OCF$_3$, or —S(=O)$_2$R$_{20}$;
R$_{13}$ and R$_{14}$ are each independently hydrogen, C$_{1-6}$ alkyl, cycloalkyl, aryl, heterocyclyl, heteroaryl, hydroxyalkyl, alkylamino, —N(R$_{15}$R$_{16}$), or —S(=O)$_2$R$_{20}$;
R$_{15}$ and R$_{16}$ are each independently hydrogen, C$_{1-6}$ alkyl, cycloalkyl, aryl, heterocyclyl, heteroaryl, hydroxyalkyl, or alkylamino;
R$_{17}$ is hydrogen or alkyl; and
R$_{24}$ is hydrogen, —N(R$_{13}$)(R$_{14}$), C$_{1-6}$ alkyl, —(C$_{1-6}$ alkoxy, alkoxy)(heterocyclyl), or heterocyclyl.

Scheme 5

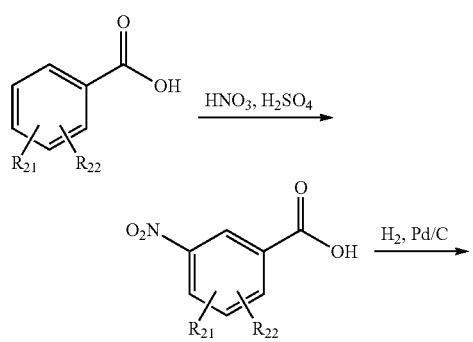

72

-continued

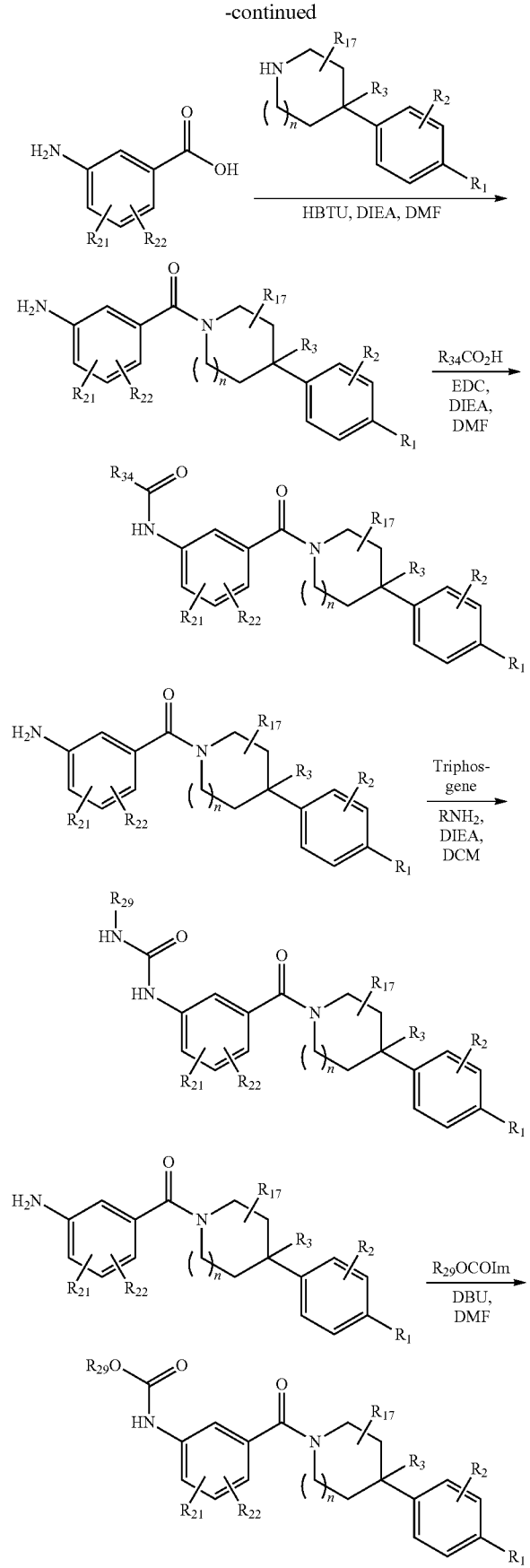

-continued m 0, 1, or 2.

Schemes 6-13 provides a synthesis for exemplary compounds of formula IX wherein:

$R^1$ is H, —CN, halogen, $C_1$-$C_4$ straight or branched alkyl, —O—($C_3$-$C_5$ cycloalkyl), —O—($C_1$-$C_4$ straight or branched alkyl) wherein:
  $C_3$-$C_5$ cycloalkyl optionally includes an oxygen or nitrogen heteroatom; and
  when $R^1$ is not H, —CN or halogen, it is optionally substituted with one or more halogens;

each $R^2$ is independently hydrogen, halogen or $C_1$-$C_4$ straight or branched alkyl;

$R^3$ is H, —OH, or halogen;

$R^{21}$ is H, halogen, $C_1$-$C_4$ straight or branched alkyl, $C_3$-$C_5$ cycloalkyl wherein the $C_3$-$C_5$ cycloalkyl optionally includes an oxygen or nitrogen heteroatom;

$R^{22}$ is H, halogen, or $C_1$-$C_2$ alkyl;

$R^{23}$ is H or $C_1$-$C_4$ straight or branched alkyl; and $R^{24}$ is H, $C_1$-$C_4$ straight or branched alkyl, —($C_1$-$C_4$ alkyl)$_t$-OH, —($C_1$-$C_4$ alkyl)$_t$-O$_t$—($C_3$-$C_5$ cycloalkyl), or —($C_1$-$C_4$ alkyl)$_t$-O—($C_1$-$C_4$ straight or branched alkyl) wherein:
  t is 0 or 1; and
  the $C_3$-$C_5$ cycloalkyl optionally includes an oxygen or nitrogen heteroatom.

wherein:
$R_1$ is hydrogen, cyano, halo, $C_{1-6}$ alkyl, $C_{1-6}$ alkoxy, —C(=O)N($R_{13}$)($R_{14}$), $(CH_2)_qC(=O)N(R_{13})(R_{14})$, $CF_3$, —$OCF_3$, or —S(=O)$_2$$R_{20}$;

q is 0, 1, 2, 3, or 4;

$R_{20}$ is hydrogen or $C_{1-6}$ alkyl, $C_{1-6}$ alkoxy, or —N($R_{13}$)($R_{14}$);

$R_2$ is hydrogen, halo, $C_{1-6}$ alkoxy, or $C_{1-6}$ alkyl;

$R_3$ is hydrogen, hydroxyl, halo, $C_{1-6}$ alkyl, or $C_{1-6}$ alkoxy;

$R_{21}$ and $R_{22}$ are each independently hydrogen, halo, cyano, $C_{1-6}$ alkyl, $C_{1-6}$ alkoxy, $CF_3$, —$OCF_3$, or —S(=O)$_2$$R_{20}$;

$R_{13}$ and $R_{14}$ are each independently hydrogen, $C_{1-6}$ alkyl, cycloalkyl, aryl, heterocyclyl, heteroaryl, hydroxyalkyl, alkylamino, —N($R_{15}$$R_{16}$), or —S(=O)$_2$$R_{20}$;

$R_{15}$ and $R_{16}$ are each independently hydrogen, $C_{1-6}$ alkyl, cycloalkyl, aryl, heterocyclyl, heteroaryl, hydroxyalkyl, or alkylamino;

$R_{17}$ is hydrogen or alkyl;

$R_{24}$ is hydrogen, —N($R_{13}$)($R_{14}$), $C_{1-6}$ alkyl, $C_{1-6}$ alkoxy, alkoxy)(heterocyclyl), or heterocyclyl;

$R_{29}$ is hydrogen, $C_{1-6}$ alkyl, $C_{1-6}$ alkoxy, hydroxyalkyl, heteroaryl, heterocyclyl, —N($R_{15}$$R_{16}$), —C(=O)$R_{46}$, or —$R_{48}$C(=O)$R_{47}$;

$R_{34}$ is hydrogen, $C_{1-6}$ alkyl, $C_{1-6}$ alkoxy, cycloalkyl, hydroxyl, hydroxyalkyl, aryl, heterocyclyl, heteroaryl, alkylamino, $CF_3$, —$OCF_3$, —S(=O)$_2$$R_{20}$, or —N($R_{15}$$R_{16}$); and

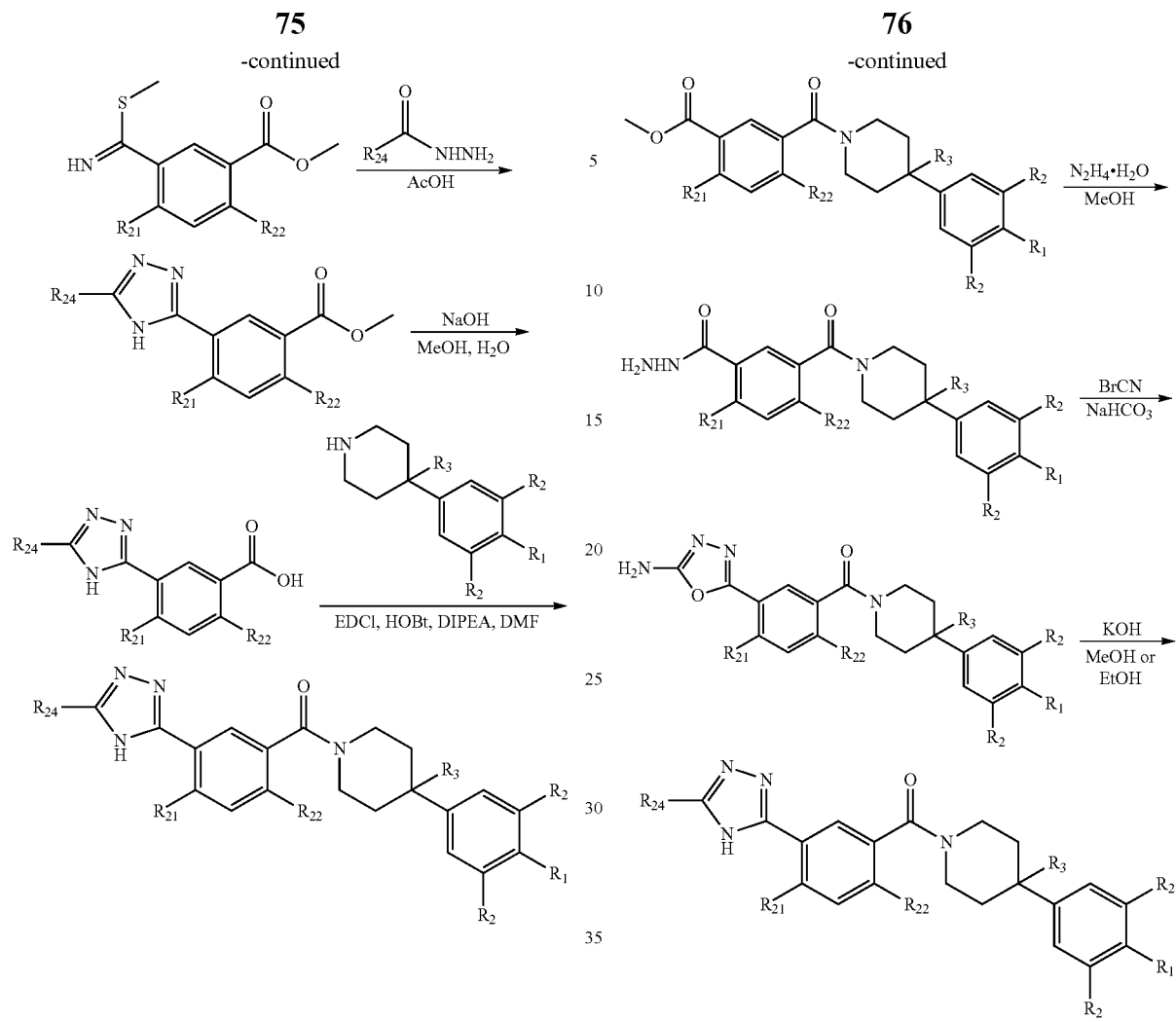
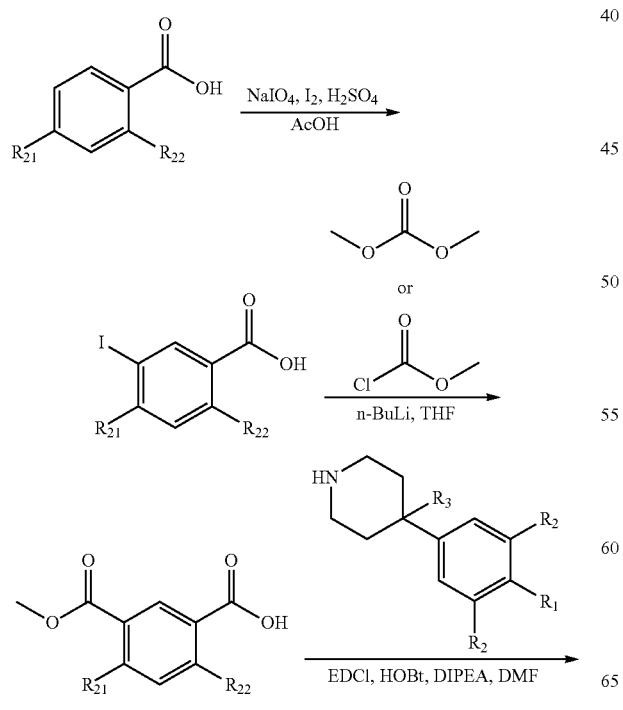
Scheme 7
Scheme 8

77
-continued
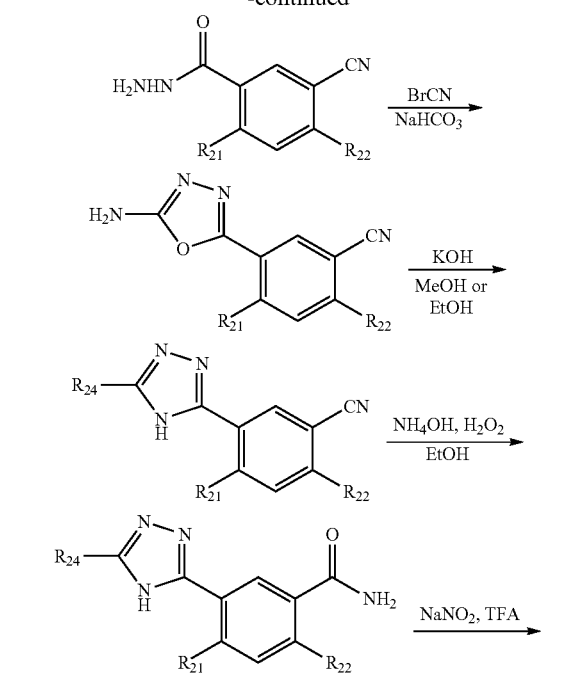
Scheme 9
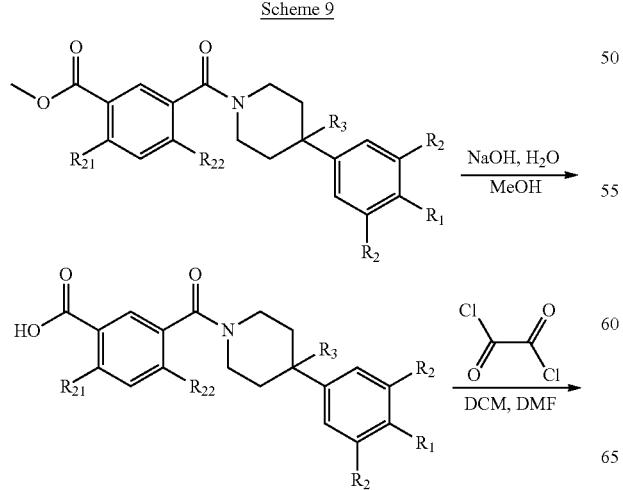
78
-continued
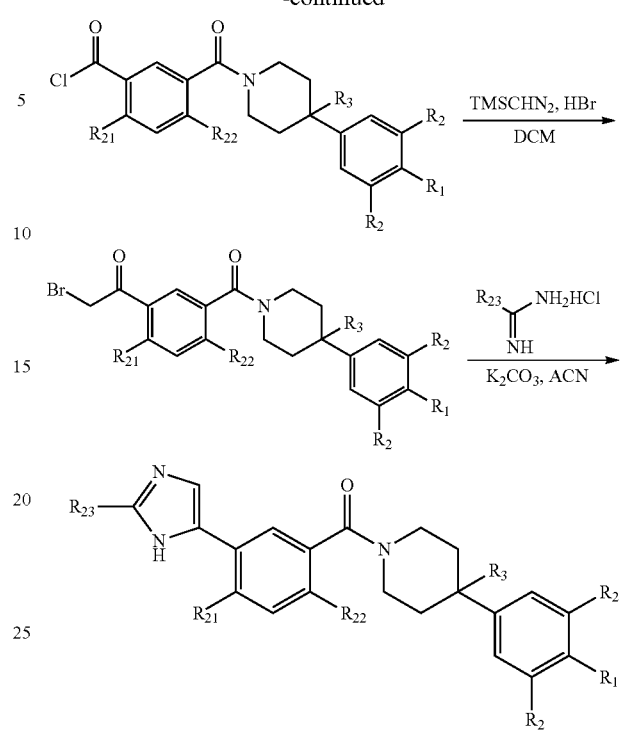
Scheme 10
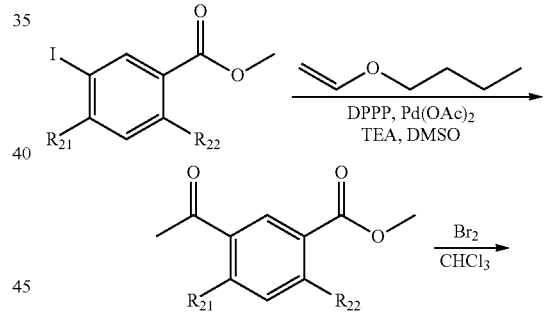
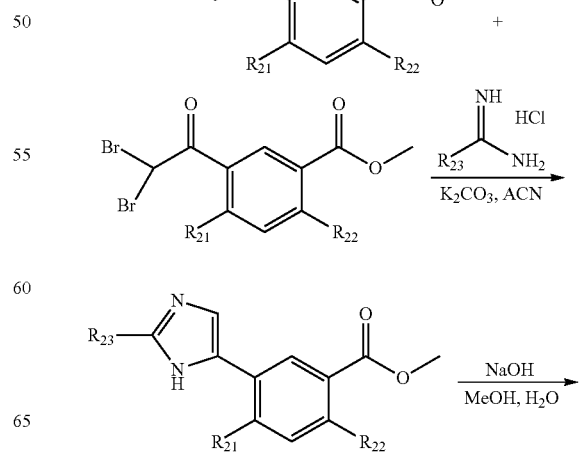

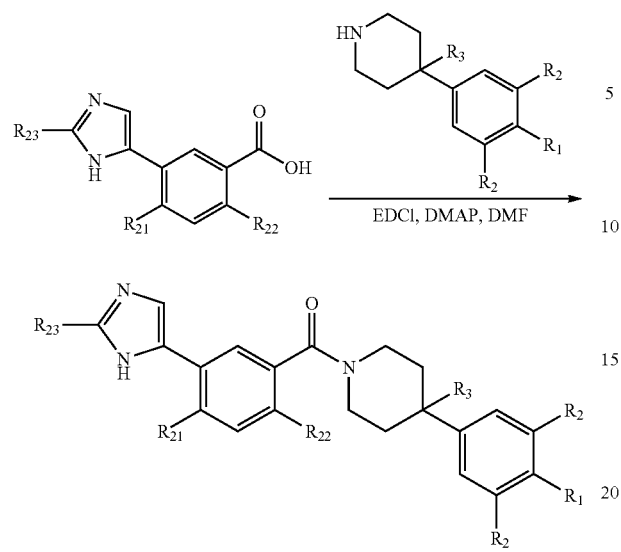
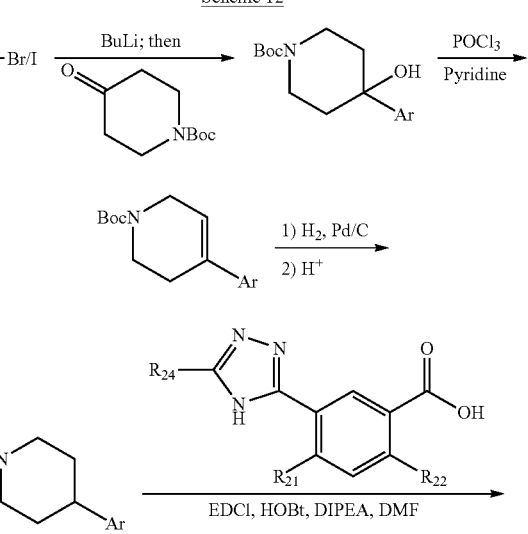
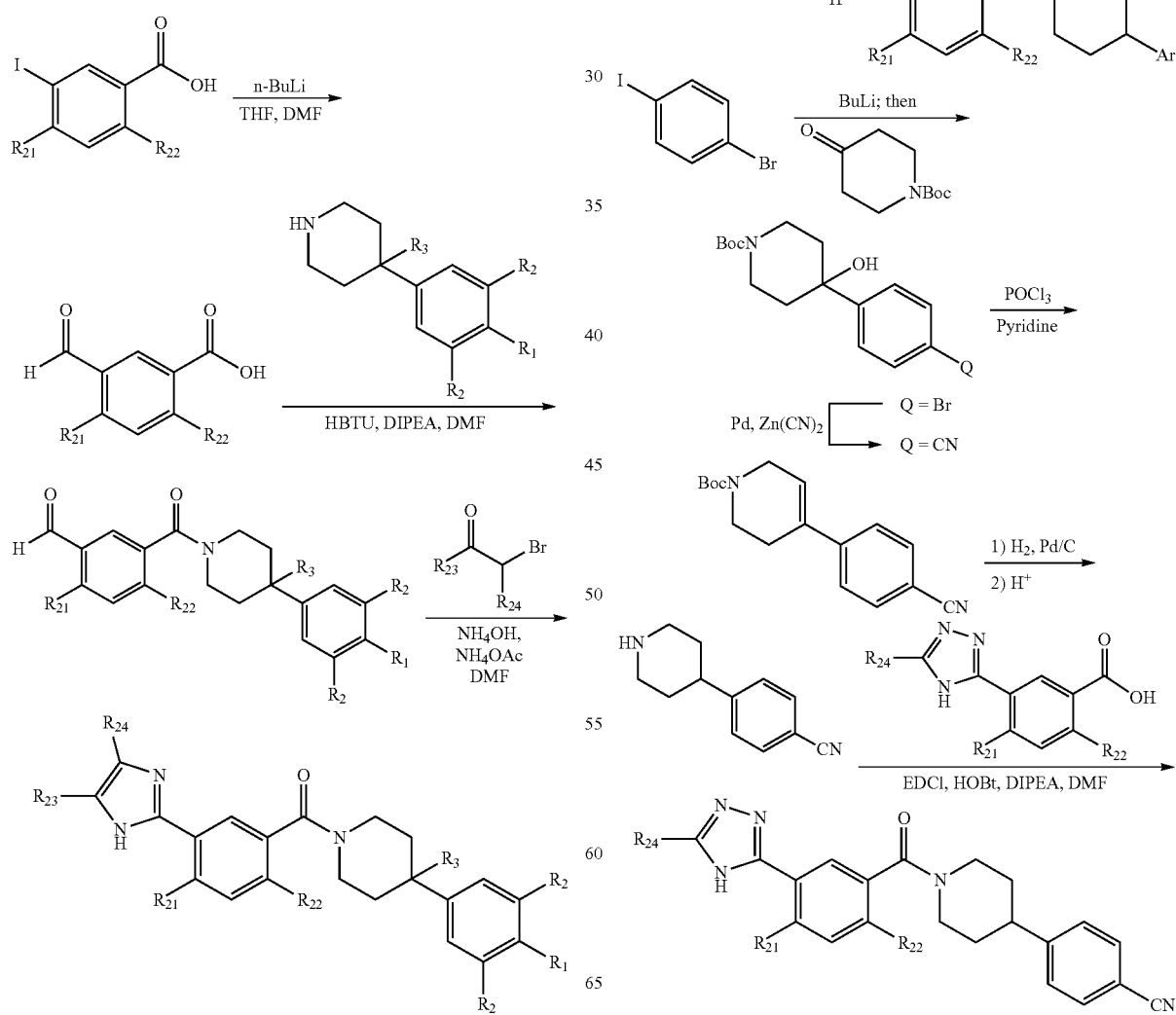

Scheme 13

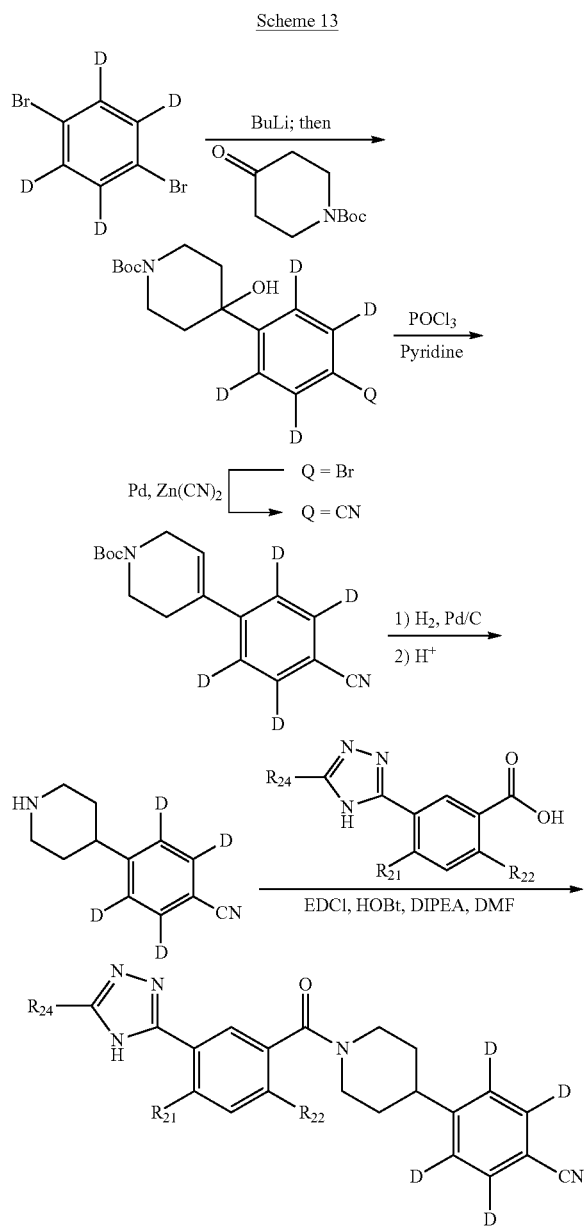

Additional methods for producing particular compounds according to the present disclosure are provided in the EXAMPLES. One skilled in the art will recognize that other compounds of structures can be made by modifications to the specifically disclosed schemes employing methods known to those of skill in the art. Additional examples can be found in Table 1.

Many such techniques are well known in the art. However, many of the known techniques are elaborated in Compendium of Organic Synthetic Methods (Vol. 1, 1971; Vol. 2, 1974; Vol. 3, 1977; Vol. 4, 1980; Vol. 5, 1984; and Vol. 6 as well as March in Advanced Organic Chemistry (1985); Comprehensive Organic Synthesis. Selectivity, Strategy & Efficiency in Modern Organic Chemistry. In 9 Volumes (1993); Advanced Organic Chemistry Part B: Reactions and Synthesis, Second Edition (1983); Advanced Organic Chemistry, Reactions, Mechanisms, and Structure, Second Edition (1977); Protecting Groups in Organic Synthesis, Second Edition; and Comprehensive Organic Transformations (1999).

Viral Infection Pathways

The host cell targets inhibited by the present compounds and methods play a role in the viral replication and/or infection pathways. Targeting of such host cell targets modulates the replication and/or infection pathways of the viruses. In preferred aspects the identified host cell targets are directly or indirectly modulated using the compositions of the present disclosure. The modulation of such host cell targets can also be performed by targeting entities in the upstream or downstream signaling pathways of the host cell targets.

According to the present disclosure, viral infection can be treated by targeting the fatty acid synthesis pathway, and in particular fatty acid synthase. HRV is representative of viruses that can be treated according to the present disclosure. Like other viruses, the replication of HRV involves six phases; transmission, entry, replication, biosynthesis, assembly, and exit. Entry occurs by endocytosis, replication and vRNP assembly takes place in the nucleus, and the virus buds from the plasma membrane. In the infected patient, the virus targets airway epithelial cells. The present compounds and methods target and modulate at least one host cell targets involved in such pathways.

For some viruses a great deal of progress has been made in the elucidation of the steps involved during infection of host cells. For example, experiments initiated in the early 1980s showed that influenza virus follows a stepwise, endocytic entry program with elements shared with other viruses such as alpha- and rhabdoviruses (Marsh and Helenius 1989; Whittaker 2006). The steps include: 1) Initial attachment to sialic acid containing glycoconjugates receptors on the cell surface; 2) signaling induced by the virus particle; 3) endocytosis by clathrin-dependent and clathrin-independent cellular mechanism; 4) acid-induced, hemaglutinin (HA)-mediated penetration from late endosomes; 5) acid-activated, M2 and matrix protein (M1) dependent uncoating of the capsid; and, 6) intra-cytosolic transport and nuclear import of vRNPs. These steps depend on assistance from the host cell in the form of sorting receptors, vesicle formation machinery, kinase-mediated regulation, organelle acidification, and, most likely, activities of the cytoskeleton.

Influenza attachment to the cells surface occurs via binding of the HA1 subunit to cell surface glycoproteins and glycolipids that carry oligosaccharide moieties with terminal sialic acid residues (Skehel and Wiley 2000). The linkage by which the sialic acid is connected to the next saccharide contributes to species specificity. Avian strains including H5N1 prefer an a-(2,3)-link and human strains a-(2,6)-link (Matrosovich 2006). In epithelial cells, binding occurs preferentially to microvilli on the apical surface, and endocytosis occurs at base of these extensions (Matlin 1982). Whether receptor binding induces signals that prepare the cell for the invasion is not yet known, but it is likely because activation of protein kinase C and synthesis of phopshatidylinositol-3-phosphate (PI3P) are required for efficient entry (Sieczkarski et al. 2003; Whittaker 2006).

Endocytic internalization occurs within a few minutes after binding (Matlin 1982; Yoshimura and Ohnishi 1984). In tissue culture cells influenza virus makes use of three different types of cellular processes; 1) preexisting clathrin coated pits, 2) virus-induced clathrin coated pits, and 3) endocytosis in vesicles without visible coat (Matlin 1982; Sieczkarski and Whittaker 2002; Rust et al. 2004). Video microscopy using fluorescent viruses showed the virus particles undergoing actin-mediated rapid motion in the cell periphery followed by minus end-directed, microtubule-mediated transport to the perinuclear area of the cell. Live cell imaging indicated that the virus particles first entered a subpopulation of mobile, peripheral early endosomes that carry them deeper into the cytoplasm before penetration takes place (Lakadamyali et al. 2003; Rust et al. 2004). The endocytic process is regulated by protein and lipid kinases, the proteasome, as well as by Rabs and ubiquitin-dependent sorting factors (Khor et al. 2003; Whittaker 2006).

The membrane penetration step is mediated by low pH-mediated activation of the trimeric, metastable HA, and the conversion of this Type I viral fusion protein to a membrane fusion competent conformation (Maeda et al. 1981; White et al. 1982). This occurs about 16 min after internalization, and the pH threshold varies between strains in the 5.0-5.6 range. The target membrane is the limiting membrane of intermediate or late endosomes. The mechanism of fusion has been extensively studied (Kielian and Rey 2006). Further it was observed that fusion itself does not seem to require any host cell components except a lipid bilayer membrane and a functional acidification system (Maeda et al. 1981; White et al. 1982). The penetration step is inhibited by agents such as lysosomotropic weak bases, carboxylic ionophores, and proton pump inhibitors (Matlin 1982; Whittaker 2006).

To allow nuclear import of the incoming vRNPs, the capsid has to be disassembled. This step involves acidification of the viral interior through the amantadine-sensitive M2-channels causes dissociation of Mifrom the vRNPs (Bukrinskaya et al. 1982; Martin and Helenius 1991; Pinto et al. 1992). Transport of the individual vRNPs to the nuclear pore complexes and transfer into the nucleus depends on cellular nuclear transport receptors (O'Neill et al. 1995; Cros et al. 2005). Replication of the viral RNAs (synthesis of positive and negative strands), and transcription occurs in complexes tightly associated with the chromatin in the nucleus. It is evident that, although many of the steps are catalyzed by the viral polymerase, cellular factors are involved including RNA polymerase activating factors, a chaperone HSP90, hCLE, and a human splicing factor UAP56. Viral gene expression is subject to complex cellular control at the transcriptional level, a control system dependent on cellular kinases (Whittaker 2006).

The final assembly of an influenza particle occurs during a budding process at the plasma membrane. In epithelial cells, budding occurs at the apical membrane domain only (Rodriguez-Boulan 1983). First, the progeny vRNPs are transported within the nucleoplasm to the nuclear envelope, then from the nucleus to the cytoplasm, and finally they accumulate in the cell periphery. Exit from the nucleus is dependent on viral protein NEP and M1, and a variety of cellular proteins including CRM1 (a nuclear export receptor), caspases, and possibly some nuclear protein chaperones. Phosphorylation plays a role in nuclear export by regulating M1 and NEP synthesis, and also through the MAPK/ERK system (Bui et al. 1996; Ludwig 2006). G protein and protein kinase signaling is involved in influenza virus budding from infected host cells (Hui E. and Nayak D, 2002).

The three membrane proteins of the virus are synthesized, folded and assembled into oligomers in the ER (Doms et al. 1993). They pass through the Golgi complex; undergo maturation through modification of their carbohydrate moieties and proteolytic cleavage. After reaching the plasma membrane they associate with M1 and the vRNPs in a budding process that results in the inclusion of all eight vRNPs and exclusion of most host cell components except lipids.

Influenza infection is associated with activation of several signaling cascades including the MAPK pathway (ERK, JNK, p38 and BMK-1/ERK5), the IkB/NF-kB signaling module, the Raf/MEK/ERK cascade, and programmed cell death (Ludwig 2006). These result in a variety of effects that limit the progress of infection such as transcriptional activation of IFNb, apoptotic cell death, and a block in virus escape of from late endosomes (Ludwig 2006).

Most previous studies on virus-cell interactions were performed in tissue culture using tissue culture- or egg-adapted virus strains. The viruses in these examples were adapted in such as manner that changes were induced that affected receptor binding and tropism (Matrosovich 2006). Infection with wild-type pathogenic strains is provides a more natural picture of viral interaction with host proteins. It is known that in the human airways influenza A and B primarily infect non ciliated epithelial cells in the upper respiratory track carrying NeuSAc a-(2,6)-Gal, whereas avian strains infect ciliated epithelial cell with a-(2,3)-linked sialic acids deeper in the airways (Matrosovich et al. 2004a).

Additionally, progress has been made in the elucidation of the steps involved during infection by HRV of host cells. Selected events in rhinovirus infection of the normal human airway can be regarded as occurring sequentially. Initial steps in rhinovirus pathogenesis are believed to include viral entry through the nose, mucociliary transport of virus to the posterior pharynx, and initiation of infection in ciliated and non-ciliated epithelial cells of the upper airway. Viral replication peaks on average within 48 h of initiation of infection and persists for up to 3 wk. Infection is followed by activation of several inflammatory mechanisms, which can include release or generation of interleukins, bradykinins, prostaglandins, and possibly histamine and stimulation of parasympathetic reflexes. Pathophysiologic processes are initiated, which include vasodilatation of nasal blood vessels, transudation of plasma, glandular secretion, and stimulation of nerve fibers, causing pain and triggering sneeze and cough reflexes. The resultant clinical illness is a rhinosinusitis, pharyngitis, and bronchitis, which, on average, lasts one week.

Changes in gene expression profiles during in vivo rhinovirus infections have been identified (Proud D. et al. Am J Respir Crit Care Med Vol 178. pp 962-968, 2008). Nasal epithelial scrapings were obtained before and during experimental rhinovirus infection, and gene expression was evaluated by microarray. Viperin is identified as an antiviral protein induced by interferon (IFN), viral infections, and pathogen-associated molecules. Naturally acquired rhinovirus infections, cultured human epithelial cells, and short interfering RNA knockdown were used to further evaluate the role of viperin in rhinovirus infections. Symptom scores and viral titers were measured in subjects inoculated with rhinovirus or a sham control, and changes in gene expression were assessed 8 and 48 hours after inoculation. Rhinovirus-induced changes in gene expression were not observed 8 hours after viral infection, but 11,887 gene transcripts were significantly altered in scrapings obtained 2 days post-inoculation. Major groups of up-regulated genes include chemokines, signaling molecules, interferon-responsive genes, and antivirals. Rhinovirus infection significantly alters the expression of many genes associated with the immune response, including chemokines and antivirals. Some of the genes markedly induced by HRV-16 infection include but are not limited to CCL2, CCL8, CXCL11, CXCL10, CXCL13, CXCL9, CCL20, IFIT2, GBP1, IFIT1, GIP2, IFIT4, IL28B, IRF7, CIG5, NOS2A, OAS3, OASL, OAS2, OAS1, MX2, MX1, PLSCR1, SOCS1, SOCS2, MDA5, RIGI, SOCS3, ICAM-1, HAPLN3, MMP12, EPSTI1, and TNC.

Fatty Acid Synthesis Pathway

Various aspects of the present disclosure relate to compositions and methods that modulate the activity of the fatty acid synthesis pathway to treat a viral infection or treat cancer. The fatty acid synthesis pathway in humans can use four enzymes: 1) acetyl-CoA carboxylase (ACC), which can synthesize malonyl-CoA; 2) malic enzyme, which can produce NADPH; 3) citrate lyase, which can synthesize acetyl-CoA; and 4) fatty acid synthase, which can catalyze NADPH-dependent synthesis of fatty acids from acetyl-CoA and malonyl-CoA. In various aspects, the present disclosure relates to treatment of viral infections and cancer by modulating the activity of the fatty acid synthase protein.

The final products of fatty acid synthase are free fatty acids which can use separate enzymatic derivatization with coenzyme-A for incorporation into other products. In humans, fatty acid synthesis can occur in two sites: the liver, where palmitic acid can be made (Roncari, (1974) *Can. J. Biochem.*, 52:221-230) and lactating mammary gland, where $C_{10}$-$C_{14}$ fatty acids can be made (Thompson, et al., (1985) *Pediatr. Res.*, 19:139-143).

Fatty acids can be synthesized in the cytoplasm from acetyl-CoA. Acetyl-CoA can be generated from pyruvate by pyruvate dehyrodenase (PDH) and by β-oxidation of fatty acids in the mitochondria. A "citrate shuttle" can transport acetyl-CoA from the mitochondria to the cytoplasm. Acetyl-CoA can react with oxaloacetate to yield citrate, and a tricarboxylate translocase can transport citrate from the mitochondria to the cytosol. In the cytoplasm, citrate can be cleaved back to oxaloacetate and acetyl-CoA, a reaction that can be catalyzed by ATP-citrate lyase. Oxaloacetate can be converted back to pyruvate for re-entry into mitochondria.

Acetyl-CoA can be converted to malonyl-CoA. Acetyl-CoA carboxylase (ACC) is a complex multifunctional, biotin-containing, enzyme system that can catalyze carboxylation of acetyl-CoA to malonyl-CoA. This conversion is an irreversible, rate-limiting step in fatty acid synthesis. ACC can carry out three functions: biotin carboxyl carrier protein, biotin carboxylase and carboxyltransferase. ATP-dependent carboxylation of biotin, a prosthetic group (cofactor) can be followed by transfer of the carboxyl group to acetyl-CoA.

$HCO_3^- + ATP + acetyl-CoA \rightarrow ADP + P_i + malonyl-CoA$

There are two ACC forms, alpha and beta, encoded by two different genes ACC-alpha (also known as ACC, ACAC, ACC1, ACCA, and ACACA) can encode protein highly enriched in lipogenic tissues. Multiple alternatively spliced transcript variants divergent in the sequence and encoding distinct isoforms have been found for this gene. ACC-beta (also known as ACC2, ACCB, HACC275, and ACACB) can encode protein thought to control fatty acid oxidation by means of the ability of malonyl-CoA to inhibit carnitine-palmitoyl-CoA transferase I, the rate-limiting step in fatty acid uptake and oxidation by mitochondria. ACC-beta may be involved in the regulation of fatty acid oxidation, rather than fatty acid biosynthesis. There is evidence for the presence of two ACC-beta isoforms.

ACC can be regulated by the phosphorylation/dephosphorylation of targeted serine residues. For example, AMP-activated kinase (AMPK) can phosphorylate ACC, and this phosphorylation can inhibit the ability of ACC to produce malonyl-CoA. On ACACA, AMPK can phosphorylate Ser79, Ser1200, and Ser1215 (Park S. H. et al. (2002) *J. Appl. Physiol.* 92:2475-82). AMPK can phosphorylate Ser218 on ACACB (Hardie D. G. (1992) *Biochim. Biophys. Acta* 1123:231-8). Also, cAMP-dependent protein kinase (Protein Kinase A, or PKA) can phosphorylate ACC.

ACC can be regulated by allosteric transformation by citrate or palmitoyl-CoA. For example, citrate can be a positive effector (i.e. citrate can allosterically activate ACC). Citrate concentration can be high when there is adequate acetyl-CoA entering the Krebs Cycle. Excess aceytl-CoA can then be converted via malonyl-CoA to fatty acids. Palmitoyl-CoA can be a negative effector. Palmitoyl-CoA, which is the product of Fatty Acid Synthase (FASN), can promote the inactive conformation of ACC, which can reduce production of malonyl-CoA (a feedback inhibition process). AMP can regulate fatty acid synthesis by regulating the availability of malonyl-CoA. Insulin binding a receptor can activate a phosphatase to dephosphorylate ACC, which can remove the inhibitory effect.

The fatty acid synthase gene (also known as FAS, OA-519, SDR27X1; MGC14367; MGC15706; FASN) is involved in fatty acid synthesis. The enzyme encoded by this gene is a multifunctional protein of approximately 272 kDa with multiple domains, each with distinct enzyme activities that can play a role in fatty acid biosynthesis. FASN can catalyze the synthesis of palmitate from acetyl-CoA and malonyl-CoA, in the presence of NADPH, into long-chain saturated fatty acids. In some cancer cell lines, FASN protein has been found to be fused with estrogen receptor-alpha (ER-alpha), in which the N-terminus of FASN is fused in-frame with the C-terminus of ER-alpha.

FASN protein can exist in the cytosol as a dimer of identical subunits. FASN consists of three catalytic domains in the N-terminal section (-ketoacyl synthase (KS), malonyl/acetyltransferase (MAT), and dehydrase (DH)). The N-terminal section is separated by a core region of about 600 amino acids from four C-terminal domains (enoyl reductase (ER), -ketoacyl reductase (KR), acyl carrier protein (ACP), and thioesterase (TE)). The crystal structure of a mammalian fatty acid synthase has been reported (Maier T. et al. (2008) *Science* 321: 1315-1322). Each of the catalytic domains of FASN can be targeted in the methods of treating viral infection of the provided invention.

The enzymatic steps of fatty acid synthesis can involve decarboxylative condensation, reduction, dehydration, and another reduction and can result in a saturated acyl moiety. NADPH can be an electron donor in reductive reactions.

Antiviral Activity

In various aspects, the present disclosure provides methods for treating viral infection in a subject, the method comprising administering to a subject in need of such treatment an effective amount of a compound of Structures (I), (II), (III), (IV), (V), (VI), (VII), (VIII), (IX), (X), (XI) or as provided in Table 1.

In various aspects, the disclosure provides methods for treating a viral infection, the method comprising administering the compounds of the present disclosure to a subject in need thereof the agent.

The present disclosure contemplates the treatment of any viral infection that targets the fatty acid synthesis pathway in a host, and in particular by modulating the activity of fatty acid synthase. For example, the present methods can be used to treat influenza infection, adenovirus infection, respiratory syncytial virus infection, poxvirus infection, poliomyelitis infection, hepatitis C infection, yellow fever infection, dengue fever infection, rhinovirus infection, and the like.

In various aspects, the present disclosure provides methods for treating hepatitis C infection by administering to the subject one or more compounds disclosed herein. In modulating the FASN pathway in the subject, hepatitis C infection is treated. It has been shown that expression of FASN is upregulated in human hepatoma cell line Huh7 when these cells are infected with HCV. Inhibiting FASN production with a FASN inhibitor reduced the production of HCV. Thus administration to a subject of the compounds of the present disclosure. (Yang, W. et al. (2008) *Hepatology* 48(5):1396-1403). It is demonstrated in the EXAMPLES that FASN inhibition correlates to inhibition of HCV.

In certain aspects, the methods of inhibiting viral infection can be performed in vitro. In further aspects, the methods of inhibiting viral infection can be performed in vivo.

In certain aspects the compounds of the present disclosure may be used in combination with other antiviral treatments in the treating of viral infection.

In various aspects, the viral infection is a human yellow fever infection. In further aspects, the viral infection is a human hepatitis C infection. In yet further aspects, the viral infection is a human rhinoviral infection.

In various aspects the compounds of the present disclosure can be used for the treatment of infection of an animal subject, such as a human, by any of a plethora of viruses.

In certain aspects, the compounds of the present disclosure can be used for the inhibition of a host by a respiratory virus. Respiratory viruses are most commonly transmitted by airborne droplets or nasal secretions and can lead to a wide spectrum of illness. Respiratory viruses include the respiratory syncytial virus (RSV), influenza viruses, coronaviruses such as SARS, adenoviruses, parainfluenza viruses and rhinoviruses (HRV).

According to one aspect, the present disclosure can be used to treat infection by HRV. The genus of rhinoviruses is a member of the Picornaviridae family of viruses. Genera within the family include the Genus *Enterovirus, Rhinovirus, Cardiovirus, Aphthovirus, Hepatovirus, Parechovirus, Erbovirus, Kobuvirus, Teschovirus*. Human rhinoviruses (HRV) include the most common viruses that infect humans and can cause the common cold. HRV are lytic in nature. Rhinoviruses have single-stranded positive sense RNA genomes of between 7.2 and 8.5 kb in length. At the 5' end of these genomes is a virus-encoded protein, and like mammalian mRNA, there is also a 3' poly-A tail. The 5'-terminal UMP of the viral RNA is covalently linked to the small viral protein VPg (Paul A V, et al. *Nature* 1998, 393(6682):280-284). The 5'UTR contains two structural elements. One is the 5'-cloverleaf structure involved in the plus-strand RNA synthesis and in the process of switching from translation to replication (Huang H, et al. *Biochemistry* 2001, 40(27):8055-8064). The other is the internal ribosomal entry site (IRES) which promotes translation of the polyprotein. In addition, species-specific internal cis-acting replication elements (cre) have been identified in human enteroviruses (HEV), HRV-A and HRV-B (Gerber K, Wimmer E, Paul A V, *J Virol* 2001, 75(22):10979-10990). The viral particles themselves are not enveloped and are icosahedral in structure Rhinoviruses also grow best in temperatures between 33-35° C. They are also sensitive to acidic environment.

HRV viral proteins are transcribed as a single long polypeptide, which is cleaved into the viral structural and non-structural proteins Rhinoviruses are composed of a capsid that contains four viral proteins VP1, VP2, VP3 and VP4 (Rossmann M, et al. 1985 *Nature* 317 (6033): 145-53; Smith T, et al. 1986, *Science* 233 (4770): 1286-93). The isometric nucleocapsids are 22-40 nm in diameter. VP1, VP2, and VP3 form the major part of the protein capsid. The much smaller VP4 protein has a more extended structure and lies at interface between the capsid and the RNA genome. There are 60 copies of each of these proteins assembled as an icosahedron. Human antibodies that target epitopes lying on the exterior regions of VP1-VP3 play a role in the immune response to HRVs.

HRVs have two general modes of transmission: 1) via aerosols of respiratory droplets and 2) from contaminated surfaces, including direct person-to-person contact. The primary route of entry for rhinoviruses is the upper respiratory tract. Afterwards, an HRV binds to ICAM-1 (Inter-Cellular Adhesion Molecule 1) also known as CD54 (Cluster of Differentiation 54) receptors on respiratory epithelial cells. As the virus replicates and spreads, infected cells release chemokines and cytokines, which in turn activate inflammatory mediators. Infection occurs rapidly, with the rhinovirus adhering to surface receptors within 15 minutes of entering the respiratory tract. The incubation period is generally 8-10 hours before symptoms begin to occur. HRVs are the most frequent cause of infection across all age groups of the human population. Replication is often restricted to the upper respiratory tract leading to self-limited illnesses such as the common cold. However, HRV infections can also exacerbate pre-existing airway disorders, invade the lower respiratory tract and lead to serious complications.

In another aspect, the compounds of the present disclosure can be used for the treatment of infection by the influenza virus by targeting the pathways that the virus relies on for infection or replication. Influenza viruses belong to Orthomyxoviridae family of viruses. This family also includes Thogoto viruses and Dhoriviruses. There are several types and subtypes of influenza viruses known, which infect humans and other species. Influenza type A viruses infect people, birds, pigs, horses, seals and other animals, but wild birds are the natural hosts for these viruses. Influenza type A viruses are divided into subtypes and named on the basis of two proteins on the surface of the virus: hemagglutinin (HA) and neuraminidase (NA). For example, an "H7N2 virus" designates an influenza A subtype that has an HA 7 protein and an NA 2 protein. Similarly an "H5N1" virus has an HA 5 protein and an NA 1 protein. There are 16 known HA subtypes and 9 known NA subtypes. Many different combinations of HA and NA proteins are possible. Only some influenza A subtypes (i.e., H1N1, H1N2, and H3N2) are currently in general circulation among people. Other subtypes are found most commonly in other animal species. For example, H7N7 and H3N8 viruses cause illness in horses, and H3N8 also has recently been shown to cause illness in dogs (see www.cdc.gov/flu/avian/gen-info/flu-viruses.htm).

Antiviral agents which target host cell proteins involved in influenza infection can be used to protect high-risk groups (hospital units, institutes caring for elderly, immuno-suppressed individuals), and on a case by case basis. A potential use for antiviral agents is to limit the spread and severity of the future pandemics whether caused by avian H5N1 or other strains of influenza virus. Avian influenza A viruses of the subtypes H5 and H7, including H5N1, H7N7, and H7N3 viruses, have been associated with high pathogenicity, and human infection with these viruses have ranged from mild (H7N3, H7N7) to severe and fatal disease (H7N7, H5N1). Human illness due to infection with low pathogenicity viruses has been documented, including very mild symptoms (e.g., conjunctivitis) to influenza-like illness. Examples of low pathogenicity viruses that have infected humans include H7N7, H9N2, and H7N2 (see www.cdc.gov/flu/avian/gen-info/flu-viruses.htm).

Influenza B viruses are usually found in humans but can also infect seals. Unlike influenza A viruses, these viruses are not classified according to subtype. Influenza B viruses can cause morbidity and mortality among humans, but in general are associated with less severe epidemics than influenza A viruses. Although influenza type B viruses can cause human epidemics, they have not caused pandemics. (see www.cdc.gov/flu/avian/gen-info/flu-viruses.htm).

Influenza type C viruses cause mild illness in humans and do not cause epidemics or pandemics. These viruses can also infect dogs and pigs. These viruses are not classified according to subtype. (see www.cdc.gov/flu/avian/gen-info/flu-viruses.htm).

Influenza viruses differ from each other in respect to cell surface receptor specificity and cell tropism, however they use common entry pathways. The compounds of the present disclosure advantageously target pathways that are common to multiple viruses giving rise to broader antiviral activity. Thus, the present compounds can also prove useful against unrelated viruses that use similar pathways. For example, the agents can protect airway epithelial cells against a number of different viruses in addition to influenza viruses.

In certain aspects, the compounds of the present disclosure can be used for the treatment of infection by adenoviruses. Most adenoviruses commonly cause respiratory illness; symptoms of respiratory illness caused by adenovirus infection range from the common cold syndrome to pneumonia, croup, and bronchitis. Patients with compromised immune systems are especially susceptible to severe complications of adenovirus infection. Acute respiratory disease (ARD), first recognized among military recruits during World War II, can be caused by adenovirus infections during conditions of crowding and stress. Adenoviruses are medium-sized (90-100 nm), nonenveloped icosohedral viruses containing double-stranded DNA. There are 49 immunologically distinct types (6 subgenera: A through F) that can cause human infections. Adenoviruses are unusually stable to chemical or physical agents and adverse pH conditions, allowing for prolonged survival outside of the body. Some adenoviruses, such as AD2 and Ad5 (species C) use clathrin mediated endocytosis and macropinocytosis for infectious entry. Other adenoviruses, such as Ad3 (species B) use dynamin dependent endocytosis and macropinocytosis for infectious entry.

In certain aspects, the compounds of the present disclosure can be used for the treatment of infection by respiratory syncytial virus (RSV). RSV is the most common cause of bronchiolitis and pneumonia among infants and children under 1 year of age. Illness begins most frequently with fever, runny nose, cough, and sometimes wheezing. During their first RSV infection, between 25% and 40% of infants and young children have signs or symptoms of bronchiolitis or pneumonia, and 0.5% to 2% require hospitalization. Most children recover from illness in 8 to 15 days. The majority of children hospitalized for RSV infection are under 6 months of age. RSV also causes repeated infections throughout life, usually associated with moderate-to-severe cold-like symptoms; however, severe lower respiratory tract disease can occur at any age, especially among the elderly or among those with compromised cardiac, pulmonary, or immune systems. RSV is a negative-sense, enveloped RNA virus. The virion is variable in shape and size (average diameter of between 120 and 300 nm), is unstable in the environment (surviving only a few hours on environmental surfaces), and is readily inactivated with soap and water and disinfectants.

In certain aspects, the compounds of the present disclosure can be used for the treatment of infection by human parainfluenza virus (HPIV). HPIVs are second to respiratory syncytial virus (RSV) as a common cause of lower respiratory tract disease in young children. Similar to RSV, HPIVs can cause repeated infections throughout life, usually manifested by an upper respiratory tract illness (e.g., a cold and/or sore throat). HPIVs can also cause serious lower respiratory tract disease with repeat infection (e.g., pneumonia, bronchitis, and bronchiolitis), especially among the elderly, and among patients with compromised immune systems. Each of the four HPIVs has different clinical and epidemiologic features. The most distinctive clinical feature of HPIV-1 and HPIV-2 is croup (i.e., laryngotracheobronchitis); HPIV-1 is the leading cause of croup in children, whereas HPIV-2 is less frequently detected. Both HPIV-1 and -2 can cause other upper and lower respiratory tract illnesses. HPIV-3 is more often associated with bronchiolitis and pneumonia. HPIV-4 is infrequently detected, possibly because it is less likely to cause severe disease. The incubation period for HPIVs is generally from 1 to 7 days. HPIVs are negative-sense, single-stranded RNA viruses that possess fusion and hemagglutinin-neuraminidase glycoprotein "spikes" on their surface. There are four serotypes types of HPIV (1 through 4) and two subtypes (4a and 4b). The virion varies in size (average diameter between 150 and 300 nm) and shape, is unstable in the environment (surviving a few hours on environmental surfaces), and is readily inactivated with soap and water.

In various aspects, the compounds of the present disclosure can be used for the treatment of infection by coronavirus. Coronavirus is a genus of animal virus belonging to the family Coronaviridae. Coronaviruses are enveloped viruses with a positive-sense single-stranded RNA genome and a helical symmetry. The genomic size of coronaviruses ranges from approximately 16 to 31 kilobases, extraordinarily large for an RNA virus. The name "coronavirus" is derived from the Latin corona, meaning crown, as the virus envelope appears under electron microscopy to be crowned by a characteristic ring of small bulbous structures. This morphology is actually formed by the viral spike peplomers, which are proteins that populate the surface of the virus and determine host tropism. Coronaviruses are grouped in the order Nidovirales, named for the Latin nidus, meaning nest, as all viruses in this order produce a 3' co-terminal nested set of subgenomic mRNA's during infection. Proteins that contribute to the overall structure of all coronaviruses are the spike, envelope, membrane and nucleocapsid. In the specific case of SARS a defined receptor-binding domain on S mediates the attachment of the virus to its cellular receptor, angiotensin-converting enzyme 2.

In a further embodiment, the disease state associated with dysregulation of the mTOR pathway is a viral infection. In one embodiment, the viral infection is by a virus from the herpesviridae family of viruses. In one embodiment the viral infection is by a herpesviridae virus selected from the group consisting of herpes simplex virus (HSV) types 1 and 2, varicella-zoster virus, cytomegalovirus (CMV), Epstein-Barr virus (EBV), human herpesvirus 6 (variants A and B), human herpesvirus 7, human herpesvirus 8 (Kaposi's sarcoma-associated herpesvirus, KSHV), and cercopithecine herpesvirus 1 (B virus). In one embodiment the viral infection is by a virus selected from human cytomegalovirus and herpes simplex virus-I.

In one embodiment, the viral infection is by a virus from the paramyxoviridae family of viruses. In one embodiment, the viral infection is by a paramyxoviridae virus selected from the group consisting of Respiratory syncytial virus (RSV), mumps, measles, human parainfluenza viruses such as Parainfluenza Virus Type 3 (PIV3), Human metapneumovirus, Hendra virus (HeV), Nipah virus (NiV), and Cedar Virus.

In one embodiment, the viral infection is by a virus from the picomaviridae family of viruses. In one embodiment, the viral infection is by a picomaviridae virus selected from the group consisting of Human rhinovirus 16 (HRV-16), Human enterovirus, Hepatitis A virus, Coxsackie virus (including type A24 varient CA24v), Echovirus, and Poliovirus.

In one embodiment, the viral infection is by a virus from the orthomyxoviridae family of viruses. In one embodiment, the viral infection is by a orthomyxoviridae virus selected from the group consisting of Avian influenza (pathogenic strain (H5N1)), and Swine influenza including influenza C and the subtypes of influenza A known as H1N1, H1N2, H2N1, H3N1, H3N2, and H2N3.

In one embodiment, the viral infection is by a virus from the retroviridae family of viruses. In one embodiment, the viral infection is by a retroviridae virus selected from the group consisting of human immunodeficiency virus (HIV-1).

In one embodiment, the viral infection is by a virus from the papillomaviridae family of viruses. In one embodiment, the viral infection is by a papillomaviridae virus selected from the group consisting of human papillomavirus (HPV).

In one embodiment, the viral infection is by a virus from the adenoviridae family of viruses. In one embodiment, the viral infection is by a adenoviridae virus selected from the group consisting of human adenovirus (Adenovirus serotype 14.)

In one embodiment, the viral infection is by a virus from the poxviridae family of viruses. In one embodiment, the viral infection is by a poxviridae virus selected from the group consisting of Human orthopoxviruses, Monkeypox virus, Variola (VARV), including smallpox (Variola major virus) and Alastrim (Variola minor virus)), Cowpox (CPX), and Vaccinia (VACV or VV) viruses.

In one embodiment, the viral infection is by a virus from the polyomaviridae family of viruses.

In one embodiment, the viral infection is by a virus causing viral hemorrhagic fever. In one embodiment, the virus causing viral hemorrhagic fever is selected from the group consisting of arenaviruses, filoviruses, bunyaviruses, and flaviviruses including Bundibugyo virus (BDBV), Sudan virus (SUDV), Tai Forest virus (TAFV) and Ebola virus (EBOV, formerly Zaire Ebola virus), Marburg, Lassa, Crimean-Congo, Seoul viruses, Lassa fever virus, Lujo virus and Argentine hemorrhagic fever. In one embodiment, the virus causing viral hemorrhagic fever is a South American Haemorrhagic Fever virus selected from the group consisting of Chapare, Guanarito, Junin, Machupo, Sabia, Hantavirus hemorrhagic fever with renal syndrome (HFRS) and hantavirus pulmonary syndrome (HPS).

In one embodiment, the viral infection is by a virus from the flaviviridae family of viruses. In one embodiment, the viral infection is by a flaviviridae virus selected from the group consisting of Yellow fever, tick-borne encephalitis virus (TBEV), Kyasanur Forest disease virus, Omsk hemorrhagic fever virus, hepatitis B virus (HBV), hepatitis C virus (HCV), Dengue viruses (DEN-1, DEN-2, DEN-3 and DEN-4), West Nile virus.

In one embodiment, the viral infection is by a virus from the togaviridae family of viruses. In one embodiment, the viral infection is by a togaviridae virus selected from the group consisting of Eastern Equine Encephalitis virus, Venezuelan equine encephalitis virus, Western equine encephalitis virus, zoonotic alphaviruses (Chikungunya virus, Semliki Forest virus complex), and arbovirus.

In one embodiment, the viral infection is by a virus from the coronaviridae family of viruses. In one embodiment, the viral infection is by a coronaviridae virus selected from the group consisting of a SARS-associated coronavirus (SARS-CoV) and MERS (Middle East Respiratory Syndrome, MERS-CoV).

In one embodiment, the viral infection is by a virus from the bunyaviridae family of viruses. In one embodiment, the viral infection is by a bunyaviridae virus selected from the group consisting of Rift Valley fever.

The present disclosure contemplates the treatment of any viral infection that targets the fatty acid synthesis pathway in a host, and in particular by modulating the activity of fatty acid synthase. For example, the present methods can be used to treat infections caused by Abelson leukemia virus, Abelson murine leukemia virus, Abelson's virus, Acute laryngotracheobronchitis virus, Adelaide River virus, Adeno associated virus group, Adenovirus, African horse sickness virus, African swine fever virus, AIDS virus, Aleutian mink disease parvovirus, Alpharetrovirus, Alphavirus, ALV related virus, Amapari virus, Aphthovirus, Aquareovirus, Arbovirus, Arbovirus C, arbovirus group A, arbovirus group B, Arenavirus group, Argentine hemorrhagic fever virus, Argentine hemorrhagic fever virus, Arterivirus, Astrovirus, Ateline herpesvirus group, Aujezky's disease virus, Aura virus, Ausduk disease virus, Australian bat lyssavirus, Aviadenovirus, avian erythroblastosis virus, avian infectious bronchitis virus, avian leukemia virus, avian leukosis virus, avian lymphomatosis virus, avian myeloblastosis virus, avian paramyxovirus, avian pneumoencephalitis virus, avian reticuloendotheliosis virus, avian sarcoma virus, avian type C retrovirus group, Avihepadnavirus, Avipoxvirus, B virus, B19 virus, Babanki virus, baboon herpesvirus, baculovirus, Barmah Forest virus, Bebaru virus, Berrimah virus, Betaretrovirus, Birnavirus, Bittner virus, BK virus, Black Creek Canal virus, bluetongue virus, Bolivian hemorrhagic fever virus, Boma disease virus, border disease of sheep virus, borna virus, bovine alphaherpesvirus 1, bovine alphaherpesvirus 2, bovine coronavirus, bovine ephemeral fever virus, bovine immunodeficiency virus, bovine leukemia virus, bovine leukosis virus, bovine mammillitis virus, bovine papillomavirus, bovine papular stomatitis virus, bovine parvovirus, bovine syncytial virus, bovine type C oncovirus, bovine viral diarrhea virus, Buggy Creek virus, bullet shaped virus group, Bunyamwera virus supergroup, Bunyavirus, Burkitt's lymphoma virus, Bwamba Fever, CA virus, Calicivirus, California encephalitis virus, camelpox virus, canarypox virus, canid herpesvirus, canine coronavirus, canine distemper virus, canine herpesvirus, canine minute virus, canine parvovirus, Cano Delgadito virus, caprine arthritis virus, caprine encephalitis virus, Caprine Herpes Virus, Capripox virus, Cardiovirus, caviid herpesvirus 1, Cercopithecid herpesvirus 1, cercopithecine herpesvirus 1, Cercopithecine herpesvirus 2, Chandipura virus, Changuinola virus, channel catfish virus, Charleville virus, chickenpox virus, Chikungunya virus, chimpanzee herpesvirus, chub reovirus, chum salmon virus, Cocal virus, Coho salmon reovirus, coital exanthema virus, Colorado tick fever virus, Coltivirus, Columbia SK virus, common cold virus, contagious ecthyma virus, contagious pustular dermatitis virus, Coronavirus, Corriparta virus, coryza virus, cowpox virus, coxsackie virus, CPV (cytoplasmic polyhedrosis virus), cricket paralysis virus, Crimean-Congo hemorrhagic fever virus, croup associated virus, Cryptovirus, Cypovirus, Cytomegalovirus, cytomegalovirus group, cytoplasmic polyhedrosis virus, deer papillomavirus, deltaretrovirus, dengue virus, Densovirus, Dependovirus, Dhori virus, diploma virus, *Drosophila* C virus, duck hepatitis B virus, duck hepatitis virus 1, duck hepatitis virus 2, duovirus, Duvenhage virus, Deformed wing virus DWV, eastern equine encephalitis virus, eastern equine encephalomyelitis virus, EB virus, Ebola virus, Ebola-like virus, echo virus, echovirus, echovirus 10, echovirus 28, echovirus 9, ectromelia virus, EEE virus, EIA virus, EIA virus, encephalitis virus, encephalomyocarditis group virus, encephalomyocarditis virus, Enterovirus, enzyme elevating virus, enzyme elevating virus (LDH), epidemic hemorrhagic fever virus, epizootic hemorrhagic disease virus, Epstein-Barr virus, equid alphaherpesvirus 1, equid alphaherpesvirus 4, equid herpesvirus 2, equine abortion virus, equine arteritis virus, equine encephalosis virus, equine infectious anemia virus, equine morbillivirus, equine rhinopneumonitis virus, equine rhinovirus, Eubenangu virus, European elk papillomavirus, European swine fever virus, Everglades virus, Eyach virus, felid herpesvirus 1, feline calicivirus, feline fibrosarcoma virus, feline herpesvirus, feline immunodeficiency virus, feline infectious peritonitis virus, feline leukemia/sarcoma virus, feline leukemia virus, feline panleukopenia virus, feline parvovirus, feline sarcoma virus, feline syncytial virus, Filovirus, Flanders virus, Flavivirus, foot and mouth disease virus, Fort Morgan virus, Four Corners hantavirus, fowl adenovirus 1, fowlpox virus, Friend virus, Gammaretrovirus, GB hepatitis virus, GB virus, German measles virus, Getah virus, gibbon ape leukemia virus, glandular fever virus, goatpox virus, golden shinner virus, Gonometa virus, goose parvovirus, granulosis virus, Gross' virus, ground squirrel hepatitis B virus, group A arbovirus, Guanarito virus, guinea pig cytomegalovirus, guinea pig type C virus, Hantaan virus, Hantavirus, hard clam reovirus, hare fibroma virus, HCMV (human cytomegalovirus), hemadsorption virus 2, hemagglutinating virus of Japan, hemorrhagic fever virus, hendra virus, Henipaviruses, Hepadnavirus, hepatitis A virus, hepatitis B virus group, hepatitis C virus, hepatitis D virus, hepatitis delta virus, hepatitis E virus, hepatitis F virus, hepatitis G virus, hepatitis nonA nonB virus, hepatitis virus, hepatitis virus (nonhuman), hepatoencephalomyelitis reovirus 3, Hepatovirus, heron hepatitis B virus, herpes B virus, herpes simplex virus, herpes simplex virus 1, herpes simplex virus 2, herpesvirus, herpesvirus 7, Herpesvirus ateles, Herpesvirus hominis, Herpesvirus infection, Herpesvirus saimiri, Herpesvirus suis, Herpesvirus varicellae, Highlands J virus, Hirame rhabdovirus, hog cholera virus, human adenovirus 2, human alphaherpesvirus 1, human alphaherpesvirus 2, human alphaherpesvirus 3, human B lymphotropic virus, human betaherpesvirus 5, human coronavirus, human cytomegalovirus group, human foamy virus, human gammaherpesvirus 4, human gammaherpesvirus 6, human hepatitis A virus, human herpesvirus 1 group, human herpesvirus 2 group, human herpesvirus 3 group, human herpesvirus 4 group, human herpesvirus 6, human herpesvirus 8, human immunodeficiency virus, human immunodeficiency virus 1, human immunodeficiency virus 2, human papillomavirus, human T cell leukemia virus, human T cell leukemia virus I, human T cell leukemia virus II, human T cell leukemia virus III, human T cell lymphoma virus I, human T cell lymphoma virus II, human T cell lymphotropic virus type 1, human T cell lymphotropic virus type 2, human T lymphotropic virus I, human T lymphotropic virus II, human T lymphotropic virus III, Ichnovirus, infantile gastroenteritis virus, infectious bovine rhinotracheitis virus, infectious haematopoietic necrosis virus, infectious pancreatic necrosis virus, influenza virus A, influenza virus B, influenza virus C, influenza virus D, influenza virus pr8, insect iridescent virus, insect virus, iridovirus, Japanese B virus, Japanese encephalitis virus, JC virus, Jimin virus, Kaposi's sarcoma-associated herpesvirus, Kemerovo virus, Kilham's rat virus, Klamath virus, Kolongo virus, Korean hemorrhagic fever virus, kumba virus, Kysanur forest disease virus, Kyzylagach virus, La Crosse virus, lactic dehydrogenase elevating virus, lactic dehydrogenase virus, Lagos bat virus, Langur virus, lapine parvovirus, Lassa fever virus, Lassa virus, latent rat virus, LCM virus, Leaky virus, Lentivirus, Leporipoxvirus, leukemia virus, leukovirus, lumpy skin disease virus, lymphadenopathy associated virus, Lymphocryptovirus, lymphocytic choriomeningitis virus, lymphoproliferative virus group, Machupo virus, mad itch virus, mammalian type B oncovirus group, mammalian type B retroviruses, mammalian type C retrovirus group, mammalian type D retroviruses, mammary tumor virus, Mapuera virus, Marburg virus, Marburg-like virus, Mason Pfizer monkey virus, Mastadenovirus, Mayaro virus, ME virus, measles virus, Menangle virus, Mengo virus, Mengovirus, Middelburg virus, milkers nodule virus, mink enteritis virus, minute virus of mice, MLV related virus, MM virus, Mokola virus, Molluscipoxvirus, Molluscum contagiosum virus, monkey B virus, monkeypox virus, Mononegavirales, Morbillivirus, Mount Elgon bat virus, mouse cytomegalovirus, mouse encephalomyelitis virus, mouse hepatitis virus, mouse K virus, mouse leukemia virus, mouse mammary tumor virus, mouse minute virus, mouse pneumonia virus, mouse poliomyelitis virus, mouse polyomavirus, mouse sarcoma virus, mousepox virus, Mozambique virus, Mucambo virus, mucosal disease virus, mumps virus, murid betaherpesvirus 1, murid cytomegalovirus 2, murine cytomegalovirus group, murine encephalomyelitis virus, murine hepatitis virus, murine leukemia virus, murine nodule inducing virus, murine polyomavirus, murine sarcoma virus, Muromegalovirus, Murray Valley encephalitis virus, myxoma virus, Myxovirus, Myxovirus multiforme, Myxovirus parotitidis, Nairobi sheep disease virus, Nairovirus, Nanirnavirus, Nariva virus, Ndumo virus, Neethling virus, Nelson Bay virus, neurotropic virus, New World Arenavirus, newborn pneumonitis virus, Newcastle disease virus, Nipah virus, noncytopathogenic virus, Norwalk virus, nuclear polyhedrosis virus (NPV), nipple neck virus, O'nyong'nyong virus, Ockelbo virus, oncogenic virus, oncogenic viruslike particle, oncornavirus, Orbivirus, Orf virus, Oropouche virus, Orthohepadnavirus, Orthomyxovirus, Orthopoxvirus, Orthoreovirus, Orungo, ovine papillomavirus, ovine catarrhal fever virus, owl monkey herpesvirus, Palyam virus, Papillomavirus, Papillomavirus sylvilagi, Papovavirus, parainfluenza virus, parainfluenza virus type 1, parainfluenza virus type 2, parainfluenza virus type 3, parainfluenza virus type 4, Paramyxovirus, Parapoxvirus, paravaccinia virus, Parvovirus, Parvovirus B19, parvovirus group, Pestivirus, Phlebovirus, phocine distemper virus, Picodnavirus, Picornavirus, pig cytomegalovirus-pigeonpox virus, Piry virus, Pixuna virus, pneumonia virus of mice, Pneumovirus, poliomyelitis virus, poliovirus, Polydnavirus, polyhedral virus, polyoma virus, Polyomavirus, Polyomavirus bovis, Polyomavirus cercopitheci, Polyomavirus hominis 2, Polyomavirus maccacae 1, Polyomavirus muris 1, Polyomavirus muris 2, Polyomavirus papionis 1, Polyomavirus papionis 2, Polyomavirus sylvilagi, Pongine herpesvirus 1, porcine epidemic diarrhea virus, porcine hemagglutinating encephalomyelitis virus, porcine parvovirus, porcine transmissible gastroenteritis virus, porcine type C virus, pox virus, poxvirus, poxvirus variolae, Prospect Hill virus, Provirus, pseudocowpox virus, pseudorabies virus, psittacinepox virus, quailpox virus, rabbit fibroma virus, rabbit kidney vaculolating virus, rabbit papillomavirus, rabies virus, raccoon parvovirus, raccoonpox virus, Ranikhet virus, rat cytomegalovirus, rat parvovirus, rat virus, Rauscher's virus, recombinant vaccinia virus, recombinant virus, reovirus, reovirus 1, reovirus 2, reovirus 3, reptilian type C virus, respiratory infection virus, respiratory syncytial virus, respiratory virus, reticuloendotheliosis virus, Rhabdovirus, Rhabdovirus carpia, Rhadinovirus, Rhinovirus, Rhizidiovirus, Rift Valley fever virus, Riley's virus, rinderpest virus, RNA tumor virus, Ross River virus, Rotavirus, rougeole virus, Rous sarcoma virus, rubella virus, rubeola virus, Rubivirus, Russian autumn encephalitis virus, SA 11 simian virus, SA2 virus, Sabia virus, Sagiyama virus, Saimirine herpesvirus 1, salivary gland virus, sandfly fever virus group, Sandjimba virus, SARS virus, SDAV (sialodacryoadenitis virus), sealpox virus, Semliki Forest Virus, Seoul virus, sheeppox virus, Shope fibroma virus, Shope papilloma virus, simian foamy virus, simian hepatitis A virus, simian human immunodeficiency virus, simian immunodeficiency virus, simian parainfluenza virus, simian T cell lymphotrophic virus, simian virus, simian virus 40, Simplexvirus, Sin Nombre virus, Sindbis virus, smallpox virus, South American hemorrhagic fever viruses, sparrowpox virus, Spumavirus, squirrel fibroma virus, squirrel monkey retrovirus, SSV 1 virus group, STLV (simian T lymphotropic virus) type I, STLV (simian T lymphotropic virus) type II, STLV (simian T lymphotropic virus) type III, stomatitis papulosa virus, submaxillary virus, suid alphaherpesvirus 1, suid herpesvirus 2, Suipoxvirus, swamp fever virus, swinepox virus, Swiss mouse leukemia virus, TAC virus, Tacaribe complex virus, Tacaribe virus, Tanapox virus, Taterapox virus, Tench reovirus, Theiler's encephalomyelitis virus, Theiler's virus, Thogoto virus, Thottapalayam virus, Tick borne encephalitis virus, Tioman virus, Togavirus, Torovirus, tumor virus, Tupaia virus, turkey rhinotracheitis virus, turkeypox virus, type C retroviruses, type D oncovirus, type D retrovirus group, ulcerative disease rhabdovirus, Una virus, Uukuniemi virus group, vaccinia virus, vacuolating virus, varicella zoster virus, Varicellovirus, Varicola virus, variola major virus, variola virus, Vasin Gishu disease virus, VEE virus, Venezuelan equine encephalitis virus, Venezuelan equine encephalomyelitis virus, Venezuelan hemorrhagic fever virus, vesicular stomatitis virus, Vesiculovirus, Vilyuisk virus, viper retrovirus, viral haemorrhagic septicemia virus, Visna Maedi virus, Visna virus, volepox virus, VSV (vesicular stomatitis virus), Wallal virus, Warrego virus, wart virus, WEE virus, West Nile virus, western equine encephalitis virus, western equine encephalomyelitis virus, Whataroa virus, Winter Vomiting Virus, woodchuck hepatitis B virus, woolly monkey sarcoma virus, wound tumor virus, WRSV virus, Yaba monkey tumor virus, Yaba virus, Yatapoxvirus, yellow fever virus, and the Yug Bogdanovac virus.

Utility in Metabolic Disorders

In various aspects, the compounds of the present disclosure have utility in the treating of metabolic diseases. FASN has been demonstrated to be involved in regulation of glucose, lipids and cholesterol metabolism. Mice with a liver-specific inactivation of FASN have normal physiology unless fed a zero-fat diet, in which case they develop hypoglycemia and fatty liver, both of which are reversed with dietary fat. (Chakravarthy, M. V., et al. (2005) *Cell Metabolism* 1:309-322). Db/+ mice fed a high fructose diet exhibit reduced liver triglyceride levels and improved insulin sensitivity when treated for 28 days with platensimycin, a covealent inhibitor of FASN. (Wu, M. et al. (2011) *PNAS* 108(13):5378-5383). Ambient glucose levels are also reduced in db/db mice following treatment with platensimycin. These results provide evidence that inhibiting FASN can yield therapeutically relevant benefits in animal models of diabetes and related metabolic disorders. Thus the disclosed FASN inhibitors are useful in the treatment of disorders characterized by disregulation in these systems. Without limitation, examples include steatosis and diabetes.

Anticancer Activity

In various aspects, the present disclosure provides methods for treating cancer in subject, the method comprising administering to a subject in need of such treatment an effective amount of a compound of Structures (I), (II), (III), (IV), (V), (VI), (VII), (VIII), (IX), (X), (XI) or as provided in Table 1. In further aspects, compounds having Structure (I), (II), (III), (IV), (V), (VI), (VII), (VIII), (IX), (X), (XI) or as provided in Table 1 can be used for the manufacture of a medicament for treating cancer.

In certain aspects, the present disclosure provides a method for inhibiting tumor cell growth in a subject, the method comprising administering to a subject in need of such treatment an effective amount of a compound of Structure (I), (II), (III), (IV), (V), (VI), (VII), (VIII), (IX), (X), (XI) or as provided in Table 1. In further aspects, the tumor can be derived from ovary, breast, lung, thyroid, lymph node, kidney, ureter, bladder, ovary, teste, prostate, bone, skeletal muscle, bone marrow, stomach, esophagus, small bowel, colon, rectum, pancreas, liver, smooth muscle, brain, spinal cord, nerves, ear, eye, nasopharynx, oropharynx, salivary gland, or heart tissue. In certain aspects, the present compounds can be administered concurrently with one or more additional anti-cancer treatments.

In a further embodiment, the tumor is a cancer selected from the group consisting of breast cancer; antle cell lymphoma; renal cell carcinoma; acute myelogenous leukemia (AML); chronic myelogenous leukemia (CML); diffuse large B cell lymphoma (DLBCL); sarcoma; rhabdomyosarcoma; ovarian cancer; endometrial tumors; non small cell lung carcinoma (NSCLC); small cell, squamous, large cell and adenocarcinoma; lung cancer; colon cancer; colorectal tumors; KRAS-mutated colorectal tumors; gastric carcinomas; hepatocellular tumors; liver tumors; primary melanomas; pancreatic tumorscancer; prostate carcinoma; thyroid carcinoma; follicular thyroid carcinoma; anaplastic large cell lymphoma (ALCL); hamaratomas, angiomyelolipomas, TSC-associated and sporadic lymphangioleiomyomatosis: Cowden's disease (multiple hamaratoma syndrome); sclerosing hemangioma; Peutz-Jeghers syndrome (PJS); head and neck cancer; neurofibromatosis; macular degeneration; macular edema; myeloid leukemia; systemic lupus; and autoimmune lymphoproliferative syndrome (ALPS).

In certain aspects, the present disclosure provides a method for treating pancreatic cancer in a subject, the method comprising administering to a subject in need of such treatment an effective amount of a compound of Structures (I), (II), (III), (IV), (V), (VI), (VII), (VIII), (IX), (X), (XI) or as provided in Table 1.

In certain aspects, the present disclosure provides for a method of treating colon cancer in a subject, the method comprising administering to a subject in need of such treatment an effective amount of a compound of Structures (I), (II), (III), (IV), (V), (VI), (VII), (VIII), (IX), (X), (XI) or as provided in Table 1.

Rapidly proliferating cancer cells activate the fatty acid synthesis pathway to supply the high levels of lipids needed for membrane assembly and oxidative metabolism. (Flavin, R. et al. (2010) *Future Oncology.* 6(4):551-562) Inhibitors of fatty acid synthesis have demonstrated in vivo activity in preclinical cancer models. (Orita, H. et al. (2007) *Clinical Cancer Research.* 13(23):7139-7145 and Puig, T. et al. (2011) *Breast Cancer Research,* 13(6):R131) Additionally, fatty acid synthesis supports new blood vessel formation and inhibitors of this pathway have activity in in vitro models of angiogenesis. (Browne, C. D., et al. (2006) *The FASEB Journal,* 20(12):2027-2035). The presently disclosed compounds demonstrated the ability to selectively induce cell-cycle arrest in HUVEC cells without causing general cell death by apoptosis. See EXAMPLES.

The cancer treatment of the present invention includes an anti-tumor effect that may be assessed by conventional means such as the response rate, the time to disease progression and/or the survival rate. Anti-tumor effects of the present invention include, but are not limited to, inhibition of tumor growth, tumor growth delay, regression of tumor, shrinkage of tumor, increased time to regrowth of tumor on cessation of treatment and slowing of disease progression. For example, it is expected that when the combination of the present invention is administered to a warm-blooded animal such as a human, in need of treatment for cancer involving a solid tumor, such a method of treatment will produce an effect, as measured by, for example, one or more of: the extent of the anti-tumor effect, the response rate, the time to disease progression and the survival rate.

Methods of Treatment

Also provided herein are pharmaceutical compositions comprising the compounds of the present disclosure. The present compositions and methods have antiviral and/or anticancer activity.

In various aspects, the present disclosure provides pharmaceutical compositions comprising any one of the compounds of Structures (I), (II), (III), (IV), (V), (VI), (VII), (VIII), (IX), (X) or (XI) and a pharmaceutically acceptable carrier, excipient, or diluent.

In certain aspects, the present disclosure provides pharmaceutical compositions comprising any one of the compounds of Table 1 and a pharmaceutically acceptable carrier, excipient, or diluent.

Certain aspects of the present disclosure relates to methods of using pharmaceutical compositions and kits comprising one or more agents that inhibit the fatty acid synthesis pathway to inhibit or decrease a viral infection or for the treatment of cancer. Certain aspects of the present disclosure relates to methods of using pharmaceutical compositions and kits comprising one or more agents that inhibit fatty acid synthase to inhibit or decrease a viral infection or for the treatment of cancer. Another aspect of the present invention provides methods, pharmaceutical compositions, and kits for the treatment of animal subjects having a viral infection or cancer or at risk of developing a viral infection or cancer. The term "subject" as used herein includes humans as well as other mammals. The term "treating" as used herein includes achieving a therapeutic benefit and/or a prophylactic benefit. By therapeutic benefit is meant eradication or amelioration of the underlying viral infection. Also, a therapeutic benefit is achieved with the eradication or amelioration of one or more of the physiological symptoms associated with the underlying viral infection such that an improvement is observed in the animal subject, notwithstanding the fact that the subject can still be afflicted with the underlying virus.

For aspects where a prophylactic benefit is desired, a pharmaceutical composition of the invention can be administered to a patient at risk of developing viral infection such as HRV, or HIV, or to a patient reporting one or more of the physiological symptoms of a viral infection, even though a diagnosis of the condition may not have been made. Administration can prevent the viral infection from developing, or it can reduce, lessen, shorten and/or otherwise ameliorate the viral infection that develops. The pharmaceutical composition can modulate the fatty acid synthesis pathway, e.g., FASN gene expression or FASN protein activity. Wherein, the term modulate includes inhibition of the fatty acid synthesis pathway, e.g., FASN gene expression or FASN protein activity or alternatively activation of the fatty acid synthesis pathway, e.g., FASN gene expression or FASN protein activity.

Reducing the activity of the fatty acid synthesis pathway, e.g., FASN gene expression or FASN protein activity, is also referred to as "inhibiting" the fatty acid synthesis pathway, e.g., FASN gene expression or FASN protein activity. The term "inhibits" and its grammatical conjugations, such as "inhibitory," do not require complete inhibition, but refer to a reduction in fatty acid synthesis activity, e.g., FASN gene expression or FASN protein activity. In another aspect, such reduction is by at least 50%, at least 75%, at least 90%, and can be by at least 95% of the activity of the enzyme in the absence of the inhibitory effect, e.g., in the absence of an inhibitor. Conversely, the phrase "does not inhibit" and its grammatical conjugations refer to situations where there is less than 20%, less than 10%, and can be less than 5%, of reduction in enzyme activity in the presence of the agent. Further the phrase "does not substantially inhibit" and its grammatical conjugations refer to situations where there is less than 30%, less than 20%, and in some aspects less than 10% of reduction in enzyme activity in the presence of the agent.

Increasing the activity of the fatty acid synthesis pathway, e.g., FASN gene expression or FASN protein activity, is also referred to as "activating" the fatty acid synthesis pathway, e.g., FASN gene expression or FASN protein activity. The term "activated" and its grammatical conjugations, such as "activating," do not require complete activation, but refer to an increase in fatty acid synthesis pathway activity, e.g., FASN gene expression or FASN protein activity. In another aspect such increase is by at least 50%, at least 75%, at least 90%, and can be by at least 95% of the activity of the enzyme in the absence of the activation effect, e.g., in the absence of an activator. Conversely, the phrase "does not activate" and its grammatical conjugations refer to situations where there is less than 20%, less than 10%, and can be less than 5%, of an increase in enzyme activity in the presence of the agent. Further the phrase "does not substantially activate" and its grammatical conjugations refer to situations where there is less than 30%, less than 20%, and in another aspect less than 10% of an increase in enzyme activity in the presence of the agent.

The ability to reduce enzyme activity is a measure of the potency or the activity of an agent, or combination of agents, towards or against the enzyme. Potency can be measured by cell free, whole cell and/or in vivo assays in terms of IC50, $K_i$ and/or ED50 values. An IC50 value represents the concentration of an agent required to inhibit enzyme activity by half (50%) under a given set of conditions. A $K_i$ value represents the equilibrium affinity constant for the binding of an inhibiting agent to the enzyme. An ED50 value represents the dose of an agent required to effect a half-maximal response in a biological assay. Further details of these measures will be appreciated by those of ordinary skill in the art, and can be found in standard texts on biochemistry, enzymology, and the like.

The present invention also includes kits that can be used to treat viral infections or treat cancer. These kits comprise an agent or combination of agents that inhibit the fatty acid synthesis pathway, e.g., FASN gene expression or FASN protein activity, and optionally instructions teaching the use of the kit according to the various methods and approaches described herein. Such kits can also include information, such as scientific literature references, package insert materials, clinical trial results, and/or summaries of these and the like, which indicate or establish the activities and/or advantages of the agent. Such information can be based on the results of various studies, for example, studies using experimental animals involving in vivo models and studies based on human clinical trials. Kits described herein can be provided, marketed and/or promoted to health providers, including physicians, nurses, pharmacists, formulary officials, and the like.

Formulations, Routes of Administration, and Effective Doses

Yet another aspect of the present invention relates to formulations, routes of administration and effective doses for pharmaceutical compositions comprising an agent or combination of agents of the instant invention. Such pharmaceutical compositions can be used to treat viral infections as described above.

Compounds of the invention can be administered as pharmaceutical formulations including those suitable for oral (including buccal and sub-lingual), rectal, nasal, topical, transdermal patch, pulmonary, vaginal, suppository, or parenteral (including intramuscular, intraarterial, intrathecal, intradermal, intraperitoneal, subcutaneous and intravenous) administration or in a form suitable for administration by aerosolization, inhalation or insufflation. General information on drug delivery systems can be found in Ansel et al., Pharmaceutical Dosage Forms and Drug Delivery Systems (Lippencott Williams & Wilkins, Baltimore Md. (1999).

In various aspects, the pharmaceutical composition includes carriers and excipients (including but not limited to buffers, carbohydrates, mannitol, proteins, polypeptides or amino acids such as glycine, antioxidants, bacteriostats, chelating agents, suspending agents, thickening agents and/or preservatives), water, oils including those of petroleum, animal, vegetable or synthetic origin, such as peanut oil, soybean oil, mineral oil, sesame oil and the like, saline solutions, aqueous dextrose and glycerol solutions, flavoring agents, coloring agents, detackifiers and other acceptable additives, adjuvants, or binders, other pharmaceutically acceptable auxiliary substances as required to approximate physiological conditions, such as pH buffering agents, tonicity adjusting agents, emulsifying agents, wetting agents and the like. Examples of excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. In another aspect, the pharmaceutical preparation is substantially free of preservatives. In another aspect, the pharmaceutical preparation can contain at least one preservative. General methodology on pharmaceutical dosage forms is found in Ansel et al., Pharmaceutical Dosage Forms and Drug Delivery Systems (Lippencott Williams & Wilkins, Baltimore Md. (1999)). It will be recognized that, while any suitable carrier known to those of ordinary skill in the art can be employed to administer the compositions of this invention, the type of carrier will vary depending on the mode of administration.

Compounds can also be encapsulated within liposomes using well-known technology. Biodegradable microspheres can also be employed as carriers for the pharmaceutical compositions of this invention. Suitable biodegradable microspheres are disclosed, for example, in U.S. Pat. Nos. 4,897,268; 5,075,109; 5,928,647; 5,811,128; 5,820,883; 5,853,763; 5,814,344 and 5,942,252.

The compound can be administered in liposomes or microspheres (or microparticles). Methods for preparing liposomes and microspheres for administration to a patient are well known to those of skill in the art. U.S. Pat. No. 4,789,734, the contents of which are hereby incorporated by reference, describes methods for encapsulating biological materials in liposomes. Essentially, the material is dissolved in an aqueous solution, the appropriate phospholipids and lipids added, along with surfactants if required, and the material dialyzed or sonicated, as necessary. A review of known methods is provided by G. Gregoriadis, Chapter 14, "Liposomes," Drug Carriers in Biology and Medicine, pp. 2.sup.87-341 (Academic Press, 1979).

Microspheres formed of polymers or proteins are well known to those skilled in the art, and can be tailored for passage through the gastrointestinal tract directly into the blood stream. Alternatively, the compound can be incorporated and the microspheres, or composite of microspheres, implanted for slow release over a period of time ranging from days to months. See, for example, U.S. Pat. Nos. 4,906,474, 4,925,673 and 3,625,214, and Jein, TIPS 19:155-157 (1998), the contents of which are hereby incorporated by reference.

The concentration of drug can be adjusted, the pH of the solution buffered and the isotonicity adjusted to be compatible with intravenous injection, as is well known in the art.

The compounds of the invention can be formulated as a sterile solution or suspension, in suitable vehicles, well known in the art. The pharmaceutical compositions can be sterilized by conventional, well-known sterilization techniques, or can be sterile filtered. The resulting aqueous solutions can be packaged for use as is, or lyophilized, the lyophilized preparation being combined with a sterile solution prior to administration. Suitable formulations and additional carriers are described in Remington "The Science and Practice of Pharmacy" (20$^{th}$ Ed., Lippincott Williams & Wilkins, Baltimore Md.), the teachings of which are incorporated by reference in their entirety herein.

The agents or their pharmaceutically acceptable salts can be provided alone or in combination with one or more other agents or with one or more other forms. For example a formulation can comprise one or more agents in particular proportions, depending on the relative potencies of each agent and the intended indication. For example, in compositions for targeting two different host targets, and where potencies are similar, about a 1:1 ratio of agents can be used. The two forms can be formulated together, in the same dosage unit e.g., in one cream, suppository, tablet, capsule, aerosol spray, or packet of powder to be dissolved in a beverage; or each form can be formulated in a separate unit, e.g., two creams, two suppositories, two tablets, two capsules, a tablet and a liquid for dissolving the tablet, two aerosol sprays, or a packet of powder and a liquid for dissolving the powder, etc.

The term "pharmaceutically acceptable salt" means those salts which retain the biological effectiveness and properties of the agents used in the present invention, and which are not biologically or otherwise undesirable. For example, a pharmaceutically acceptable salt does not interfere with the beneficial effect of an agent of the invention in inhibiting the fatty acid synthesis pathway, e.g., inhibiting FASN gene expression or FASN protein activity.

Typical salts are those of the inorganic ions, such as, for example, sodium, potassium, calcium, magnesium ions, and the like. Such salts include salts with inorganic or organic acids, such as hydrochloric acid, hydrobromic acid, phosphoric acid, nitric acid, sulfuric acid, methanesulfonic acid, p-toluenesulfonic acid, acetic acid, fumaric acid, succinic acid, lactic acid, mandelic acid, malic acid, citric acid, tartaric acid or maleic acid. In addition, if the agent(s) contain a carboxy group or other acidic group, it can be converted into a pharmaceutically acceptable addition salt with inorganic or organic bases. Examples of suitable bases include sodium hydroxide, potassium hydroxide, ammonia, cyclohexylamine, dicyclohexyl-amine, ethanolamine, diethanolamine, triethanolamine, and the like.

A pharmaceutically acceptable ester or amide refers to those which retain biological effectiveness and properties of the agents used in the present invention, and which are not biologically or otherwise undesirable. For example, the ester or amide does not interfere with the beneficial effect of an agent of the invention in inhibiting the fatty acid synthesis pathway, e.g., inhibiting FASN gene expression or FASN protein activity. Typical esters include ethyl, methyl, isobutyl, ethylene glycol, and the like. Typical amides include unsubstituted amides, alkyl amides, dialkyl amides, and the like.

In another aspect, an agent can be administered in combination with one or more other compounds, forms, and/or agents, e.g., as described above. Pharmaceutical compositions comprising combinations of a fatty acid synthesis pathway inhibitor e.g., an inhibitor or FASN gene expression or FASN protein activity with one or more other active agents can be formulated to comprise certain molar ratios. For example, molar ratios of about 99:1 to about 1:99 of a fatty acid synthesis pathway inhibitor e.g., an inhibitor of FASN gene expression or FASN protein activity, to the other active agent can be used. In some subset of the aspects, the range of molar ratios of fatty acid synthesis pathway inhibitor e.g., an inhibitor of FASN gene expression or FASN protein activity: other active agent is selected from about 80:20 to about 20:80; about 75:25 to about 25:75, about 70:30 to about 30:70, about 66:33 to about 33:66, about 60:40 to about 40:60; about 50:50; and about 90:10 to about 10:90. The molar ratio of a fatty acid synthesis pathway inhibitor e.g., an inhibitor of FASN gene expression or FASN protein activity: other active agent can be about 1:9, and in another aspect can be about 1:1. The two agents, forms and/or compounds can be formulated together, in the same dosage unit e.g., in one cream, suppository, tablet, capsule, or packet of powder to be dissolved in a beverage; or each agent, form, and/or compound can be formulated in separate units, e.g., two creams, suppositories, tablets, two capsules, a tablet and a liquid for dissolving the tablet, an aerosol spray a packet of powder and a liquid for dissolving the powder, etc.

If necessary or desirable, the agents and/or combinations of agents can be administered with still other agents. The choice of agents that can be co-administered with the agents and/or combinations of agents of the instant invention can depend, at least in part, on the condition being treated. Agents of particular use in the formulations of the present invention include, for example, any agent having a therapeutic effect for a viral infection, including, e.g., drugs used to treat inflammatory conditions. For example, in treatments for HRV, in some aspects formulations of the instant invention can additionally contain one or more conventional anti-inflammatory drugs, such as an NSAID, e.g., ibuprofen, naproxen, acetaminophen, ketoprofen, or aspirin. In some alternative aspects for the treatment of influenza formulations of the instant invention can additionally contain one or more conventional influenza antiviral agents, such as amantadine, rimantadine, zanamivir, and oseltamivir. In treatments for retroviral infections, such as HIV, formulations of the instant invention can additionally contain one or more conventional antiviral drug, such as protease inhibitors (lopinavir/ritonavir (Kaletra), indinavir (Crixivan), ritonavir (Norvir), nelfinavir (Viracept), saquinavir hard gel capsules (Invirase), atazanavir (Reyataz), amprenavir (Agenerase), fosamprenavir (Telzir), tipranavir (Aptivus)), reverse transcriptase inhibitors, including non-Nucleoside and Nucleoside/nucleotide inhibitors (AZT (zidovudine, Retrovir), ddI (didanosine, Videx), 3TC (lamivudine, Epivir), d4T (stavudine, Zerit), abacavir (Ziagen), FTC (emtricitabine, Emtriva), tenofovir (Viread), efavirenz (Sustiva) and nevirapine (Viramune)), fusion inhibitors T20 (enfuvirtide, Fuzeon), integrase inhibitors (MK-0518 and GS-9137), and maturation inhibitors (PA-457 (Bevirimat)). As another example, formulations can additionally contain one or more supplements, such as vitamin C, E or other antioxidants.

In certain aspects, the scompounds of the present disclosure can be administered in combination with a known cancer therapeutic. For example, the compounds can be administered in combination with paclitaxel (commercially available as Taxol, Bristol-Myers Squibb), doxorubicin (also known under the trade name Adriamycin), vincristine (known under the trade names Oncovin, Vincasar PES, and Vincrex), actinomycin D, altretamine, asparaginase, bleomycin, busulphan, cabazitaxel, capecitabine, carboplatin, carmustine, chlorambucil, cisplatin, cyclophosphamide, cytarabine, dacarbazine, daunorubicin, docetaxel, epirubicin, etoposide, fludarabine, fluorouracil, gemcitabine, hydroxyurea, idarubicin, ifosfamide, irinotecan, lomustine, melphalan, mercaptopurine, methotrexate, mitomycin, mitozantrone, oxaliplatin, procarbazine, steroids, streptozocin, taxotere, tamozolomide, thioguanine, thiotepa, tomudex, topotecan, treosulfan, UFT (uracil-tegufur), vinblastine, vindesine, agents targeting immune modualtors such as PD-1, PDL-1, and IDO1, e.g. nivolumab, pembrolizumab, MPDL3280A, and MEDI4736; agents targeting DNA repair deficiency, e.g. olaparib; agents targeting receptor tyrosine kinases such as EGFR, ERBB2, c-MET, VEGFR2, and IGFR1, e.g. erlotinib, necitumumab, traztuzamab, pertuzamab, lapatinib, crizotinib, cabozantinib, onartuamab, ramucirumab, or bevacizumab; agents tarting hormone receptors such as the androgen and estrogen receptors, e.g. enzalutamide, abiraterone, or tamoxifen; agents targeting the MAP kinase or PI3K-AKT pathways, e.g. cobimetinib, vemurafenib, and everolimus; Her2 (ErbB2) pathway blockers such as lapatinib, trastuzumab, and Kadyzla; mTOR blockers such as ralapogs (eg. sirolimus); mTORC1/mTORC1 inhibitors; Angiogenesis or VEGFR pathway blockers such as avastin, nexavar or sutent; Aromatase modulators such as exemtesane or femora; Androgen signaling modulators such as enzalutamide, bicalutamide; and B-RAF blockers such as Tafinlar or Zelboraf, or the like.

The agent(s) (or pharmaceutically acceptable salts, esters or amides thereof) can be administered per se or in the form of a pharmaceutical composition wherein the active agent(s) is in an admixture or mixture with one or more pharmaceutically acceptable carriers. A pharmaceutical composition, as used herein, can be any composition prepared for administration to a subject. Pharmaceutical compositions for use in accordance with the present invention can be formulated in conventional manner using one or more physiologically acceptable carriers, comprising excipients, diluents, and/or auxiliaries, e.g., which facilitate processing of the active agents into preparations that can be administered. Proper formulation can depend at least in part upon the route of administration chosen. The agent(s) useful in the present invention, or pharmaceutically acceptable salts, esters, or amides thereof, can be delivered to a patient using a number of routes or modes of administration, including oral, buccal, topical, rectal, transdermal, transmucosal, subcutaneous, intravenous, and intramuscular applications, as well as by inhalation.

For oral administration, the agents can be formulated readily by combining the active agent(s) with pharmaceutically acceptable carriers well known in the art. Such carriers enable the agents of the invention to be formulated as tablets, including chewable tablets, pills, dragees, capsules, lozenges, hard candy, liquids, gels, syrups, slurries, powders, suspensions, elixirs, wafers, and the like, for oral ingestion by a patient to be treated. Such formulations can comprise pharmaceutically acceptable carriers including solid diluents or fillers, sterile aqueous media and various non-toxic organic solvents. A solid carrier can be one or more substances which can also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Generally, the agents of the invention will be included at concentration levels ranging from about 0.5%, about 5%, about 10%, about 20%, or about 30% to about 50%, about 60%, about 70%, about 80% or about 90% by weight of the total composition of oral dosage forms, in an amount sufficient to provide a desired unit of dosage.

Aqueous suspensions for oral use can contain agent(s) of this invention with pharmaceutically acceptable excipients, such as a suspending agent (e.g., methyl cellulose), a wetting agent (e.g., lecithin, lysolecithin and/or a long-chain fatty alcohol), as well as coloring agents, preservatives, flavoring agents, and the like.

In another aspect, oils or non-aqueous solvents can be required to bring the agents into solution, due to, for example, the presence of large lipophilic moieties. Alternatively, emulsions, suspensions, or other preparations, for example, liposomal preparations, can be used. With respect to liposomal preparations, any known methods for preparing liposomes for treatment of a condition can be used. See, for example, Bangham et al., J. Mol. Biol. 23: 238-252 (1965) and Szoka et al., Proc. Natl Acad. Sci. USA 75: 4194-4198 (1978), incorporated herein by reference. Ligands can also be attached to the liposomes to direct these compositions to particular sites of action. Agents of this invention can also be integrated into foodstuffs, e.g., cream cheese, butter, salad dressing, or ice cream to facilitate solubilization, administration, and/or compliance in certain patient populations.

Pharmaceutical preparations for oral use can be obtained as a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; flavoring elements, cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinyl pyrrolidone (PVP). If desired, disintegrating agents can be added, such as the cross-linked polyvinyl pyrrolidone, agar, or alginic acid or a salt thereof such as sodium alginate. The agents can also be formulated as a sustained release preparation.

Dragee cores can be provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active agents.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active agents can be dissolved or suspended in suitable liquids, such as fatty oils, liquid paraffin, or liquid polyethylene glycols. In addition, stabilizers can be added. All formulations for oral administration should be in dosages suitable for administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions can be prepared in solutions, for example, in aqueous propylene glycol solutions or can contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Suitable fillers or carriers with which the compositions can be administered include agar, alcohol, fats, lactose, starch, cellulose derivatives, polysaccharides, polyvinylpyrrolidone, silica, sterile saline and the like, or mixtures thereof used in suitable amounts. Solid form preparations include solutions, suspensions, and emulsions, and can contain, in addition to the active component, colorants, flavors, stabilizers, buffers, artificial and natural sweeteners, dispersants, thickeners, solubilizing agents, and the like.

A syrup or suspension can be made by adding the active compound to a concentrated, aqueous solution of a sugar, e.g., sucrose, to which can also be added any accessory ingredients. Such accessory ingredients can include flavoring, an agent to retard crystallization of the sugar or an agent to increase the solubility of any other ingredient, e.g., as a polyhydric alcohol, for example, glycerol or sorbitol.

When formulating compounds of the invention for oral administration, it can be desirable to utilize gastroretentive formulations to enhance absorption from the gastrointestinal (GI) tract. A formulation which is retained in the stomach for several hours can release compounds of the invention slowly and provide a sustained release that can be used in methods of the invention. Disclosure of such gastro-retentive formulations are found in Klausner, E. A.; Lavy, E.; Barta, M.; Cserepes, E.; Friedman, M.; Hoffman, A. 2003 "Novel gastroretentive dosage forms: evaluation of gastroretentivity and its effect on levodopa in humans." Pharm. Res. 20, 1466-73, Hoffman, A.; Stepensky, D.; Lavy, E.; Eyal, S. Klausner, E.; Friedman, M. 2004 "Pharmacokinetic and pharmacodynamic aspects of gastroretentive dosage forms" hit. J. Pharm. 11, 141-53, Streubel, A.; Siepmann, J.; Bodmeier, R.; 2006 "Gastroretentive drug delivery systems" Expert Opin. Drug Deliver. 3, 217-3, and Chavanpatil, M. D.; Jain, P.; Chaudhari, S.; Shear, R.; Vavia, P. R. "Novel sustained release, swellable and bioadhesive gastroretentive drug delivery system for olfoxacin" Int. J. Pharm. 2006 epub March 24. Expandable, floating and bioadhesive techniques can be utilized to maximize absorption of the compounds of the invention.

The compounds of the invention can be formulated for parenteral administration (e.g., by injection, for example bolus injection or continuous infusion) and can be presented in unit dose form in ampoules, pre-filled syringes, small volume infusion or in multi-dose containers with an added preservative. The compositions can take such forms as suspensions, solutions, or emulsions in oily or aqueous vehicles, for example solutions in aqueous polyethylene glycol.

For injectable formulations, the vehicle can be chosen from those known in art to be suitable, including aqueous solutions or oil suspensions, or emulsions, with sesame oil, corn oil, cottonseed oil, or peanut oil, as well as elixirs, mannitol, dextrose, or a sterile aqueous solution, and similar pharmaceutical vehicles. The formulation can also comprise polymer compositions which are biocompatible, biodegradable, such as poly(lactic-co-glycolic)acid. These materials can be made into micro or nanospheres, loaded with drug and further coated or derivatized to provide superior sustained release performance. Vehicles suitable for periocular or intraocular injection include, for example, suspensions of therapeutic agent in injection grade water, liposomes and vehicles suitable for lipophilic substances. Other vehicles for periocular or intraocular injection are well known in the art.

In a preferred aspect, the composition is formulated in accordance with routine procedures as a pharmaceutical composition adapted for intravenous administration to human beings. Typically, compositions for intravenous administration are solutions in sterile isotonic aqueous buffer. Where necessary, the composition can also include a solubilizing agent and a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients can be mixed prior to administration.

When administration is by injection, the active compound can be formulated in aqueous solutions, specifically in physiologically compatible buffers such as Hanks solution, Ringer's solution, or physiological saline buffer. The solution can contain formulatory agents such as suspending, stabilizing and/or dispersing agents. Alternatively, the active compound can be in powder form for constitution with a suitable vehicle, e.g., sterile pyrogen-free water, before use. In another aspect, the pharmaceutical composition does not comprise an adjuvant or any other substance added to enhance the immune response stimulated by the peptide. In another aspect, the pharmaceutical composition comprises a substance that inhibits an immune response to the peptide. Methods of formulation are known in the art, for example, as disclosed in Remington's Pharmaceutical Sciences, latest edition, Mack Publishing Co., Easton P.

In addition to the formulations described previously, the agents can also be formulated as a depot preparation. Such long acting formulations can be administered by implantation or transcutaneous delivery (for example subcutaneously or intramuscularly), intramuscular injection or use of a transdermal patch. Thus, for example, the agents can be formulated with suitable polymeric or hydrophobic materials (for example as an emulsion in an acceptable oil) or ion exchange resins, or as sparingly soluble derivatives, for example, as a sparingly soluble salt.

In another aspect, pharmaceutical compositions comprising one or more agents of the present invention exert local and regional effects when administered topically or injected at or near particular sites of infection. Direct topical application, e.g., of a viscous liquid, solution, suspension, dimethylsulfoxide (DMSO)-based solutions, liposomal formulations, gel, jelly, cream, lotion, ointment, suppository, foam, or aerosol spray, can be used for local administration, to produce for example local and/or regional effects. Pharmaceutically appropriate vehicles for such formulation include, for example, lower aliphatic alcohols, polyglycols (e.g., glycerol or polyethylene glycol), esters of fatty acids, oils, fats, silicones, and the like. Such preparations can also include preservatives (e.g., p-hydroxybenzoic acid esters) and/or antioxidants (e.g., ascorbic acid and tocopherol). See also Dermatological Formulations: Percutaneous absorption, Barry (Ed.), Marcel Dekker Incl, 1983. In another aspect, local/topical formulations comprising a fatty acid synthesis pathway inhibitor e.g., an inhibitor of FASN gene expression or FASN protein activity, are used to treat epidermal or mucosal viral infections.

Pharmaceutical compositions of the present invention can contain a cosmetically or dermatologically acceptable carrier. Such carriers are compatible with skin, nails, mucous membranes, tissues and/or hair, and can include any conventionally used cosmetic or dermatological carrier meeting these requirements. Such carriers can be readily selected by one of ordinary skill in the art. In formulating skin ointments, an agent or combination of agents of the instant invention can be formulated in an oleaginous hydrocarbon base, an anhydrous absorption base, a water-in-oil absorption base, an oil-in-water water-removable base and/or a water-soluble base. Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

Ointments and creams can, for example, be formulated with an aqueous or oily base with the addition of suitable thickening and/or gelling agents. Lotions can be formulated with an aqueous or oily base and will in general also containing one or more emulsifying agents, stabilizing agents, dispersing agents, suspending agents, thickening agents, or coloring agents. The construction and use of transdermal patches for the delivery of pharmaceutical agents is well known in the art. See, e.g., U.S. Pat. Nos. 5,023,252, 4,992,445 and 5,001,139. Such patches can be constructed for continuous, pulsatile, or on demand delivery of pharmaceutical agents.

Lubricants which can be used to form pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the pharmaceutical composition.

The compositions according to the present invention can be in any form suitable for topical application, including aqueous, aqueous-alcoholic or oily solutions, lotion or serum dispersions, aqueous, anhydrous or oily gels, emulsions obtained by dispersion of a fatty phase in an aqueous phase (O/W or oil in water) or, conversely, (W/O or water in oil), microemulsions or alternatively microcapsules, microparticles or lipid vesicle dispersions of ionic and/or nonionic type. These compositions can be prepared according to conventional methods. Other than the agents of the invention, the amounts of the various constituents of the compositions according to the invention are those conventionally used in the art. These compositions in particular constitute protection, treatment or care creams, milks, lotions, gels or foams for the face, for the hands, for the body and/or for the mucous membranes, or for cleansing the skin. The compositions can also consist of solid preparations constituting soaps or cleansing bars.

Compositions of the present invention can also contain adjuvants common to the cosmetic and dermatological fields, such as hydrophilic or lipophilic gelling agents, hydrophilic or lipophilic active agents, preserving agents, antioxidants, solvents, fragrances, fillers, sunscreens, odor-absorbers and dyestuffs. The amounts of these various adjuvants are those conventionally used in the fields considered and, for example, are from about 0.01% to about 20% of the total weight of the composition. Depending on their nature, these adjuvants can be introduced into the fatty phase, into the aqueous phase and/or into the lipid vesicles.

In another aspect, ocular viral infections can be effectively treated with ophthalmic solutions, suspensions, ointments or inserts comprising an agent or combination of agents of the present invention. Eye drops can be prepared by dissolving the active ingredient in a sterile aqueous solution such as physiological saline, buffering solution, etc., or by combining powder compositions to be dissolved before use. Other vehicles can be chosen, as is known in the art, including but not limited to: balance salt solution, saline solution, water soluble polyethers such as polyethyene glycol, polyvinyls, such as polyvinyl alcohol and povidone, cellulose derivatives such as methylcellulose and hydroxypropyl methylcellulose, petroleum derivatives such as mineral oil and white petrolatum, animal fats such as lanolin, polymers of acrylic acid such as carboxypolymethylene gel, vegetable fats such as peanut oil and polysaccharides such as dextrans, and glycosaminoglycans such as sodium hyaluronate. If desired, additives ordinarily used in the eye drops can be added. Such additives include isotonizing agents (e.g., sodium chloride, etc.), buffer agent (e.g., boric acid, sodium monohydrogen phosphate, sodium dihydrogen phosphate, etc.), preservatives (e.g., benzalkonium chloride, benzethonium chloride, chlorobutanol, etc.), thickeners (e.g., saccharide such as lactose, mannitol, maltose, etc.; e.g., hyaluronic acid or its salt such as sodium hyaluronate, potassium hyaluronate, etc.; e.g., mucopolysaccharide such as chondroitin sulfate, etc.; e.g., sodium polyacrylate, carboxyvinyl polymer, cross-linked polyacrylate, polyvinyl alcohol, polyvinyl pyrrolidone, methyl cellulose, hydroxy propyl methylcellulose, hydroxyethyl cellulose, carboxymethyl cellulose, hydroxy propyl cellulose or other agents known to those skilled in the art).

The solubility of the components of the present compositions can be enhanced by a surfactant or other appropriate co-solvent in the composition. Such cosolvents include polysorbate 20, 60, and 80, Pluronic F68, F-84 and P-103, cyclodextrin, or other agents known to those skilled in the art. Such co-solvents can be employed at a level of from about 0.01% to 2% by weight.

The compositions of the invention can be packaged in multidose form. Preservatives can be preferred to prevent microbial contamination during use. Suitable preservatives include: benzalkonium chloride, thimerosal, chlorobutanol, methyl paraben, propyl paraben, phenylethyl alcohol, edetate disodium, sorbic acid, Onamer M, or other agents known to those skilled in the art. In the prior art ophthalmic products, such preservatives can be employed at a level of from 0.004% to 0.02%. In the compositions of the present application the preservative, preferably benzalkonium chloride, can be employed at a level of from 0.001% to less than 0.01%, e.g. from 0.001% to 0.008%, preferably about 0.005% by weight. It has been found that a concentration of benzalkonium chloride of 0.005% can be sufficient to preserve the compositions of the present invention from microbial attack.

In another aspect, viral infections of the ear can be effectively treated with otic solutions, suspensions, ointments or inserts comprising an agent or combination of agents of the present invention.

In another aspect, the agents of the present invention are delivered in soluble rather than suspension form, which allows for more rapid and quantitative absorption to the sites of action. In general, formulations such as jellies, creams, lotions, suppositories and ointments can provide an area with more extended exposure to the agents of the present invention, while formulations in solution, e.g., sprays, provide more immediate, short-term exposure.

In another aspect relating to topical/local application, the pharmaceutical compositions can include one or more penetration enhancers. For example, the formulations can comprise suitable solid or gel phase carriers or excipients that increase penetration or help delivery of agents or combinations of agents of the invention across a permeability barrier, e.g., the skin. Many of these penetration-enhancing compounds are known in the art of topical formulation, and include, e.g., water, alcohols (e.g., terpenes like methanol, ethanol, 2-propanol), sulfoxides (e.g., dimethyl sulfoxide, decylmethyl sulfoxide, tetradecylmethyl sulfoxide), pyrrolidones (e.g., 2-pyrrolidone, N-methyl-2-pyrrolidone, N-(2-hydroxyethyl)pyrrolidone), laurocapram, acetone, dimethylacetamide, dimethylformamide, tetrahydrofurfuryl alcohol, L-α-amino acids, anionic, cationic, amphoteric or nonionic surfactants (e.g., isopropyl myristate and sodium lauryl sulfate), fatty acids, fatty alcohols (e.g., oleic acid), amines, amides, clofibric acid amides, hexamethylene lauramide, proteolytic enzymes, α-bisabolol, d-limonene, urea and N,N-diethyl-m-toluamide, and the like. Additional examples include humectants (e.g., urea), glycols (e.g., propylene glycol and polyethylene glycol), glycerol monolaurate, alkanes, alkanols, ORGELASE, calcium carbonate, calcium phosphate, various sugars, starches, cellulose derivatives, gelatin, and/or other polymers. In another aspect, the pharmaceutical compositions will include one or more such penetration enhancers.

In another aspect, the pharmaceutical compositions for local/topical application can include one or more antimicrobial preservatives such as quaternary ammonium compounds, organic mercurials, p-hydroxy benzoates, aromatic alcohols, chlorobutanol, and the like.

Gastrointestinal viral infections can be effectively treated with orally- or rectally delivered solutions, suspensions, ointments, enemas and/or suppositories comprising an agent or combination of agents of the present invention.

Respiratory viral infections can be effectively treated with aerosol solutions, suspensions or dry powders comprising an agent or combination of agents of the present invention. Administration by inhalation is particularly useful in treating viral infections of the lung, such as an HRV infection. The aerosol can be administered through the respiratory system or nasal passages. For example, one skilled in the art will recognize that a composition of the present invention can be suspended or dissolved in an appropriate carrier, e.g., a pharmaceutically acceptable propellant, and administered directly into the lungs using a nasal spray or inhalant. For example, an aerosol formulation comprising a fatty acid synthesis pathway inhibitor e.g., an inhibitor of FASN gene expression or FASN protein activity, can be dissolved, suspended or emulsified in a propellant or a mixture of solvent and propellant, e.g., for administration as a nasal spray or inhalant. Aerosol formulations can contain any acceptable propellant under pressure, such as a cosmetically or dermatologically or pharmaceutically acceptable propellant, as conventionally used in the art.

An aerosol formulation for nasal administration is generally an aqueous solution designed to be administered to the nasal passages in drops or sprays. Nasal solutions can be similar to nasal secretions in that they are generally isotonic and slightly buffered to maintain a pH of about 5.5 to about 6.5, although pH values outside of this range can additionally be used. Antimicrobial agents or preservatives can also be included in the formulation.

An aerosol formulation for inhalations and inhalants can be designed so that the agent or combination of agents of the present invention is carried into the respiratory tree of the subject when administered by the nasal or oral respiratory route. Inhalation solutions can be administered, for example, by a nebulizer. Inhalations or insufflations, comprising finely powdered or liquid drugs, can be delivered to the respiratory system as a pharmaceutical aerosol of a solution or suspension of the agent or combination of agents in a propellant, e.g., to aid in disbursement. Propellants can be liquefied gases, including halocarbons, for example, fluorocarbons such as fluorinated chlorinated hydrocarbons, hydrochlorofluorocarbons, and hydrochlorocarbons, as well as hydrocarbons and hydrocarbon ethers.

Halocarbon propellants useful in the present invention include fluorocarbon propellants in which all hydrogens are replaced with fluorine, chlorofluorocarbon propellants in which all hydrogens are replaced with chlorine and at least one fluorine, hydrogen-containing fluorocarbon propellants, and hydrogen-containing chlorofluorocarbon propellants. Halocarbon propellants are described in Johnson, U.S. Pat. No. 5,376,359, issued Dec. 27, 1994; Byron et al., U.S. Pat. No. 5,190,029, issued Mar. 2, 1993; and Purewal et al., U.S. Pat. No. 5,776,434, issued Jul. 7, 1998. Hydrocarbon propellants useful in the invention include, for example, propane, isobutane, n-butane, pentane, isopentane and neopentane. A blend of hydrocarbons can also be used as a propellant. Ether propellants include, for example, dimethyl ether as well as the ethers. An aerosol formulation of the invention can also comprise more than one propellant. For example, the aerosol formulation can comprise more than one propellant from the same class, such as two or more fluorocarbons; or more than one, more than two, more than three propellants from different classes, such as a fluorohydrocarbon and a hydrocarbon. Pharmaceutical compositions of the present invention can also be dispensed with a compressed gas, e.g., an inert gas such as carbon dioxide, nitrous oxide or nitrogen.

Aerosol formulations can also include other components, for example, ethanol, isopropanol, propylene glycol, as well as surfactants or other components such as oils and detergents. These components can serve to stabilize the formulation and/or lubricate valve components.

The aerosol formulation can be packaged under pressure and can be formulated as an aerosol using solutions, suspensions, emulsions, powders and semisolid preparations. For example, a solution aerosol formulation can comprise a solution of an agent of the invention such as a fatty acid synthesis pathway inhibitor e.g., an inhibitor of FASN gene expression or FASN protein activity, in (substantially) pure propellant or as a mixture of propellant and solvent. The solvent can be used to dissolve the agent and/or retard the evaporation of the propellant. Solvents useful in the invention include, for example, water, ethanol and glycols. Any combination of suitable solvents can be use, optionally combined with preservatives, antioxidants, and/or other aerosol components.

An aerosol formulation can also be a dispersion or suspension. A suspension aerosol formulation can comprise a suspension of an agent or combination of agents of the instant invention, e.g., a fatty acid synthesis pathway inhibitor, e.g., an inhibitor of FASN gene expression or FASN protein activity, and a dispersing agent. Dispersing agents useful in the invention include, for example, sorbitan trioleate, oleyl alcohol, oleic acid, lecithin and corn oil. A suspension aerosol formulation can also include lubricants, preservatives, antioxidant, and/or other aerosol components.

An aerosol formulation can similarly be formulated as an emulsion. An emulsion aerosol formulation can include, for example, an alcohol such as ethanol, a surfactant, water and a propellant, as well as an agent or combination of agents of the invention, e.g., a fatty acid synthesis pathway, e.g., an inhibitor of FASN gene expression or FASN protein activity. The surfactant used can be nonionic, anionic or cationic. One example of an emulsion aerosol formulation comprises, for example, ethanol, surfactant, water and propellant. Another example of an emulsion aerosol formulation comprises, for example, vegetable oil, glyceryl monostearate and propane.

The compounds of the invention can be formulated for administration as suppositories. A low melting wax, such as a mixture of triglycerides, fatty acid glycerides, Witepsol S55 (trademark of Dynamite Nobel Chemical, Germany), or cocoa butter is first melted and the active component is dispersed homogeneously, for example, by stirring. The molten homogeneous mixture is then poured into convenient sized molds, allowed to cool, and to solidify.

The compounds of the invention can be formulated for vaginal administration. Pessaries, tampons, creams, gels, pastes, foams or sprays containing in addition to the active ingredient such carriers as are known in the art to be appropriate.

It is envisioned additionally, that the compounds of the invention can be attached releasably to biocompatible polymers for use in sustained release formulations on, in or attached to inserts for topical, intraocular, periocular, or systemic administration. The controlled release from a biocompatible polymer can be utilized with a water soluble polymer to form a instillable formulation, as well. The controlled release from a biocompatible polymer, such as for example, PLGA microspheres or nanospheres, can be utilized in a formulation suitable for intra ocular implantation or injection for sustained release administration, as well. Any suitable biodegradable and biocompatible polymer can be used.

Pharmaceutical compositions suitable for use in the present invention include compositions wherein the active ingredients are present in an effective amount, i.e., in an amount effective to achieve therapeutic and/or prophylactic benefit in a host with at least one viral infection or in a subject having cancer. The actual amount effective for a particular application will depend on the condition or conditions being treated, the condition of the subject, the formulation, and the route of administration, as well as other factors known to those of skill in the art. Determination of an effective amount of a fatty acid synthesis pathway inhibitor e.g., an inhibitor of FASN gene expression or FASN protein activity, is well within the capabilities of those skilled in the art, in light of the disclosure herein, and will be determined using routine optimization techniques.

The effective amount for use in humans can be determined from animal models. For example, a dose for humans can be formulated to achieve circulating, liver, topical and/or gastrointestinal concentrations that have been found to be effective in animals. One skilled in the art can determine the effective amount for human use, especially in light of the animal model experimental data described herein. Based on animal data, and other types of similar data, those skilled in the art can determine the effective amounts of compositions of the present invention appropriate for humans.

The effective amount when referring to an agent or combination of agents of the invention will generally mean the dose ranges, modes of administration, formulations, etc., that have been recommended or approved by any of the various regulatory or advisory organizations in the medical or pharmaceutical arts (e.g., FDA, AMA) or by the manufacturer or supplier.

Further, appropriate doses for a fatty acid synthesis pathway inhibitor e.g., an inhibitor of FASN gene expression or FASN protein activity, can be determined based on in vitro experimental results. For example, the in vitro potency of an agent in inhibiting a fatty acid synthesis pathway component, e.g., FASN gene expression or FASN protein activity, provides information useful in the development of effective in vivo dosages to achieve similar biological effects.

In another aspect, administration of agents of the present invention can be intermittent, for example administration once every two days, every three days, every five days, once a week, once or twice a month, and the like. In another aspect, the amount, forms, and/or amounts of the different forms can be varied at different times of administration.

A person of skill in the art would be able to monitor in a patient the effect of administration of a particular agent. For example, HIV viral load levels can be determined by techniques standard in the art, such as measuring CD4 cell counts, and/or viral levels as detected by PCR. Other techniques would be apparent to one of skill in the art.

Having now generally described various aspects and aspects of the invention, the same will be more readily understood through reference to the following examples which are provided by way of illustration, and are not intended to be limiting, unless specified.

Example 1

FASN Inhibition by Compounds of the Present Disclosure

Determination of FASN biochemical activity: The FASN enzyme was isolated from SKBr3 cells. SKBr3 is a human breast cancer cell-line with high levels of FASN expression. It is estimated that FASN comprises about 25% of the cytosolic proteins in this cell line. SKBr3 cells were homogenized in a dounce homogenizer then centrifuged for 15 minutes at 4° C. to remove particulate matter. The supernatant was then analyzed for protein content, diluted to the appropriate concentration, and used to measure FASN activity. The presence of FASN was confirmed by western blot analysis. A similar method for isolation of FASN from SKBr3 cells is described in Teresa, P. et al. (*Clin. Cancer Res.* 2009; 15(24), 7608-7615).

FASN activity of the SKBr3 cell extract was determined by measuring either NADPH oxidation or the amount of thiol-containing coenzyme A (CoA) released during the fatty acid synthase reaction. The dye CPM (7-diethylamino-3-(4'-maleimidyl-phenyl)-4-methylcoumarin) contains a thiol reactive group that increases its fluorescence emission on reaction with the sulfhydryl group of CoA. The biochemical activities shown in Table 1 were determined using the fluorescence measurement of CoA release via a procedure described in Chung C. C. et al. (*Assay and Drug Development Technologies,* 2008, 6(3), 361-374).

Example 2

Antiviral Activity

The antiviral activity of Structure (I-Z) was assessed using the HCV1b replicon system:

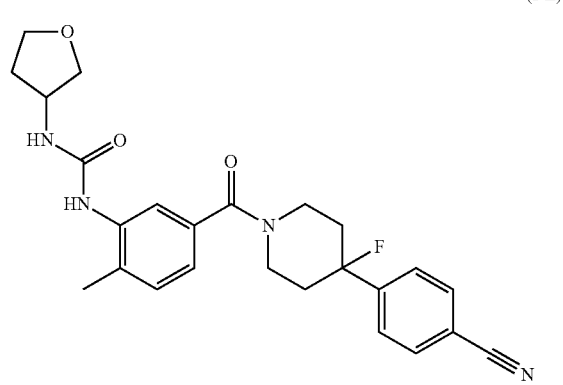

(I-Z)

The replicon was constructed using the ET (luc-ubi-neo/ET) cell line, a Huh7 human hepatoma cell line harboring an HCV replicon with a stable luciferase (Luc) reporter and three cell culture-adaptive mutations (Pietschmann, et al (2002) J. Virol. 76:4008-4021). The HCV replicon antiviral evaluation assay examined the effects of compounds at six half-log concentrations. Human interferon alpha-2b was included in each run as a positive control compound. Sub-confluent cultures of the ET line were plated out into 96-well plates that are dedicated for the analysis of cell numbers (cytotoxicity) or antiviral activity and the next day drugs were added to the appropriate wells. Cells were processed 72 hr later when the cells were still sub-confluent. $EC_{50}$ (concentrations inhibiting the replicon by 50% and 90%, respectively), $IC_{50}$ (concentration decreasing cell viability by 50%) and SI (selective index: $IC_{50}/EC_{50}$) values were determined. HCV RNA replicon levels were assessed as either HCV RNA replicon-derived Luc activity or as HCV RNA by TaqMan RT-PCR. Two methods were used to estimate cell counts (cytotoxicity). When the Luc assay system was employed, the colorimetric CytoTox-1 cell proliferation assay (Promega) was used to estimate cell numbers, while ribosomal RNA (rRNA) levels determined via TaqMan RT-PCR were used as an indication of cell numbers in the RNA-based assay. A summary of the results is listed below in Table 2.

TABLE 2

| Method | Replicon EC50 (µM) | Cell IC50 (µM) | Selectivity Index |
|---|---|---|---|
| Luciferase activity | 0.017 | >32 | >1882 |
| TaqMan RT-PCR | 0.105 | >100 | >952 |

Example 3

FASN Inhibition Correlates to HCV Inhibition

The antiviral activities of 15 compounds of the present disclosure (numbers correlate to the compounds in Table 1) were measured using the HCV replicon system. Replicon cell line 1b (HCV 1b/Luc-Neo replicon (1b Con1 with Firefly gene integrated)) was established following published methods (Lohmann et al. (1999) Science 285(5424): 110-113, Lohmann et al. (2001) J. Virol. 75(3):1437-1449 and Qi et al. (2009) Antiviral Res. 81(2):166-173) using Huh7 by G418 selection. The replicon was assembled using synthetic gene fragments. The GT1b line has PV-EKT and harbors 3 adaptive mutations E1202G(NS3), T1280I(NS3), K1846T(NS4B) and the backbone is Con1. The culture medium was:
  a) DMEM supplement with 10% FBS, G418 (250 µg/ml), streptomycin (100 µg/ml)/penicillin (100 U/ml), L-glutamine (100×), NEAA (100×)
  b) Media prepared as follows:
    i) 500 ml DMEM media (Gibco, Cat#11960-077)
    ii) 57 ml Fetal Bovine Serum (Gibco, Cat#16140-071)
    iii) 5.7 ml Penicillin-Streptomycin (Gibco, Cat#15140-122)
    iv) 5.7 ml MEM non-essential amino acids (Gibco, Cat#111140-050)
    v) 5.7 ml L-glutamine (Gibco, Cat#125030-081)
    vi) 574.1 ml media+2.87 ml 50 mg/ml G418 [final 0.25 mg/ml] (Gibco, Cat#10131-027)

Compounds were dissolved in DMSO to provide a 10 mM stock or used from stock DMSO solutions. Compounds were diluted to generate 10-point half log (3.16-fold) serial dilutions for assay in 384-well plates (Echo qualified 384-well PP (Labcyte Cat#P-05525)) plus DMSO in duplicate. This experiment was repeated three times on three different days.

Cells were harvested when confluency reached 90%400%. Cell concentrations were adjusted to $8 \times 10^4$ cells/ml and added to 384-well white assay microplates (tissue-culture treated—Greiner Cat#781080) to reach a final cell density of 2,000 cells/well. Plates were incubated at 5% $CO_2$ and 37° C. for 72 hours.

After 72 hours of incubation Bright-Glo Luciferase reagent (Promega, cat# E2650) and Cell Titer Flo (Promega, cat#G6080/1/2) were prepared and stored in the dark while equilibrating to room temperature. Treated cells were likewise equilibrated to room temperature. 10 µL of Cell Titer Flo was added to each well of compound-treated cells and incubated in microtiter plates for approx. 0.5 hours. Cell viability was measured using an Envision reader (available from Perkin Elmer) to estimate cytotoxicity. 30 µL of firefly luciferase substrate were added to each well and chemiluminescence was measured as an indicator of the extent of HCV replication.

The anti-replicon activity (% inhibition) is calculated using the equation:

$$\% \text{ Inhibition} = \left(1 - \frac{Cmpd - \text{Control}}{DMSO - \text{Control}}\right) \times 100.$$

Cytotoxicity is calculated using the equation:

$$\% \text{ Cytotoxicity} = \left(1 - \frac{Cmpd - \text{Background}}{DMSO - \text{Background}}\right) \times 100.$$

There was determined to be a correlation between potency of FASN inhibition and antiviral activity as illustrated in Table 3 below and FIG. 1. It is noted that none of the compounds caused significant cytotoxicity.

TABLE 3

| Molecule | Biochemical IC50 (µM) | Antiviral EC50 (µM) |
|---|---|---|
| 1 | 0.230 | 0.425 |
| 2 | 0.065 | 0.192 |
| 12 | 0.370 | 1.003 |
| 14 | 0.263 | 0.260 |
| 20 | 0.022 | 0.011 |
| 27 | 0.107 | 0.153 |
| 43 | 0.110 | 0.154 |
| 55 | 0.035 | 0.034 |
| 58 | 0.025 | 0.078 |
| 67 | 0.090 | 0.270 |
| 68 | 0.100 | 0.301 |
| 70 | 0.037 | 0.099 |
| 73 | 0.040 | 0.117 |
| 152 | 0.052 | 0.072 |
| 343 | 0.600 | 0.624 |

Example 4

FASN Inhibitors Retain Activity Against HCV Mutants that Confer Resistance to Direct-Acting Antiviral Agents One of the major challenges in treating hepatitis C is the rapid emergence of resistance in response to direct-acting antiviral agents. Resistance typically results when the virus generates a point mutant that supports essential viral functions but prevents antiviral agents from binding Three FASN inhibitors (compounds 55, 20, and 70) were tested for their ability to inhibit mutants of HCV that confer resistance to representative antiviral agents. Each of these mutants was introduced into a GT1b construct based on a Con1 backbone containing the PVIRES-Luciferase Ubi-Neo gene and harboring 1 adaptive mutation (S2204I). (Lohmann et al. (1999) *Science* 285(5424):110-113, Lohmann et al. (2001) *J. Virol.* 75(3):1437-1449 and Qi et al. (2009) *Antiviral Res.* 81(2): 166-173). Antiviral activities were measured by the method described in Example 3.

The studied mutations are shown in Table 4 below.

TABLE 4

Studied Mutations

| Mutant | Reference |
|---|---|
| NS3 A156T | Susser et al *J. Clin. Virol.* 52(4), 321-327 (2011) and references therein |
| NS3 R155K | Susser et al *J. Clin. Virol.* 52(4), 321-327 (2011) and references therein |
| NS4B H94R | Rai et al. *Antiviral Res.* 90, 93-101 (2011) |
| NS5AY393H | Fridell et a.l *Antimicrob. Agents Chemother.* 54(9), 3641-3650 (2010) |
| NS5B M423I | (non-nucleoside site) Troke et al. *Antimicrob. Agents Chemother.* 56(3), 1331-1341 (2012) |
| NS5B S282T | (nucleoside site) Dutartre et al. *Antimicrob. Agents Chemother.* 50(12), 4161-4169 (2006) |

A known NS4B allosteric inhibitor (Compound A), a known NS5A inhibitor (Compound B), a known non-nucleoside NS5B inhibitor (Compound C), a known NS3/NS4A protease inhibitor (Compound D) and a known nucleoside NS5B inhibitor (Compound E) were tested in parallel with the FASN inhibitors of the present disclosure to confirm the performance of the resistance mutations.

Antiviral $EC_{50}$'s for the various compounds against the panel of mutants, along with the relative shift in $EC_{50}$ relative to the GT1b wild-type replicon are shown below. Normal assay variation is ±3-4 fold. $EC_{50}$ shifts outside this range imply resistance and are indicated in bold. The 3 FASN inhibitors retain activity across the panel of mutants, whereas the direct-acting antiviral agents display resistance against mutations in their respective binding sites.

TABLE 5

Antiviral $EC_{50}$'s.

| Compound | $EC_{50}$ (nM) | | | | | | |
|---|---|---|---|---|---|---|---|
| | 1b Wild Type | NS3 A156T | NS3 R155K | NS4B H94R | NS5A Y93H | NS5B M423I | NS5B S282T |
| 55 | 49.63 | 143.00 | 156.10 | 67.31 | 109.40 | 19.22 | 73.30 |
| 20 | 16.71 | 44.06 | 25.46 | 17.02 | 32.00 | 19.70 | 25.60 |
| 70 | 39.18 | 49.97 | 43.91 | 36.00 | 108.90 | 58.69 | 56.90 |
| Compound A | 261.00 | 232.20 | 209.60 | 2813.00 | n.t. | 126.60 | n.t. |
| Compound B | 0.01 | 0.01 | n.t. | n.t. | 0.28 | 0.01 | 0.01 |
| Compound D | 0.67 | 105.00 | 236.60 | 0.39 | n.t. | 1.54 | n.t. |
| Compound C | 4.27 | 4.57 | 8.43 | 4.61 | 3.00 | 34.09 | 3.00 |
| Compound E | 583.70 | 890.90 | n.t. | n.t. | 1069.0 | 159.30 | 15650.0 |

TABLE 6

Fold shift in EC50 relative to wild-type

| Compound | HCV Binding Site | NS3 A156T | NS3 R155K | NS4B H94R | NS5A Y93H | NS5B M423I | NS5B S282T |
|---|---|---|---|---|---|---|---|
| 55 | | 2.88 | 3.15 | 1.36 | 2.20 | 0.39 | 1.48 |
| 20 | | 2.64 | 1.52 | 1.02 | 1.92 | 1.18 | 1.53 |
| 70 | | 1.28 | 1.12 | 0.92 | 2.78 | 1.50 | 1.45 |
| Compound A | NS4B | 0.89 | 0.80 | 10.78 | n.t. | 0.49 | n.t. |
| Compound B | NS5A | 1.00 | n.t. | n.t. | 35.13 | 0.75 | 0.88 |
| Compound D | NS3/4A | 156.46 | 352.56 | 0.58 | n.t. | 2.29 | n.t. |
| Compound C | NS5B (non-nuc) | 1.07 | 1.98 | 1.08 | 0.70 | 7.99 | 0.70 |
| Compound E | NS5B (nuc) | 1.53 | n.t. | n.t. | 1.83 | 0.27 | 26.81 |

Example 5

FASN Inhibitors Useful in Combination Therapies

This example describes the in vitro antiviral activity and cytotoxicity of the compound of Structure (V-K) in combination with IFN-α, Ribavirin, Compounds B, C, D and E against an HCV GT1b replicon cell line.

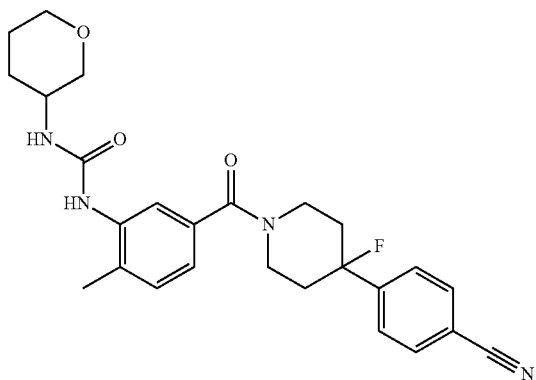

(V-K)

Materials:
Virus:
The GT1b replicon plasmid was assembled using synthetic gene fragments. The replicon genome contains PVI-RES-Luciferase Ubi-Neo gene segments and harbors 1 adaptive mutation (S22041), and the backbone is Con1. The replicon GT1b cell line was established by the following published methods.

Medium and Reagents:
Table 7 below provides details regarding the culture medium reagents used in this example.

TABLE 7

List of culture medium regents

| Reagent | Vendor | Catalogue Number |
|---|---|---|
| Dimethyl sulfoxide (DMSO) | Sigma | Cat #34869-100ML |
| DMEM | Invitrogen | Cat #11960-044 |
| Fetal Bovine Serum (FBS) | Gibco | Cat #16140 |
| Pen-Strep | Invitrogen | Cat #15140-122 |
| MEM non-essential amino acids | Invitrogen | Cat #11140-050 |
| L-Glutamin | Invitrogen | Cat #25030-081 |
| G418 (geneticin) | Gibco | Cat #10131-027 |
| Trypsin/EDTA | Invitrogen | Cat #25200-072 |
| DPBS/Modified | Hyclone | SH30028.01B |
| 96-well cell plate | Greiner | Cat #655090 |
| Cell titer fluro | Promega | Cat #G6082 |
| Bright-Glo | Promega | Cat #E264B |

Analytical Instruments:
The following analytical instruments were used to perform the assays of this example:
POD-810
Topcount (PE)
Envision (PE)
Multidrop (Thermo)

Methods:
Preparation of Compound Plates for Single Compound Testing:
Compounds were supplied as dry powders and were reconstituted in DMSO to generate stock solutions. The POD-810 system was used to generate 10-point half log (3.16-fold) serial dilutions for the assay in 96-well plates. The highest test concentrations are detailed for each compound in Table 8.

Assay Protocol (Single Compounds):
Each compound was assayed with 3.16-fold (half log) serial dilutions for 10 concentrations plus DMSO in duplicate. HCV replicon GT1b cells were harvested and adjusted to a cell concentration of 8E+04 cells/ml. A Multidrop was used to plate 100 µL/well into 96 assay microplates to reach a final cell density of 8,000 cells/well. Plates were incubated at 5% $CO_2$, 37° C. for 72 hours.

At the end of the 72 hour incubation, antiviral activity and cytotoxicity were measured. Bright-Glo Luiferase reagent and Cell Titer Flo were prepared and stored in dark while equilibrating to room temperature. The cell plates were allowed to equilibrate to room temperature as well. A Multidrop was used to add 20 µL Cell Titer Flo to each well of compound-treated and compound-free cells. The plates are incubated for 1 hour, and cell viability is measured on an Envision reader for cytoxicity calculation. Fifty microliters of firefly luciferase substrate are added to each well, incubated for 2 minutes, and chemiluminescence is measured for $EC_{50}$ calculation.

The anti-replicon activity (% inhibition) was calculated using the following equation:

% Inhibition=[1−((Compound−background)/(DMSO−background))×100].

Test Compounds and Assay Setup for Two-Compound Combination Studies:
The DMSO stocks of the compounds used in the single compound testing were also used in this analysis. Combination dilution matrixes were generated by POD-810 in 96-well assay microplates. The POD-810 system was used to generate 7-point, 2-fold serial dilutions in a matrix format. The maximum concentration tested for each compound is detailed below.

TABLE 8

Expected activities and upper concentrations of compounds tested in single-agent and combination studies

| Compound | Expected GT1b EC50 (µM) | Highest concentration for single-agent testing (µM) | Highest concentration for combination testing (µM) |
|---|---|---|---|
| (V-K) | 0.060 | 10.0 | 0.100 |
| Compound D | 0.0014 | 0.032 | 0.0032 |
| Compound C | 0.018 | 10.0 | 0.032 |
| Compound B | 0.000009 | 0.001 | 0.000032 |
| Compound E | 4.030 | 100.0 | 10.0 |
| IFN | 64.94 IU/ml | 1000 IU/ml | 10.0 IU/ml |
| Ribavirin | 26.830 | 320.0 | 100.0 |

The compound of Structure (V-K) was tested alone and in combination with compounds detailed in Table 9. Each compound was also tested alone as a single agent.

TABLE 9

Combinations of compounds for in vitro evaluation.

| Regimen | Combination |
|---|---|
| 1 | (V-K) + Compound D |
| 2 | (V-K) + Compound C |
| 3 | (V-K) + Compound B |
| 5 | (V-K) + Compound E |
| 6 | (V-K) + IFN-α |
| 7 | (V-K) + RBV |

Assay Setup (Two-Drug Combinations):

Each compound was assayed with 2-fold serial dilutions for 7 concentrations in matrix format plus each drug alone. HCV replicon GT1b cells were harvested and adjusted to a cell concentration of 8E+04 cells/ml. A Multidrop was used to plate 100 μL into 96 assay microplates to reach a final cell density of 8,000 cells/well. Plates were incubated at 5% $CO_2$, 37° C. for 72 hours.

At the end of the 72 hour incubation, antiviral activity and cytotoxicity were measured. Bright-Glo Luiferase reagent and Cell Titer Flo were prepared and store in dark while allowing to equilibrate to room temperature. The cells plates were allowed to equilibrate to room temperature as well. A Multidrop was used to add 20 μL Cell Titer Flo to each well of compound-treated and compound-free cells. The plates were incubated for 1 hour, and cell viability was measured on an Envision reader for cytotoxicity calculation. The liquid was then removed from the plates, after which 50 μL PBS and 50 μL firefly luciferase substrate solution were added to each well, after a 2-minute incubation period, chemiluminescence (for HCV replication calculation) was measured. The data were analyzed using MacSynergy™ II.

Assay Results:

Activity and Cytotoxicity of the Compounds.

The $EC_{50}$ and $CC_{50}$ values are summarized below in Table 10.

TABLE 10

$EC_{50}$ and $CC_{50}$ of Each Test Compound

| | GT1b | | |
|---|---|---|---|
| Compound | $EC_{50}$ (μM) | Expected $EC_{50}$ (μM) | $CC_{50}$ (μM) |
| (V-K) | 0.04 | 0.06 | >10 |
| Compound D | 0.0021 | 0.0014 | >0.032 |
| Compound C | 0.006 | 0.018 | >10 |
| Compound B | 0.000012 | 0.000009 | >0.001 |
| Compound E | 2.41 | 4.03 | >100 |
| IFN-α (IU/mL) | 1.34 | 1 | >1000 |
| RBV | 32.75 | 26.83 | 239 |

Combination Effect.

The combination effect of the compound pairs was calculated using MacSynergy™ II and those results are summarized in Table 11 below.

TABLE 11

Summary of the combination effects of the compound pairs

| Compd 1 (top conc) | Compd 2 (top conc) | MacSynergy ™ II SYNERGY PLOT (95%) | | | |
|---|---|---|---|---|---|
| | | SYNERGY | Log volume | ANTAGONISM | Log volume |
| (V-K) | Compound D | 16.7 | 1.51 | −13.03 | −1.18 |
| | Compound C | 2.93 | 0.27 | −9.2 | −0.83 |
| | Compound B | 6.75 | 0.61 | −7.11 | −0.64 |
| | Compound E | 1.08 | 0.1 | −7.81 | −0.73 |
| | IFN-α | 5.44 | 0.49 | −24.88 | −2.25 |
| | RBV | 1.64 | 0.15 | −3.52 | −0.32 |

\* None of the combinations cause cytotoxicity.

Conclusions

The Z factors of the compound pairs summarized in Table 12 indicate that the assay quality is better than the QC standard.

TABLE 12

Summary of the Z factor of compound pairs

| | Z factor | | |
|---|---|---|---|
| Drug Pairs | Plate-1 | Plate-2 | Plate-3 |
| (V-K) + Compound D | 0.68 | 0.86 | 0.83 |
| (V-K) + Compound C | 0.66 | 0.78 | 0.65 |
| (V-K) + Compound B | 0.70 | 0.83 | 0.84 |
| (V-K) + Compound E | 0.72 | 0.76 | 0.74 |
| (V-K) + IFN-α | 0.75 | 0.70 | 0.66 |
| (V-K) + RBV | 0.78 | 0.78 | 0.72 |

The $EC_{50}$ values of the individual compounds in the combination matrix (summarized in Table 13) are consistent with the $EC_{50}$ data in obtained for single-compound inhibition Table 10.

TABLE 13

Summary of $EC_{50}$ of single dose in compound combination

| | GT1b | |
|---|---|---|
| Compound | $EC_{50}$ (μM) in dose ranging assay | $EC_{50}$ (μM) of single dose in drug combination |
| (V-K) | 0.04 | 0.07 |
| Compound D | 0.0021 | 0.0017 |
| Compound C | 0.006 | 0.009 |
| Compound B | 0.000012 | 0.000009 |
| Compound E | 2.41 | 1.79 |
| IFN-α (IU/mL) | 1.34 | 3.43 |
| RBV | 32.75 | 31.63 |

The compound of Structure (V-K) was demonstrated to have additive antiviral activity without enhanced cytotoxicity in combination with agents representing a variety of mechanisms. These results are summarized in Table 14 below.

TABLE 14

Summary of antiviral mechanisms that are additive with the compound of Structure (V-K). The term "direct-acting antiviral" ("DAA") refers to a compound that binds to and inhibits a viral protein, rather than a host protein.

| Molecule | Mechanism | Class |
|---|---|---|
| IFN-α | Cellular defense | Host |
| RBV | Multiple | Host |
| Compound D | HCV Protease | DAA |
| Compound B | NS5A Inhibitor | DAA |
| Compound C | NS5B Inhibitor | DAA |
| Compound E | NS5B Inhibitor | DAA |

IFN-α and RBV represent current standard-of-care for treating Hepatitis C infection, and the HCV protease inhibitors Telaprevir and Boceprivir have recently been approved. The additive antiviral activity and lack of enhanced cytotoxicity in combination with IFN-α and RBV further suggest that compounds of this invention will not interfere with critical host processes such as cellular defense (IFN-α) or guanidine nucleotide biosynthesis (RBV). Compounds of this invention such as the compound of Structure (V-K) should therefore be therapeutically useful if administered in combination regimens with current standard of care. Moreover, the additive antiviral activities observed with Compound B, Compound C, and Compound E suggest that molecules of this invention such as the compound of Structure (V-K) can be productively combined with agents currently in development that target newer mechanisms (e.g., NS5A and NS5B inhibitors).

Example 6

Anti-Tumor Activity—Multiplexed Cytotoxicity Assay

Cells were grown in RPMI1640, 10% FBS, 2 mM L-alanyl-L-Glutamine, 1 mM Na pyruvate or a special medium in a humidified atmosphere of 5% $CO_2$ at 37° C. Cells were seeded into 384-well plates and incubated in a humidified atmosphere of 5% $CO_2$ at 37° C. Compounds were added 24 hours post cell seeding. At the same time, a time zero untreated cell plate was generated.

After a 72 hour incubation period, cells were fixed and stained with fluorescently labeled antibodies and nuclear dye to allow visualization of nuclei, apoptotic cells and mitotic cells. Apoptotic cells were detected using an anti-active caspase-3 antibody. Mitotic cells were detected using an anti phospho-histone-3 antibody.

Compounds were serially diluted in half-log (3.16-fold) increments and assayed over 10 concentrations in a final assay concentration of 0.1% DMSO from the highest test concentration specified in the sample information chapter. Automated fluorescence microscopy was carried out using a GE Healthcare IN Cell Analyzer 1000, and images were collected with a 4× objective.

Twelve bit tiff images were acquired using the InCell Analyzer 1000 3.2 and analyzed with Developer Toolbox 1.6 software. $EC_{50}$ and $IC_{50}$ values were calculated using non-linear regression to fit data to a sigmoidal 4 point, 4 parameter One-Site dose response model, where: y (fit)=A+[(B−A)/(1+((C/x)^D))]. Curve-fitting, $EC_{50}$/$IC_{50}$ calculations and report generation are performed using a custom data reduction engine MathIQ based software (AIM).

The multiplexed cytotoxicity assay uses a cell image based analysis technique where cells are fixed and stained with fluorescently labeled antibodies and nuclear dye to visualize nuclei, and apoptotic and mitotic cells. Apoptotic cells are detected using an anti-active caspase-3 antibody. Mitotic cells are detected using an anti phospho-histone-3 antibody.

Cell proliferation is measured by the signal intensity of the incorporated nuclear dye. The cell proliferation assay output is referred to as the relative cell count. To determine the cell proliferation end point, the cell proliferation data output is transformed to percent of control (POC) using the following formula:

POC=relative cell count(compound wells)/relative cell count(vehicle wells)×100

Time zero non-treated plate is used to determine number of doublings in 72 hour assay period: Number of doublings in 72 hours=LN[Cell number (72 hrs end point)*Cell number (time zero)]/LN(2). The output of each biomarker is fold increase over vehicle background normalized to the relative cell count in each well.

The activated caspase-3 marker labels cells from early to late stage apoptosis. The output is shown as a fold increase of apoptotic cells over vehicle background normalized to the relative cell count in each well. Concentrations of test compound that cause a 5-fold induction in the caspase-3 signal indicates significant apoptosis induction. Wells with concentrations higher than the relative cell count $IC_{95}$ are eliminated from the caspase3 induction analysis.

The phospho-histone-3 marker labels mitotic cells. The output is shown as a fold induction of mitotic cells over vehicle background normalized to the relative cell count in each well. When the fold induction of mitotic cell signal over background is ~1, there is "no effect" on the cell cycle. Two or more fold increase in phospho-histone-3 signal over vehicle background indicates significant test compound induction of mitotic block.

Two or more fold decrease in the phospho-histone-3 signal may indicate G1/S block only when cytotoxicity levels are below the measured relative cell count $IC_{95}$. When 2 or more fold decrease in the phospho-histone-3 signal are observed at concentrations higher than the relative cell count $IC_{95}$, the decrease in mitotic cell counts are most likely due to a more general cytotoxicity effect rather than a true G1/S phase block. Wells with concentrations higher than the relative cell count $IC_{95}$ are eliminated from the phospho-histone-3 analysis.

Cell proliferation measured by relative cell counts were the criteria for positive response.

Apoptosis:
>5-fold increase in activated caspase-3 signal indicates an apoptotic response Mitosis:
>2-fold increase in phospho-histone-3 indicates mitotic block
<2-fold decrease in phospho-histone-3 indicates G1/S block

TABLE 15

Results

| Compound | Biochemical $IC_{50}$ (µM) | G1/S cell cycle block (µM) | Max G2/M cell cycle block | Max Apoptosis Fold Induction |
|---|---|---|---|---|
| 205 | 0.220 | 0.160 | 1.36 | 2.39 |
| 95 | 0.030 | 0.012 | 0.94 | 2.45 |
| 142 | 0.140 | 0.031 | 1.28 | 2.34 |
| 153 | 0.060 | 0.014 | 1.17 | 2.55 |
| 427 | 0.080 | 0.019 | 1.00 | 2.39 |
| 42 | 0.070 | 0.013 | 1.09 | 2.20 |
| 48 | 0.170 | 0.027 | 1.27 | 2.20 |
| 156 | 0.030 | 0.031 | 1.28 | 2.59 |

TABLE 15-continued

| Compound | Biochemical IC$_{50}$ (μM) | G1/S cell cycle block (μM) | Max G2/M cell cycle block | Max Apoptosis Fold Induction |
|---|---|---|---|---|
| 182 | 0.150 | 0.030 | 1.54 | 2.07 |
| 183 | 0.170 | 0.031 | 1.00 | 2.40 |

While preferred aspects of the present invention have been shown and described herein, it will be obvious to those skilled in the art that such aspects are provided by way of example only. Numerous variations, changes, and substitutions will now occur to those skilled in the art without departing from the invention. It should be understood that various alternatives to the aspects of the invention described herein can be employed in practicing the invention. It is intended that the following claims define the scope of the invention and that methods and structures within the scope of these claims and their equivalents be covered thereby.

All publications and patent applications cited in this specification are herein incorporated by reference as if each individual publication or patent application were specifically and individually indicated to be incorporated by reference.

The invention claimed is:

1. A compound of the Formula (X):

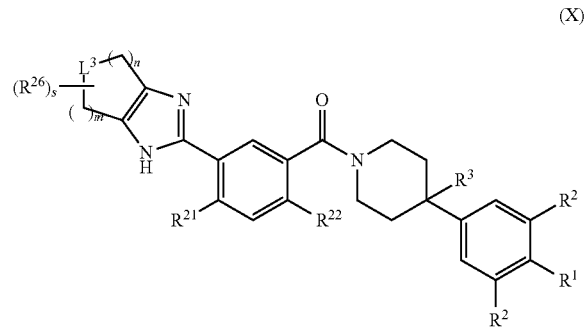

(X)

or a pharmaceutically acceptable salt thereof, wherein:

$R^1$ is H, —CN, halogen, $C_1$-$C_4$ straight or branched alkyl, —O—($C_3$-$C_5$ cycloalkyl), —O—($C_1$-$C_4$ straight or branched alkyl) wherein:
  the $C_3$-$C_5$ cycloalkyl optionally includes an oxygen or nitrogen heteroatom; and
  when $R^1$ is not H, —CN or halogen, it is optionally substituted with one or more halogens;

each $R^2$ is independently hydrogen, halogen or $C_1$-$C_4$ straight or branched alkyl;

$R^3$ is H, —OH or halogen;

$L^3$ is $C(R^{60})_2$, O or $NR^{50}$;

each $R^{60}$ is independently H, —OH, —CN, —O$_t$—($C_3$-$C_5$ cycloalkyl), —O—($C_1$-$C_4$ straight or branched alkyl), or —C(O)—N($R^{601}$)$_2$ wherein:
  t is 0 or 1, and
  the $C_3$-$C_5$ cycloalkyl optionally includes an oxygen or nitrogen heteroatom;

each $R^{50}$ is independently H, —C(O)—O$_t$—($C_1$-$C_4$ straight or branched alkyl), —C(O)—O$_t$—($C_3$-$C_5$ cyclic alkyl), —$C_3$-$C_5$ cyclic alkyl optionally containing an oxygen or nitrogen heteroatom, —C(O)—N($R^{501}$)$_2$, $C_1$-$C_4$ straight or branched alkyl wherein:
  t is 0 or 1, and
  the $C_3$-$C_5$ cycloalkyl optionally includes an oxygen or nitrogen heteroatom;

n is 1, 2 or 3;

m is 1 or 2;

$R^{21}$ is H, halogen, $C_1$-$C_4$ straight or branched alkyl, $C_3$-$C_5$ cycloalkyl wherein the $C_3$-$C_5$ cycloalkyl optionally includes an oxygen or nitrogen heteroatom;

$R^{22}$ is H, halogen, $C_1$-$C_2$ alkyl;

each $R^{26}$ is independently —OH, —CN, halogen, $C_1$-$C_4$ straight or branched alkyl, —($C_1$-$C_4$ alkyl)$_t$-O$_t$—($C_3$-$C_5$ cycloalkyl), —($C_1$-$C_4$ alkyl)$_t$-O—($C_1$-$C_4$ straight or branched alkyl), —C(O)—O$_t$—($C_1$-$C_4$ alkyl), or —C(O)—N($R^{501}$)$_2$ wherein:
  t is 0 or 1, and
  the $C_3$-$C_5$ cycloalkyl optionally includes an oxygen or nitrogen heteroatom;

s is 0, 1 or 2;

each $R^{601}$ and $R^{501}$ is independently H or $C_1$-$C_4$ straight or branched alkyl; and wherein two of $R^{26}$, $R^{60}$, $R^{50}$, $R^{501}$ and $R^{601}$ optionally join to form a ring wherein the two of $R^{26}$, $R^{60}$, $R^{50}$, $R^{501}$ and $R^{601}$ may be two $R^{26}$, two $R^{60}$, two $R^{50}$, two $R^{501}$ or two $R^{601}$.

2. The compound of claim 1, wherein $R^{21}$ is halogen, $C_1$-$C_4$ straight or branched alkyl or $C_3$-$C_5$ cycloalkyl.

3. The compound of claim 1, wherein $R^1$ is —CN or $C_1$-$C_2$ haloalkyl.

4. The compound of claim 1, wherein $R^3$ is H or F.

5. The compound of claim 1, wherein $R^1$ is —CN.

6. The compound of claim 1, wherein $R^1$ is —CF$_3$.

7. The compound of claim 1, wherein n is 1 or 2.

8. The compound of claim 1, wherein m is 1.

9. The compound of claim 1, wherein m is 2.

10. The compound of claim 1, wherein $R^{21}$ is $C_1$-$C_2$ alkyl or $C_3$-$C_5$ cycloalkyl and $R^{22}$ is $C_1$-$C_2$ alkyl.

11. The compound of claim 1, wherein $R^{21}$ is $C_3$-$C_5$ cycloalkyl and $R^{22}$ is $C_1$-$C_2$ alkyl.

12. The compound of claim 1, wherein n is 2, m is 1, $L^3$ is —N—C(O)—O—($C_1$-$C_2$ alkyl).

13. The compound of claim 1, wherein $L^3$ is $NR^{50}$; $R^{50}$ is $C_1$-$C_2$ alkyl; $R^{21}$ is cyclobutyl; $R^{22}$ is H or methyl; $R^3$ is H; $R^1$ is —CN; m is 2 and n is 1 or 2.

14. The compound of claim 1, wherein n is 2, m is 1, $L^3$ is O and s is 0.

15. The compound of claim 1, wherein $R^{22}$ is H, methyl or ethyl.

16. The compound of claim 1, wherein $R^1$ is —CN, each $R^2$ is H, $R^3$ is H or F, $R^{21}$ is $C_3$-$C_4$ cycloalkyl, $R^{22}$ is methyl, n is 2 and $L^3$ is $NR^{50}$ wherein $R^{50}$ is methyl or ethyl.

17. The compound of claim 1, wherein $R^1$ is —CN, each $R^2$ is H, $R^3$ is H or F, $R^{21}$ is $C_3$-$C_4$ cycloalkyl, $R^{22}$ is methyl, n is 2 and $L^3$ is O.

18. The compound of claim 1, having a formula selected from the group consisting of:

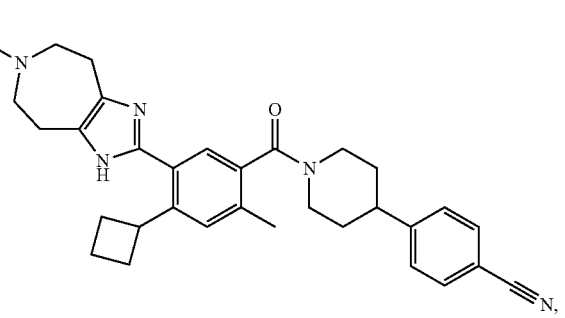

-continued
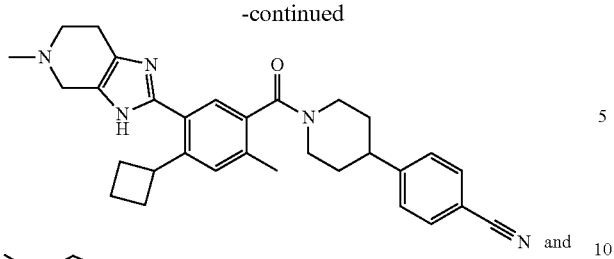
and
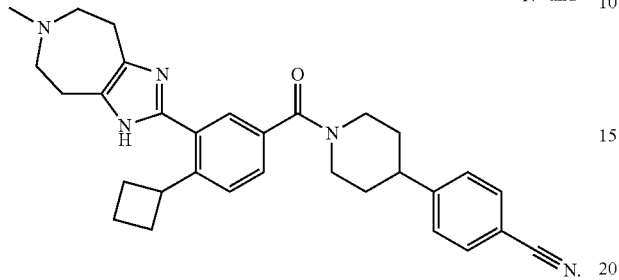
19. A pharmaceutical composition comprising a compound of claim 1 and a pharmaceutically acceptable carrier, excipient, or diluent.
* * * * *

UNITED STATES PATENT AND TRADEMARK OFFICE
CERTIFICATE OF CORRECTION

Page 1 of 2

PATENT NO. : 9,624,173 B2
APPLICATION NO. : 14/663347
DATED : April 18, 2017
INVENTOR(S) : Johan D. Oslob et al.

It is certified that error appears in the above-identified patent and that said Letters Patent is hereby corrected as shown below:

In the Claims

At Column 123, Claim number 1, Line number 47:
"-O-($C_3$-$C_5$ cycloalkyl), -O-($C_1$-$C_4$ straight or"
Should read:
-- -O-($C_3$-$C_5$ cycloalkyl), or -O-($C_1$-$C_4$ straight or --

At Column 123, Claim number 1, Line number 66:
"($R^{501}$)$_2$, $C_1$-$C_4$ straight or branched alkyl wherein:"
Should read:
-- ($R^{501}$)$_2$, or $C_1$-$C_4$ straight or branched alkyl wherein: --

At Column 124, Claim number 1, Line number 5:
"$R^{21}$ is H, halogen, $C_1$-$C_4$ straight or branched alkyl, $C_3$-$C_5$"
Should read:
-- $R^{21}$ is H, halogen, $C_1$-$C_4$ straight or branched alkyl, or $C_3$-$C_5$ --

At Column 124, Claim number 1, Line number 8:
"$R^{22}$ is H, halogen, $C_1$-$C_2$ alkyl;"
Should read:
-- $R^{22}$ is H, halogen, or $C_1$-$C_2$ alkyl; --

At Column 124, Claim number 1, Line number 17:
"s is 0, 1 or 2;"
Should read:
-- s is 0, 1 or 2; and --

At Column 124, Claim number 12, Line number 38:
"12. The compound of claim 1, wherein n is 2, m is 1, $L^3$"

Signed and Sealed this
Twentieth Day of July, 2021

Drew Hirshfeld
*Performing the Functions and Duties of the*
*Under Secretary of Commerce for Intellectual Property and*
*Director of the United States Patent and Trademark Office*

Should read:

-- 12. The compound of claim 1, wherein n is 2, m is 1, and L$^3$ --